(12) United States Patent
Wizemann et al.

(10) Patent No.: US 6,503,511 B1
(45) Date of Patent: Jan. 7, 2003

(54) DERIVATIVES OF CHOLINE BINDING PROTEINS FOR VACCINES

(75) Inventors: Theresa M. Wizemann, Potomac, MD (US); Scott Koenig, Rockville, MD (US); Leslie S. Johnson, Germantown, MD (US)

(73) Assignee: MedImmune, Inc., Gaithersburg, MD (US)

( * ) Notice: Subject to any disclaimer, the term of this patent is extended or adjusted under 35 U.S.C. 154(b) by 0 days.

(21) Appl. No.: 09/286,981

(22) Filed: Apr. 6, 1999

Related U.S. Application Data

(60) Provisional application No. 60/085,743, filed on May 15, 1998, and provisional application No. 60/080,878, filed on Apr. 7, 1998.

(51) Int. Cl.$^7$ .................. A61K 39/02; A61K 39/085; A61K 38/00; A61K 38/16; C07K 14/00
(52) U.S. Cl. ................. 424/190.1; 424/184.1; 424/234.1; 424/237.1; 424/244.1; 530/300; 530/350; 514/2; 514/8
(58) Field of Search ................ 424/184.1, 234.1, 424/244.1, 190.1, 237.1; 530/300, 350; 514/2, 8

(56) References Cited

U.S. PATENT DOCUMENTS

| | | | | |
|---|---|---|---|---|
| 5,980,909 A | * | 11/1999 | Briles et al. | |
| 6,027,734 A | * | 2/2000 | Briles et al. | |
| 6,042,838 A | * | 3/2000 | Briles et al. | |
| 6,231,870 B1 | * | 5/2001 | Briles et al. | |
| 6,232,116 B1 | * | 5/2001 | Briles et al. | |
| 6,245,335 B1 | * | 6/2001 | Masure et al. | |

FOREIGN PATENT DOCUMENTS

| | | | |
|---|---|---|---|
| WO | WO 97/09994 | | 3/1997 |
| WO | WO 97/41151 | * | 11/1997 |
| WO | WO/98/18930 | * | 5/1998 |
| WO | WO 98/21337 | * | 5/1998 |
| WO | WO 98/39450 | | 11/1998 |
| WO | 9951266 | * | 10/1999 |

OTHER PUBLICATIONS

Dermitzer et al, ASM General Meeting 98:56 Abstract only, 1998.*
Brooks–Walter et al, Infection & Immunity, 67/12:6533–42, 1999.*
Rosenow, C. et al., "Contribution of novel choline–binding proteins to adherence, colonization and immunogenicity of *Streptococcus pneumoniae*," *Blackwell Science Ltd., Molecular Microbiology*, pp. 819–829 (1997).
Talkington, D. et al., "A 43–Kioldalton Pneumococcal Surface Protein, PspA: Isolation, Protective Abilities, and Structural Analysis of the Amino–Terminal Sequence," *Infection and Immunity, American Society for Microbiology*, pp. 1285–1289 (Apr. 1991).
Hammerschmidt, S. et al., "SpsA, a novel pneumococcal surface protein with specific binding to secretory Immunoglobulin A and secretory component," *Blackwell Science Ltd., Molecular Microbiology*, pp. 1113–1124 (1997).
Yother, J. et al., "Truncated Forms of PspA That Are Secreted from *Streptococcus pneumoniae* and Their Use in Functional Studies and Cloning of the pspA Gene," *American Society for Microbiology, Journal of Bacteriology*, pp. 610–618 (Jan. 1992).
Yother, J. et al., "Structural Properties and Evolutionary Relationships of PspA, a surface Protein of *Streptococcus pneumoniae*, as Revealed by Sequence Analsys," *American Society for Microbiology, Journal of Bacteriology*, pp. 601–609 (Jan. 1992).
Creech Tart, R. et al., "Truncated *Streptococcus pneumoniae* PspA Molecules Elicit Cross–Protective Immunity against Pneumococcal Challenge in Mice," *The University of Chicago, The Journal of Infectious Diseases*, pp. 380–386 (1996).
Langermann, S. et al., "Protective Humoral Response Against Pneumococcal Infection in Mice Elicited by Recombinant Bacille Calmette–Guerin Vaccines Expressing Pneumococcal Surface Protein A," *The Rockefeller University Press*, vol. 180, pp. 2277–2286 (Dec. 1994).

* cited by examiner

Primary Examiner—Nita Minnifield
(74) Attorney, Agent, or Firm—Elliot M. Olstein; Alan J. Grant

(57) ABSTRACT

The present invention provides bacterial immunogenic agents for administration to humans and non-human animals to stimulate an immune response. It particularly relates to the vaccination of mammalian species with pneumococcal derived polypeptides that include an alpha helix but exclude a choline binding region as a mechanism for stimulating production of antibodies that protect the vaccine recipient against infection by pathogenic bacterial species. In another aspect the invention provides antibodies against such proteins and protein complexes that may be used as diagnositics and/or as protective/treatment agents for pathogenic bacterial species.

13 Claims, 16 Drawing Sheets

Percent Identity

| | 1 | 2 | 3 | 4 | 5 | 6 | 7 | 8 | 9 | 10 | 11 | 12 | 13 | 14 | 15 | 16 | 17 | | |
|---|---|---|---|---|---|---|---|---|---|---|---|---|---|---|---|---|---|---|---|
| 1 | | 30.7 | 31.7 | 28.6 | 100.0 | 19.8 | 19.0 | 31.7 | 33.0 | 36.3 | 36.3 | 37.3 | 30.2 | 32.3 | 31.7 | 23.3 | 37.0 | Norway4 | 1 |
| 2 | | | 63.4 | 55.1 | 30.7 | 39.6 | 34.7 | 63.4 | 75.0 | 65.3 | 65.3 | 64.4 | 27.9 | 59.4 | 63.4 | 37.6 | 62.0 | ATCC33400(1) | 2 |
| 3 | | | | 78.6 | 31.7 | 40.6 | 36.6 | 100.0 | 62.0 | 60.4 | 60.4 | 60.4 | 30.2 | 59.4 | 100.0 | 46.5 | 65.0 | ATCC11733(2) | 3 |
| 4 | | | | | 28.6 | 37.8 | 36.7 | 78.6 | 58.2 | 63.3 | 63.3 | 63.3 | 24.4 | 67.7 | 78.6 | 38.8 | 60.2 | ATCC2 | 4 |
| 5 | | | | | | 19.8 | 19.0 | 31.7 | 33.0 | 36.3 | 36.3 | 37.3 | 30.2 | 32.3 | 31.7 | 23.3 | 37.0 | ATCC4 | 5 |
| 6 | | | | | | | 89.5 | 40.6 | 41.0 | 38.2 | 38.2 | 37.3 | 51.2 | 41.7 | 40.6 | 64.1 | 38.0 | ATCC6B | 6 |
| 7 | | | | | | | | 36.6 | 35.0 | 35.3 | 35.3 | 34.3 | 48.8 | 38.5 | 36.6 | 60.2 | 34.0 | ATCC18C | 7 |
| 8 | | | | | | | | | 62.0 | 60.4 | 60.4 | 60.4 | 30.2 | 59.4 | 100.0 | 46.5 | 65.0 | R6X(2) | 8 |
| 9 | | | | | | | | | | 70.0 | 70.0 | 71.0 | 27.9 | 65.6 | 62.0 | 42.0 | 67.0 | SPB105(6B) | 9 |
| 10 | | | | | | | | | | | 100.0 | 99.0 | 27.9 | 63.5 | 60.4 | 45.1 | 81.0 | SPB328(23F) | 10 |
| 11 | | | | | | | | | | | | 99.0 | 27.9 | 63.5 | 60.4 | 45.1 | 81.0 | SPB331(14) | 11 |
| 12 | | | | | | | | | | | | | 27.9 | 64.6 | 60.4 | 45.1 | 82.0 | SPB365(23F) | 12 |
| 13 | | | | | | | | | | | | | | 23.3 | 30.2 | 66.3 | 29.1 | SPB609(6B) | 13 |
| 14 | | | | | | | | | | | | | | | 59.4 | 42.7 | 63.5 | SPR332(9V) | 14 |
| 15 | | | | | | | | | | | | | | | | 46.5 | 65.0 | SPSJ2(6B)p | 15 |
| 16 | | | | | | | | | | | | | | | | | 41.0 | SPSJ9(14) | 16 |
| 17 | | | | | | | | | | | | | | | | | | SPSJ12(19A) | 17 |

FIG. 12

Percent Identity

| | 1 | 2 | 3 | 4 | 5 | 6 | 7 | 8 | 9 | 10 | 11 | 12 | 13 | 14 | 15 | 16 | | |
|---|---|---|---|---|---|---|---|---|---|---|---|---|---|---|---|---|---|---|
| 1 | | 52.0 | 76.0 | 98.0 | 82.0 | 100.0 | 86.0 | 86.0 | 82.0 | 82.0 | 82.0 | 84.0 | 76.0 | 86.0 | 76.0 | 76.0 | 1 | Norway4 |
| 2 | | | 58.5 | 52.0 | 55.2 | 52.0 | 43.1 | 44.8 | 43.1 | 44.8 | 43.1 | 48.3 | 49.1 | 43.1 | 50.9 | 46.3 | 2 | ATCC33400(1) |
| 3 | | | | 76.0 | 81.1 | 76.0 | 71.7 | 71.7 | 69.8 | 69.8 | 69.8 | 69.8 | 69.8 | 71.7 | 71.7 | 69.8 | 3 | ATCC2 |
| 4 | | | | | 82.0 | 98.0 | 84.0 | 86.0 | 80.0 | 80.0 | 80.0 | 84.0 | 76.0 | 84.0 | 76.0 | 76.0 | 4 | ATCC4 |
| 5 | | | | | | 82.0 | 62.7 | 64.5 | 64.4 | 64.4 | 66.1 | 67.7 | 71.7 | 62.7 | 71.7 | 70.4 | 5 | ATCC6B |
| 6 | | | | | | | 86.0 | 86.0 | 82.0 | 82.0 | 82.0 | 84.0 | 76.0 | 86.0 | 76.0 | 76.0 | 6 | Norway14 |
| 7 | | | | | | | | 79.7 | 81.4 | 81.4 | 81.4 | 78.0 | 66.0 | 100.0 | 66.0 | 66.7 | 7 | R6X(2) |
| 8 | | | | | | | | | 78.0 | 78.0 | 78.0 | 83.9 | 69.8 | 79.7 | 67.9 | 66.7 | 8 | SPB105(6B) |
| 9 | | | | | | | | | | 98.3 | 98.3 | 78.0 | 67.9 | 81.4 | 67.9 | 64.8 | 9 | SPB328(23F) |
| 10 | | | | | | | | | | | 98.3 | 79.7 | 67.9 | 81.4 | 69.8 | 64.8 | 10 | SPB331(14) |
| 11 | | | | | | | | | | | | 78.0 | 69.8 | 81.4 | 67.9 | 64.8 | 11 | SPB365(23F) |
| 12 | | | | | | | | | | | | | 69.8 | 78.0 | 75.5 | 66.7 | 12 | SPB609(6B) |
| 13 | | | | | | | | | | | | | | 66.0 | 92.5 | 88.7 | 13 | SPR332(9V) |
| 14 | | | | | | | | | | | | | | | 66.0 | 66.7 | 14 | SPSJ2(6B)passaged |
| 15 | | | | | | | | | | | | | | | | 88.7 | 15 | SPSJ9(14) |
| 16 | | | | | | | | | | | | | | | | | 16 | SPSJ12(19A) |

SEQUENCE LISTING

<160> NUMBER OF SEQ ID NOS: 38

<210> SEQ ID NO 1
<211> LENGTH: 103
<212> TYPE: PRT
<213> ORGANISM: Streptococcus pneumoniae

<400> SEQUENCE: 1

```
Lys Lys Val Ala Glu Ala Glu Lys Lys Val Glu Glu Ala Lys Lys Lys
  1               5                  10                  15

Ala Glu Asp Gln Lys Glu Glu Asp Arg Arg Asn Tyr Pro Thr Asn Thr
             20                  25                  30

Tyr Lys Thr Leu Glu Leu Glu Ile Ala Glu Ser Asp Val Glu Val Lys
         35                  40                  45

Lys Ala Glu Leu Glu Leu Val Lys Glu Glu Ala Lys Glu Ser Arg Asn
     50                  55                  60

Glu Glu Lys Ile Lys Gln Ala Lys Ala Lys Val Glu Ser Lys Lys Ala
 65                  70                  75                  80

Glu Ala Thr Arg Leu Glu Lys Ile Lys Thr Asp Arg Lys Lys Ala Glu
                 85                  90                  95

Glu Glu Ala Lys Arg Lys Ala
            100
```

<210> SEQ ID NO 2
<211> LENGTH: 141
<212> TYPE: PRT
<213> ORGANISM: Streptococcus pneumoniae

<400> SEQUENCE: 2

```
Glu Ala Lys Arg Lys Ala Glu Ser Glu Lys Lys Ala Ala Glu Ala
  1               5                  10                  15
Lys Gln Lys Val Asp Ala Glu Tyr Ala Leu Glu Ala Lys Ile Ala
             20                  25                  30
Glu Leu Glu Tyr Glu Val Gln Arg Leu Glu Lys Glu Leu Lys Glu Ile
         35                  40                  45
Asp Glu Ser Asp Ser Glu Asp Tyr Leu Lys Glu Gly Leu Arg Ala Pro
     50                  55                  60
Leu Gln Ser Lys Leu Asp Thr Lys Lys Ala Lys Leu Ser Lys Leu Glu
 65                  70                  75                  80
Glu Leu Ser Asp Lys Ile Asp Glu Leu Asp Ala Glu Ile Ala Lys Leu
                 85                  90                  95
Glu Val Gln Leu Lys Asp Ala Glu Gly Asn Asn Asn Val Glu Ala Tyr
                100                 105                 110
Phe Lys Glu Gly Leu Glu Lys Thr Thr Ala Glu Lys Lys Ala Glu Leu
            115                 120                 125
Glu Lys Ala Glu Ala Asp Leu Lys Lys Ala Val Asp Glu
        130                 135                 140
```

<210> SEQ ID NO 3
<211> LENGTH: 431
<212> TYPE: PRT
<213> ORGANISM: Streptococcus pneumoniae

<400> SEQUENCE: 3

```
Thr Glu Lys Glu Val Thr Thr Pro Val Ala Thr Ser Ser Asn Lys Ala
  1               5                  10                  15
Asn Lys Ser Gln Thr Glu His Met Lys Ala Ala Glu Gln Val Asp Glu
             20                  25                  30
Tyr Ile Asn Lys Met Ile Gln Leu Asp Lys Arg Lys His Thr Gln Asn
         35                  40                  45
Leu Ala Leu Asn Ile Lys Leu Ser Ala Ile Lys Thr Lys Tyr Leu Arg
     50                  55                  60
Glu Leu Asn Val Leu Glu Glu Lys Ser Lys Lys Glu Glu Leu Thr Ser
 65                  70                  75                  80
Lys Thr Lys Lys Glu Ile Asp Ala Ala Phe Glu Gln Phe Asn Lys Asp
                 85                  90                  95
Thr Leu Lys Pro Gly Glu Lys Val Glu Glu Ala Glu Lys Lys Val Glu
            100                 105                 110
Glu Ala Glu Lys Lys Ala Lys Asp Gln Lys Glu Glu Asp His Arg Asn
            115                 120                 125
Tyr Pro Thr Ile Thr Tyr Lys Thr Leu Glu Leu Glu Ile Ala Glu Ser
        130                 135                 140
Asp Val Glu Val Lys Lys Ala Glu Leu Glu Leu Val Lys Glu Glu Ala
145                 150                 155                 160
Lys Gly Ser Arg Asn Glu Glu Lys Ile Lys Ala Lys Ala Glu Val
            165                 170                 175
Glu Ser Lys Lys Ala Glu Ala Thr Lys Leu Glu Glu Ile Lys Thr Glu
            180                 185                 190
Arg Lys Lys Ala Glu Glu Glu Ala Lys Arg Lys Ala Glu Ala Glu Glu
        195                 200                 205
Glu Val Lys Asn Lys Leu Lys Lys Arg Thr Lys Arg Gly Ala Phe Gly
        210                 215                 220
```

-continued

```
Glu Pro Ala Thr Pro Asp Lys Lys Glu Asn Asp Ala Lys Ser Ser Asp
225                 230                 235                 240

Ser Ser Val Val Lys Lys Ser Lys Pro Ile Leu Lys Ser Glu Lys
            245                 250                 255

Lys Val Ala Glu Ala Glu Lys Val Ala Glu Ala Glu Lys Lys Val
        260                 265                 270

Ala Glu Ala Glu Lys Lys Ala Lys Asp Gln Lys Glu Glu Asp Arg Arg
        275                 280                 285

Asn Tyr Pro Thr Asn Thr Tyr Lys Thr Leu Glu Leu Glu Ile Ala Glu
        290                 295                 300

Ser Asp Val Lys Val Lys Glu Ala Glu Leu Glu Leu Val Lys Glu Glu
305                 310                 315                 320

Ala Lys Glu Pro Gln Asn Glu Lys Ile Lys Gln Ala Lys Ala Lys
                325                 330                 335

Val Glu Ser Lys Lys Ala Glu Ala Thr Arg Leu Glu Lys Ile Lys Thr
        340                 345                 350

Asp Arg Lys Lys Ala Glu Ala Lys Arg Lys Val Ala Glu Glu Asp
        355                 360                 365

Lys Val Lys Glu Lys Pro Ala Glu Gln Pro Gln Pro Ala Pro Ala Pro
370                 375                 380

Lys Pro Ala Pro Ala Pro Gln Pro Glu Lys Pro Ala Glu Gln Pro Lys
385                 390                 395                 400

Ala Glu Lys Pro Ala Asp Gln Gln Ala Glu Asp Tyr Ala Arg Arg
                405                 410                 415

Ser Glu Glu Glu Tyr Asn Pro Leu Asp Leu Thr Ala Pro Ala Lys
                420                 425                 430

<210> SEQ ID NO 4
<211> LENGTH: 251
<212> TYPE: PRT
<213> ORGANISM: Streptococcus pneumoniae

<400> SEQUENCE: 4

Thr Glu Asn Glu Gly Ser Thr Gln Ala Ala Thr Ser Ser Asn Met Ala
  1               5                  10                  15

Lys Thr Glu His Arg Lys Ala Ala Lys Gln Val Val Asp Glu Tyr Ile
             20                  25                  30

Glu Lys Met Leu Arg Glu Ile Gln Leu Asp Arg Arg Lys His Thr Gln
         35                  40                  45

Asn Val Ala Leu Asn Ile Lys Leu Ser Ala Ile Lys Thr Lys Tyr Leu
     50                  55                  60

Arg Glu Leu Asn Val Leu Glu Glu Lys Ser Lys Asp Glu Leu Pro Ser
 65                  70                  75                  80

Glu Ile Lys Ala Lys Leu Asp Ala Ala Phe Glu Lys Phe Lys Lys Asp
                 85                  90                  95

Thr Leu Lys Pro Gly Glu Lys Val Ala Glu Ala Lys Lys Val Glu
            100                 105                 110

Glu Ala Lys Lys Lys Ala Glu Asp Gln Lys Glu Glu Asp Arg Arg Asn
        115                 120                 125

Tyr Pro Thr Asn Thr Tyr Lys Thr Leu Glu Leu Glu Ile Ala Glu Phe
        130                 135                 140

Asp Val Lys Val Lys Glu Ala Glu Leu Glu Leu Val Lys Glu Glu Ala
145                 150                 155                 160

Lys Glu Ser Arg Asn Glu Gly Thr Ile Lys Gln Ala Lys Glu Lys Val
```

|     |     |     |     | 165 |     |     |     | 170 |     |     |     | 175 |     |     |     |
| --- | --- | --- | --- | --- | --- | --- | --- | --- | --- | --- | --- | --- | --- | --- | --- |

Glu Ser Lys Lys Ala Glu Ala Thr Arg Leu Glu Asn Ile Lys Thr Asp
              180                 185                 190

Arg Lys Lys Ala Glu Glu Ala Lys Arg Lys Ala Ala Glu Glu Asp
         195                 200                 205

Lys Val Lys Glu Lys Pro Ala Glu Gln Pro Gln Pro Ala Pro Ala Thr
    210                 215                 220

Gln Pro Glu Lys Pro Ala Pro Lys Pro Glu Lys Pro Ala Glu Gln Pro
225                 230                 235                 240

Lys Ala Glu Lys Thr Asp Asp Gln Gln Ala Glu
                245                 250

<210> SEQ ID NO 5
<211> LENGTH: 413
<212> TYPE: PRT
<213> ORGANISM: Streptococcus pneumoniae

<400> SEQUENCE: 5

Thr Glu Lys Glu Val Thr Thr Gln Val Pro Thr Tyr Ser Asn Met Ala
 1               5                  10                  15

Lys Thr Glu His Arg Lys Ala Lys Gln Val Val Asp Glu Thr Ile
                20                  25                  30

Glu Lys Met Leu Arg Glu Ile Gln Leu Asp Arg Arg Lys His Thr Gln
             35                  40                  45

Asn Phe Ala Phe Asn Met Lys Leu Ser Ala Ile Lys Thr Glu Tyr Leu
         50                  55                  60

Tyr Gly Leu Lys Glu Lys Ser Glu Ala Glu Leu Pro Ser Glu Val Lys
 65                  70                  75                  80

Ala Lys Leu Asp Ala Ala Phe Glu Gln Phe Lys Lys Asp Thr Leu Lys
                 85                  90                  95

Pro Gly Glu Lys Val Ala Glu Ala Lys Lys Val Ala Glu Ala Glu
                100                 105                 110

Lys Lys Ala Lys Ala Gln Lys Glu Glu Asp Arg Arg Asn Tyr Pro Thr
            115                 120                 125

Asn Thr Tyr Lys Thr Leu Glu Leu Glu Ile Ala Glu Ser Asp Val Glu
130                 135                 140

Val Lys Lys Ala Glu Leu Glu Leu Leu Lys Glu Ala Lys Thr Arg
145                 150                 155                 160

Asn Glu Asp Thr Ile Asn Gln Ala Lys Ala Lys Val Glu Ser Lys Lys
                165                 170                 175

Ala Glu Ala Thr Leu Lys Glu Glu Ile Lys Thr Asp Arg Lys Lys Ala
            180                 185                 190

Glu Glu Glu Ala Lys Arg Lys Ala Glu Ala Glu Glu Asp Lys Val Lys
        195                 200                 205

Asp Lys Leu Lys Arg Arg Thr Lys Arg Ala Val Pro Gly Glu Pro Ala
    210                 215                 220

Thr Phe Phe Lys Lys Glu Asn Asp Ala Lys Ser Ser Asp Ser Val
225                 230                 235                 240

Gly Glu Glu Thr Leu Pro Ser Pro Ser Leu Lys Ser Gly Lys Lys Val
                245                 250                 255

Ala Glu Ala Glu Lys Lys Val Ala Glu Ala Glu Lys Lys Ala Lys Asp
            260                 265                 270

Gln Lys Glu Glu Asp Arg Arg Asn Tyr Pro Thr Asn Thr Thr Lys Thr
        275                 280                 285

-continued

```
Leu Asp Leu Glu Ile Ala Glu Ser Asp Val Lys Val Lys Glu Ala Glu
        290                 295                 300

Leu Glu Leu Val Lys Glu Ala Lys Gly Ser Arg Asn Glu Lys
305                 310                 315                 320

Ile Asn Gln Ala Lys Ala Glu Val Glu Ser Lys Lys Ala Glu Ala Thr
                325                 330                 335

Arg Leu Glu Lys Thr Lys Thr Asp Arg Lys Lys Ala Glu Glu Ala
            340                 345                 350

Lys Arg Lys Ala Ala Glu Glu Asp Lys Val Lys Glu Lys Pro Ala Glu
        355                 360                 365

Gln Pro Gln Pro Ala Pro Ala Pro Gln Pro Glu Lys Pro Thr Glu Glu
    370                 375                 380

Pro Glu Asn Pro Ala Pro Ala Pro Lys Pro Glu Lys Pro Ala Glu Gln
385                 390                 395                 400

Pro Lys Ala Glu Lys Thr Asp Asp Gln Gln Ala Glu Glu
                405                 410

<210> SEQ ID NO 6
<211> LENGTH: 446
<212> TYPE: PRT
<213> ORGANISM: Streptococcus pneumoniae

<400> SEQUENCE: 6

Thr Glu Asn Glu Gly Ala Thr Gln Val Pro Thr Ser Ser Asn Arg Ala
  1               5                  10                  15

Asn Glu Ser Gln Ala Glu Gln Gly Glu Gln Pro Lys Lys Leu Asp Ser
                20                  25                  30

Glu Arg Asp Lys Ala Arg Lys Glu Val Glu Glu Tyr Val Lys Lys Ile
            35                  40                  45

Val Gly Glu Ser Tyr Ala Lys Ser Thr Lys Lys Arg His Thr Ile Thr
    50                  55                  60

Val Ala Leu Val Asn Glu Leu Asn Asn Ile Lys Asn Glu Tyr Leu Asn
65                  70                  75                  80

Lys Ile Val Glu Ser Thr Ser Glu Ser Gln Leu Gln Ile Leu Met Met
                85                  90                  95

Glu Ser Arg Ser Lys Val Asp Glu Ala Val Ser Lys Phe Glu Lys Asp
            100                 105                 110

Ser Ser Ser Ser Ser Ser Asp Ser Ser Thr Lys Pro Glu Ala Ser
        115                 120                 125

Asp Thr Ala Lys Pro Asn Lys Pro Thr Glu Pro Gly Glu Lys Val Ala
    130                 135                 140

Glu Ala Lys Lys Lys Val Glu Glu Val Lys Lys Ala Lys Asp Gln
145                 150                 155                 160

Lys Glu Glu Asp Arg Arg Asn Tyr Pro Thr Ile Thr Tyr Lys Thr Leu
                165                 170                 175

Glu Leu Glu Ile Ala Glu Ser Asp Val Glu Val Lys Lys Ala Glu Leu
            180                 185                 190

Glu Leu Val Lys Val Lys Ala Asn Glu Pro Arg Asp Lys Gln Lys Ile
        195                 200                 205

Lys Gln Ala Glu Ala Glu Val Glu Ser Lys Gln Ala Glu Ala Thr Arg
    210                 215                 220

Leu Lys Lys Ile Lys Thr Asp Arg Glu Glu Ala Glu Glu Ala Lys
225                 230                 235                 240

Arg Arg Ala Asp Ala Lys Glu Gln Gly Lys Pro Lys Gly Arg Pro Lys
                245                 250                 255
```

-continued

```
Arg Gly Val Pro Gly Glu Leu Ala Thr Pro Asp Lys Lys Glu Asn Asp
            260                 265                 270

Ala Lys Ser Asp Ser Ser Val Gly Glu Glu Thr Leu Pro Ser Pro
        275                 280                 285

Ser Leu Lys Pro Glu Lys Lys Val Ala Glu Ala Glu Lys Lys Val Glu
        290                 295                 300

Glu Ala Lys Lys Lys Ala Glu Asp Gln Lys Glu Glu Asp Arg Arg Asn
305                 310                 315                 320

Tyr Pro Thr Asn Thr Tyr Lys Thr Leu Glu Leu Glu Ile Ala Glu Ser
                325                 330                 335

Asp Val Glu Val Lys Lys Ala Glu Leu Glu Leu Val Lys Glu Glu Ala
            340                 345                 350

Lys Glu Pro Arg Asn Glu Glu Lys Val Lys Gln Ala Lys Ala Glu Val
            355                 360                 365

Glu Ser Lys Lys Ala Glu Ala Thr Arg Leu Glu Lys Ile Lys Thr Asp
        370                 375                 380

Arg Lys Lys Ala Glu Glu Ala Lys Arg Lys Ala Ala Glu Glu Asp
385                 390                 395                 400

Lys Val Lys Glu Lys Pro Ala Glu Gln Pro Gln Pro Ala Pro Ala Pro
                405                 410                 415

Lys Thr Glu Lys Pro Ala Pro Ala Pro Lys Pro Glu Asn Pro Ala Glu
                420                 425                 430

Gln Pro Lys Ala Glu Lys Pro Ala Asp Gln Gln Ala Glu Glu
                435                 440                 445

<210> SEQ ID NO 7
<211> LENGTH: 428
<212> TYPE: PRT
<213> ORGANISM: Streptococcus pneumoniae

<400> SEQUENCE: 7

Glu Gly Val Arg Ser Gly Asn Asn Ser Thr Val Thr Ser Ser Gly Gln
  1               5                  10                  15

Asp Ile Ser Lys Lys Tyr Ala Asp Glu Val Glu Ser His Leu Gln Ser
                 20                  25                  30

Ile Leu Lys Asp Val Asn Lys Asn Leu Lys Lys Val Gln His Thr Gln
             35                  40                  45

Asn Ala Asp Phe Asn Lys Lys Leu Ser Lys Ile Lys Thr Lys Tyr Leu
         50                  55                  60

Tyr Glu Leu Asn Val Leu Glu Glu Lys Ser Glu Ala Glu Leu Thr Ser
 65                  70                  75                  80

Lys Thr Lys Glu Thr Lys Glu Leu Thr Ala Ala Phe Glu Gln Phe
                 85                  90                  95

Lys Lys Asp Thr Leu Ser Thr Gly Pro Glu Lys Val Ala Glu Ala
             100                 105                 110

Lys Lys Lys Val Glu Glu Ala Lys Lys Ala Glu Asp Gln Lys Glu
         115                 120                 125

Lys Asp Arg Arg Asn Tyr Pro Thr Ile Thr Tyr Lys Thr Leu Glu Leu
     130                 135                 140

Glu Ile Ala Glu Ser Asp Val Glu Val Lys Ala Glu Leu Glu Leu
145                 150                 155                 160

Val Lys Val Lys Ala Asn Glu Pro Arg Asp Glu Glu Lys Ile Lys Gln
                165                 170                 175

Ala Glu Ala Lys Val Glu Ser Lys Gln Ala Glu Ala Thr Arg Leu Lys
```

```
                  180                 185                 190
Lys Ile Lys Thr Asp Arg Glu Gln Ala Glu Ala Thr Arg Leu Glu Asn
            195                 200                 205

Ile Lys Thr Asp Arg Glu Gln Ala Glu Glu Ala Lys Val Lys Asp
            210                 215                 220

Glu Pro Lys Lys Arg Thr Lys Arg Gly Val Leu Gly Glu Pro Ala Thr
225                 230                 235                 240

Pro Asp Lys Lys Glu Asn Asp Ala Lys Ser Ser Asp Ser Ser Val Gly
            245                 250                 255

Glu Glu Thr Leu Pro Ser Pro Ser Leu Lys Pro Glu Lys Lys Val Ala
            260                 265                 270

Glu Ala Glu Lys Val Glu Glu Ala Lys Lys Ala Glu Asp Gln
            275                 280                 285

Lys Glu Glu Asp Arg Arg Asn Tyr Pro Thr Asn Thr Tyr Lys Thr Leu
            290                 295                 300

Glu Leu Glu Ile Ala Glu Ser Asp Val Glu Val Lys Lys Ala Glu Leu
305                 310                 315                 320

Glu Leu Val Lys Glu Ala Lys Glu Pro Arg Asn Glu Glu Lys Val
            325                 330                 335

Lys Gln Ala Lys Ala Glu Val Glu Ser Lys Gln Ala Glu Ala Thr Arg
            340                 345                 350

Leu Glu Asn Ile Lys Thr Asp Arg Lys Lys Ala Glu Glu Ala Lys
            355                 360                 365

Arg Lys Ala Ala Glu Glu Asp Lys Val Lys Glu Lys Pro Ala Glu Gln
            370                 375                 380

Pro Gln Pro Ala Pro Ala Pro Gln Pro Glu Lys Pro Ala Pro Lys Asp
385                 390                 395                 400

Glu Lys Pro Ala Pro Ala Pro Lys Pro Glu Asn Pro Ala Glu Gln Pro
                    405                 410                 415

Lys Ala Glu Lys Pro Ala Asp Gln Gln Ala Glu Glu
            420                 425

<210> SEQ ID NO 8
<211> LENGTH: 219
<212> TYPE: PRT
<213> ORGANISM: Streptococcus pneumoniae

<400> SEQUENCE: 8

Glu Gly Val Arg Ser Gly Asn Asn Ser Thr Val Thr Ser Ser Gly Gln
  1               5                  10                  15

Asp Ile Ser Lys Lys Tyr Ala Asp Glu Val Glu Ser His Leu Gln Ser
             20                  25                  30

Ile Leu Lys Asp Val Asn Lys Asn Leu Lys Lys Val Gln His Thr Gln
             35                  40                  45

Asn Ala Asp Phe Asn Lys Lys Leu Ser Lys Ile Lys Pro Lys Tyr Leu
         50                  55                  60

Tyr Glu Leu Lys Cys Leu Glu Glu Lys Ser Glu Ala Glu Leu Thr Ser
 65                  70                  75                  80

Lys Pro Lys Asn Lys Arg Arg Val Thr Ala Ala Phe Glu Gln Phe Lys
             85                  90                  95

Lys Asp Thr Leu Ser Thr Glu Pro Glu Lys Val Ala Glu Ala Lys
            100                 105                 110

Lys Lys Val Glu Glu Ala Lys Lys Lys Ala Glu Asp Gln Lys Glu Lys
            115                 120                 125
```

```
Asp Arg Arg Asn Tyr Pro Thr Ile Thr Tyr Lys Thr Leu Glu Leu Glu
        130                 135                 140

Ile Ala Glu Ser Asp Val Glu Val Lys Ala Glu Leu Glu Leu Val
145                 150                 155                 160

Lys Glu Glu Ala Lys Glu Pro Arg Asn Glu Glu Lys Val Lys Gln Ala
                165                 170                 175

Lys Ala Glu Val Glu Ser Lys Gln Ala Glu Ala Thr Arg Leu Glu Lys
                180                 185                 190

Ile Lys Thr Asp Arg Lys Lys Ala Glu Glu Ala Lys Arg Lys Ala
                195                 200                 205

Ala Glu Glu Asp Lys Val Lys Glu Lys Pro Ala
        210                 215
```

<210> SEQ ID NO 9
<211> LENGTH: 446
<212> TYPE: PRT
<213> ORGANISM: Streptococcus pneumoniae

<400> SEQUENCE: 9

```
Thr Glu Asn Glu Gly Ala Thr Gln Val Pro Thr Ser Ser Asn Arg Ala
  1               5                  10                  15

Asn Glu Ser Gln Ala Glu Gln Gly Gln Pro Lys Lys Leu Asp Ser
                20                  25                  30

Glu Arg Asp Lys Ala Arg Lys Glu Val Glu Glu Tyr Val Lys Lys Ile
            35                  40                  45

Val Gly Glu Ser Tyr Ala Lys Ser Thr Lys Lys Arg His Thr Ile Thr
 50                  55                  60

Val Ala Leu Val Asn Glu Leu Asn Asn Ile Lys Asn Glu Tyr Leu Asn
 65                  70                  75                  80

Lys Ile Val Glu Ser Thr Ser Glu Ser Gln Leu Gln Ile Leu Met Met
                85                  90                  95

Glu Ser Arg Ser Lys Val Asp Glu Ala Val Ser Lys Phe Glu Lys Asp
            100                 105                 110

Ser Ser Ser Ser Ser Ser Ser Asp Ser Ser Thr Lys Pro Glu Ala Ser
            115                 120                 125

Asp Thr Ala Lys Pro Asn Lys Pro Thr Glu Pro Gly Glu Lys Val Ala
        130                 135                 140

Glu Ala Lys Lys Val Glu Glu Ala Glu Lys Lys Ala Lys Asp Gln
145                 150                 155                 160

Lys Glu Glu Asp Arg Arg Asn Tyr Pro Thr Ile Thr Tyr Lys Thr Leu
                165                 170                 175

Glu Leu Glu Ile Ala Glu Ser Asp Val Glu Val Lys Lys Ala Glu Leu
                180                 185                 190

Glu Leu Val Lys Val Lys Ala Asn Glu Pro Arg Asp Glu Gln Lys Ile
                195                 200                 205

Lys Gln Ala Glu Ala Glu Val Glu Ser Lys Gln Ala Glu Ala Thr Arg
        210                 215                 220

Leu Lys Lys Ile Lys Thr Asp Arg Glu Glu Ala Glu Glu Glu Ala Lys
225                 230                 235                 240

Arg Arg Ala Asp Ala Lys Glu Gln Gly Lys Pro Lys Gly Arg Ala Lys
                245                 250                 255

Arg Gly Val Pro Gly Glu Leu Ala Thr Pro Asp Lys Lys Glu Asn Asp
            260                 265                 270

Ala Lys Ser Ser Asp Ser Ser Val Gly Glu Glu Thr Leu Pro Ser Pro
        275                 280                 285
```

```
Ser Leu Lys Pro Glu Lys Val Ala Glu Ala Glu Lys Lys Val Glu
    290                 295                 300

Glu Ala Lys Lys Ala Glu Asp Gln Lys Glu Glu Asp Arg Arg Asn
305                 310                 315                 320

Tyr Pro Thr Asn Thr Tyr Lys Thr Leu Glu Leu Glu Ile Ala Glu Ser
                325                 330                 335

Asp Val Glu Val Lys Lys Ala Glu Leu Glu Leu Val Lys Glu Glu Ala
                340                 345                 350

Lys Glu Pro Arg Asn Glu Glu Lys Val Lys Gln Ala Lys Ala Glu Val
            355                 360                 365

Glu Ser Lys Lys Ala Glu Ala Thr Arg Leu Glu Lys Ile Lys Thr Asp
    370                 375                 380

Arg Lys Lys Ala Glu Glu Ala Lys Arg Lys Ala Ala Glu Glu Asp
385                 390                 395                 400

Lys Val Lys Glu Lys Pro Ala Glu Gln Pro Gln Pro Ala Pro Ala Pro
                405                 410                 415

Lys Ala Glu Lys Pro Ala Pro Ala Pro Lys Pro Glu Asn Pro Ala Glu
            420                 425                 430

Gln Pro Lys Ala Glu Lys Pro Ala Asp Gln Gln Ala Glu Glu
        435                 440                 445

<210> SEQ ID NO 10
<211> LENGTH: 414
<212> TYPE: PRT
<213> ORGANISM: Streptococcus pneumoniae

<400> SEQUENCE: 10

Thr Glu Asn Glu Gly Ser Thr Gln Ala Ala Thr Ser Ser Asn Met Ala
  1               5                  10                  15

Lys Thr Glu His Arg Lys Ala Ala Lys Gln Val Val Asp Glu Tyr Ile
                20                  25                  30

Glu Lys Met Leu Arg Glu Ile Gln Leu Asp Arg Arg Lys His Thr Gln
            35                  40                  45

Asn Val Ala Leu Asn Ile Lys Leu Ser Ala Ile Lys Thr Lys Tyr Leu
    50                  55                  60

Arg Glu Leu Asn Val Leu Glu Glu Lys Ser Lys Asp Glu Leu Pro Ser
65                  70                  75                  80

Glu Ile Lys Ala Lys Leu Asp Ala Ala Phe Glu Lys Phe Lys Lys Asp
                85                  90                  95

Thr Leu Lys Pro Gly Glu Lys Val Ala Glu Ala Lys Lys Val Glu
                100                 105                 110

Glu Ala Lys Lys Ala Glu Asp Gln Lys Glu Glu Asp Arg Arg Asn
            115                 120                 125

Tyr Pro Thr Asn Thr Tyr Lys Thr Leu Glu Leu Glu Ile Ala Glu Phe
    130                 135                 140

Asp Val Lys Val Lys Glu Ala Glu Leu Glu Leu Val Lys Glu Glu Ala
145                 150                 155                 160

Lys Glu Ser Arg Asn Glu Gly Thr Ile Lys Gln Ala Lys Glu Lys Val
                165                 170                 175

Glu Ser Lys Lys Ala Glu Ala Thr Arg Leu Glu Asn Ile Lys Thr Asp
            180                 185                 190

Arg Lys Lys Ala Glu Glu Ala Lys Arg Lys Ala Asp Ala Lys Leu
    195                 200                 205

Lys Glu Ala Asn Val Ala Thr Ser Asp Gln Gly Lys Pro Lys Gly Arg
```

```
        210                 215                 220
Ala Lys Arg Gly Val Pro Gly Glu Leu Ala Thr Pro Asp Lys Lys Glu
225                 230                 235                 240

Asn Asp Ala Lys Ser Ser Asp Ser Ser Val Gly Glu Glu Thr Leu Pro
                245                 250                 255

Ser Ser Ser Leu Lys Ser Gly Lys Lys Val Ala Glu Ala Glu Lys Lys
            260                 265                 270

Val Glu Glu Ala Glu Lys Lys Ala Lys Asp Gln Lys Glu Glu Asp Arg
        275                 280                 285

Arg Asn Tyr Pro Thr Asn Thr Tyr Lys Thr Leu Asp Leu Glu Ile Ala
    290                 295                 300

Glu Ser Asp Val Lys Val Lys Glu Ala Glu Leu Glu Leu Val Lys Glu
305                 310                 315                 320

Glu Ala Lys Glu Pro Arg Asp Glu Glu Lys Ile Lys Gln Ala Lys Ala
                325                 330                 335

Lys Val Glu Ser Lys Lys Ala Glu Ala Thr Arg Leu Glu Asn Ile Lys
            340                 345                 350

Thr Asp Arg Asp Asp Ala Glu Glu Ala Lys Arg Lys Ala Ala Glu
        355                 360                 365

Glu Asp Lys Val Lys Glu Lys Pro Ala Glu Gln Pro Gln Pro Ala Pro
370                 375                 380

Ala Thr Gln Pro Glu Lys Pro Ala Pro Lys Pro Glu Lys Pro Ala Glu
385                 390                 395                 400

Gln Pro Lys Ala Glu Lys Thr Asp Asp Gln Gln Ala Glu Glu
                405                 410

<210> SEQ ID NO 11
<211> LENGTH: 425
<212> TYPE: PRT
<213> ORGANISM: Streptococcus pneumoniae

<400> SEQUENCE: 11

Thr Glu Lys Glu Val Thr Thr Gln Val Ala Thr Ser Ser Asn Arg Ala
 1               5                  10                  15

Asn Glu Ser Gln Ala Gly His Arg Lys Ala Ala Glu Gln Phe Asp Glu
            20                  25                  30

Tyr Ile Lys Thr Met Ile Gln Leu Asp Arg Arg Lys His Thr Gln Asn
        35                  40                  45

Phe Ala Leu Asn Ile Lys Leu Ser Arg Ile Lys Thr Glu Tyr Leu Arg
    50                  55                  60

Lys Leu Asn Val Leu Glu Glu Lys Ser Lys Ala Glu Leu Pro Ser Glu
65                  70                  75                  80

Thr Lys Lys Glu Ile Asp Ala Ala Phe Glu Gln Phe Lys Lys Asp Thr
                85                  90                  95

Asn Arg Thr Lys Lys Thr Val Ala Glu Ala Lys Lys Val Glu Glu
            100                 105                 110

Ala Lys Lys Lys Ala Lys Ala Gln Lys Glu Glu Asp His Arg Asn Tyr
        115                 120                 125

Pro Thr Asn Thr Tyr Lys Thr Leu Glu Leu Glu Ile Ala Glu Ser Asp
    130                 135                 140

Val Glu Val Lys Lys Ala Glu Leu Glu Leu Val Lys Glu Ala Lys
145                 150                 155                 160

Glu Ser Arg Asp Asp Glu Lys Ile Lys Gln Ala Glu Ala Lys Val Glu
                165                 170                 175
```

-continued

```
Ser Lys Lys Ala Glu Ala Thr Arg Leu Glu Asn Ile Lys Thr Asp Arg
            180                 185                 190

Glu Lys Ala Glu Glu Ala Lys Arg Arg Ala Glu Ala Lys Leu Lys
            195                 200                 205

Glu Ala Val Glu Lys Asn Val Ala Thr Ser Glu Gln Asp Lys Pro Lys
210                 215                 220

Gly Arg Arg Lys Arg Gly Val Pro Gly Glu Gln Ala Thr Pro Asp Lys
225                 230                 235                 240

Lys Glu Asn Asp Ala Lys Ser Ser Asp Ser Ser Val Gly Glu Ala
                245                 250                 255

Leu Pro Ser Pro Ser Leu Lys Pro Glu Lys Val Ala Glu Ala Glu
            260                 265                 270

Lys Lys Val Ala Glu Ala Glu Lys Ala Lys Ala Gln Lys Glu Glu
            275                 280                 285

Asp Arg Arg Asn Tyr Pro Thr Asn Thr Tyr Lys Thr Leu Glu Leu Glu
290                 295                 300

Ile Ala Glu Ser Asp Val Lys Val Lys Glu Ser Glu Leu Glu Leu Val
305                 310                 315                 320

Lys Glu Glu Ala Lys Glu Ser Arg Asn Glu Glu Lys Val Asn Gln Ala
                325                 330                 335

Lys Ala Lys Val Glu Ser Lys Lys Ala Glu Ala Thr Arg Leu Glu Lys
            340                 345                 350

Ile Lys Thr Asp Arg Lys Lys Ala Glu Glu Ala Lys Arg Lys Ala
            355                 360                 365

Ala Glu Glu Asp Lys Val Lys Glu Lys Pro Ala Glu Gln Pro Gln Pro
370                 375                 380

Ala Pro Ala Pro Gln Pro Glu Lys Pro Thr Glu Glu Pro Glu Asn Pro
385                 390                 395                 400

Ala Pro Ala Pro Lys Pro Glu Lys Pro Ala Glu Gln Pro Lys Ala Glu
                405                 410                 415

Lys Thr Asp Asp Gln Gln Ala Glu Glu
            420                 425
```

<210> SEQ ID NO 12
<211> LENGTH: 426
<212> TYPE: PRT
<213> ORGANISM: Streptococcus pneumoniae

<400> SEQUENCE: 12

```
Thr Glu Lys Glu Val Thr Thr Gln Val Ala Thr Ser Ser Asn Lys Ala
  1               5                  10                  15

Asn Lys Ser Gln Thr Glu His Met Lys Ala Ala Lys Gln Val Asp Glu
            20                  25                  30

Tyr Ile Lys Lys Lys Ile Gln Leu Asp Arg Arg Lys His Thr Gln Asn
        35                  40                  45

Val Gly Leu Leu Thr Lys Leu Gly Val Ile Lys Thr Glu Tyr Leu His
50                  55                  60

Gly Leu Ser Val Ser Lys Lys Ser Glu Ala Glu Leu Pro Ser Glu
65                  70                  75                  80

Ile Lys Ala Lys Leu Asp Ala Ala Phe Glu Gln Phe Lys Lys Asp Thr
            85                  90                  95

Leu Pro Thr Glu Pro Gly Lys Lys Val Ala Glu Ala Glu Lys Lys Val
            100                 105                 110

Glu Glu Ala Lys Lys Lys Ala Glu Asp Gln Lys Glu Lys Asp Leu Arg
            115                 120                 125
```

```
Asn Tyr Pro Thr Asn Thr Tyr Lys Thr Leu Glu Leu Asp Ile Ala Glu
    130                 135                 140
Ser Asp Val Glu Val Lys Lys Ala Glu Leu Glu Leu Val Lys Glu Glu
145                 150                 155                 160
Ala Lys Glu Ser Arg Asp Glu Lys Lys Ile Asn Gln Ala Lys Ala Lys
                165                 170                 175
Val Glu Asn Lys Lys Ala Glu Ala Thr Arg Leu Lys Asn Ile Lys Thr
            180                 185                 190
Asp Arg Glu Lys Ala Glu Ala Lys Arg Ala Asp Ala Lys Leu
        195                 200                 205
Gln Glu Ala Asn Val Ala Thr Ser Glu Gln Asp Lys Ser Lys Arg Arg
    210                 215                 220
Ala Lys Arg Glu Val Leu Gly Glu Leu Ala Thr Pro Asp Lys Lys Glu
225                 230                 235                 240
Asn Asp Ala Lys Ser Ser Asp Ser Ser Val Gly Glu Glu Thr Leu Thr
                245                 250                 255
Ser Pro Ser Leu Lys Pro Glu Lys Val Ala Glu Ala Glu Lys Lys
            260                 265                 270
Val Glu Glu Ala Lys Lys Lys Ala Glu Asp Gln Lys Glu Glu Asp Arg
        275                 280                 285
Arg Asn Tyr Pro Thr Asn Thr Tyr Lys Thr Leu Glu Leu Glu Ile Ala
    290                 295                 300
Glu Ser Asp Val Glu Val Lys Lys Ala Glu Leu Glu Leu Val Lys Glu
305                 310                 315                 320
Glu Ala Lys Glu Ser Arg Asn Glu Glu Lys Ile Lys Gln Val Lys Ala
                325                 330                 335
Lys Val Glu Ser Lys Lys Ala Glu Ala Thr Arg Leu Glu Asn Ile Lys
            340                 345                 350
Thr Asp Arg Lys Lys Ala Glu Glu Glu Ala Lys Arg Arg Ala Ala
        355                 360                 365
Glu Glu Asp Lys Val Lys Glu Lys Pro Ala Glu Gln Pro Gln Pro Ala
    370                 375                 380
Pro Ala Pro Gln Pro Glu Lys Pro Thr Glu Glu Pro Glu Asn Pro Ala
385                 390                 395                 400
Pro Ala Pro Ala Pro Lys Pro Glu Asn Pro Ala Glu Lys Pro Lys Ala
                405                 410                 415
Glu Lys Pro Ala Asp Gln Gln Ala Glu Glu
            420                 425

<210> SEQ ID NO 13
<211> LENGTH: 425
<212> TYPE: PRT
<213> ORGANISM: Streptococcus pneumoniae

<400> SEQUENCE: 13

Thr Glu Lys Glu Val Thr Thr Gln Val Ala Thr Ser Ser Asn Lys Ala
 1               5                  10                  15
Asn Lys Ser Gln Thr Glu His Met Lys Ala Ala Lys Gln Val Asp Glu
            20                  25                  30
Tyr Ile Lys Lys Lys Leu Gln Leu Asp Arg Arg Lys His Thr Gln Asn
        35                  40                  45
Val Gly Leu Leu Thr Lys Leu Gly Val Ile Lys Thr Glu Tyr Leu His
    50                  55                  60
Gly Leu Ser Val Ser Lys Lys Lys Ser Glu Ala Glu Leu Pro Ser Glu
```

```
                65                  70                  75                  80
          Ile Lys Ala Lys Leu Asp Ala Ala Phe Glu Gln Phe Lys Lys Asp Thr
                              85                  90                  95

Leu Pro Thr Glu Pro Gly Lys Lys Val Ala Glu Ala Glu Lys Lys Val
                             100                 105                 110

Glu Glu Ala Lys Lys Ala Glu Asp Gln Lys Glu Lys Asp Leu Arg
                             115                 120                 125

Asn Tyr Pro Thr Asn Thr Tyr Lys Thr Leu Glu Leu Asp Ile Ala Glu
                   130                 135                 140

Ser Asp Val Glu Val Lys Lys Ala Glu Leu Glu Leu Val Lys Glu Glu
          145                 150                 155                 160

Ala Lys Glu Ser Arg Asp Glu Lys Lys Ile Asn Gln Ala Lys Ala Lys
                             165                 170                 175

Val Glu Asn Lys Lys Ala Glu Ala Thr Arg Leu Lys Asn Ile Lys Thr
                             180                 185                 190

Asp Arg Glu Lys Ala Glu Glu Ala Lys Arg Arg Ala Asp Ala Lys Leu
                             195                 200                 205

Gln Glu Ala Asn Val Ala Thr Ser Glu Gln Asp Lys Ser Lys Arg Arg
                   210                 215                 220

Ala Lys Arg Glu Val Phe Gly Glu Leu Ala Thr Pro Asp Lys Lys Glu
          225                 230                 235                 240

Asn Asp Ala Lys Ser Ser Asp Ser Ser Val Gly Glu Glu Thr Leu Thr
                             245                 250                 255

Ser Pro Ser Leu Lys Pro Glu Lys Lys Val Ala Glu Ala Glu Lys Lys
                             260                 265                 270

Val Glu Glu Ala Lys Lys Ala Glu Asp Gln Lys Glu Glu Asp Arg
                             275                 280                 285

Arg Asn Tyr Pro Thr Asn Thr Tyr Lys Thr Leu Glu Leu Glu Ile Ala
                   290                 295                 300

Glu Ser Asp Val Glu Val Lys Lys Ala Glu Leu Glu Leu Val Lys Glu
          305                 310                 315                 320

Glu Ala Lys Glu Ser Arg Asn Glu Glu Lys Ile Lys Gln Val Lys Ala
                             325                 330                 335

Lys Val Glu Ser Lys Lys Ala Glu Ala Thr Arg Leu Glu Asn Ile Lys
                             340                 345                 350

Thr Asp Arg Lys Lys Ala Glu Glu Glu Ala Lys Arg Arg Ala Ala
                             355                 360                 365

Glu Glu Asp Lys Val Lys Glu Lys Pro Ala Glu Gln Pro Gln Pro Ala
                   370                 375                 380

Pro Ala Pro Gln Pro Glu Lys Pro Thr Glu Glu Pro Glu Asn Pro Ala
          385                 390                 395                 400

Pro Ala Pro Ala Pro Lys Pro Glu Asn Pro Ala Glu Lys Pro Lys Ala
                             405                 410                 415

Glu Lys Pro Ala Asp Gln Gln Ala Glu
                   420                 425

<210> SEQ ID NO 14
<211> LENGTH: 424
<212> TYPE: PRT
<213> ORGANISM: Streptococcus pneumoniae

<400> SEQUENCE: 14

Thr Glu Lys Glu Val Thr Thr Gln Val Ala Thr Ser Ser Asn Arg Ala
 1               5                  10                  15
```

-continued

```
Asn Lys Ser Gln Thr Glu His Met Lys Ala Ala Lys Gln Val Asp Glu
         20                  25                  30

Tyr Ile Lys Lys Lys Leu Gln Leu Asp Arg Arg Lys His Thr Gln Asn
             35                  40                  45

Val Gly Leu Leu Thr Lys Leu Gly Val Ile Lys Thr Glu Tyr Leu His
     50                  55                  60

Gly Leu Ser Val Ser Lys Lys Ser Glu Ala Glu Leu Pro Ser Glu
 65                  70                  75                  80

Ile Lys Ala Lys Leu Asp Ala Ala Phe Glu Gln Phe Lys Lys Asp Thr
                 85                  90                  95

Leu Pro Thr Glu Pro Gly Lys Lys Val Ala Glu Ala Glu Lys Lys Val
             100                 105                 110

Glu Glu Ala Lys Lys Ala Glu Asp Gln Lys Glu Lys Asp Leu Arg
         115                 120                 125

Asn Tyr Pro Thr Asn Thr Tyr Lys Thr Leu Glu Leu Asp Ile Ala Glu
 130                 135                 140

Ser Asp Val Glu Val Lys Lys Ala Glu Leu Glu Leu Val Lys Glu Glu
145                 150                 155                 160

Ala Lys Glu Ser Arg Asp Glu Lys Lys Ile Asn Gln Ala Lys Ala Lys
                 165                 170                 175

Val Glu Asn Lys Lys Ala Glu Ala Thr Arg Leu Lys Asn Ile Lys Thr
             180                 185                 190

Asp Arg Glu Lys Ala Glu Glu Ala Lys Arg Arg Ala Asp Ala Lys Leu
         195                 200                 205

Gln Glu Ala Asn Val Ala Thr Ser Glu Gln Asp Lys Ser Lys Arg Arg
 210                 215                 220

Ala Lys Arg Glu Val Leu Gly Glu Leu Ala Thr Pro Asp Lys Lys Glu
225                 230                 235                 240

Asn Asp Ala Lys Ser Ser Asp Ser Ser Val Gly Glu Glu Thr Leu Thr
                 245                 250                 255

Ser Pro Ser Leu Lys Pro Glu Lys Lys Val Ala Glu Ala Glu Lys Lys
             260                 265                 270

Val Glu Glu Ala Lys Lys Lys Ala Glu Asp Gln Lys Glu Glu Asp Arg
         275                 280                 285

Arg Asn Tyr Pro Thr Asn Thr Tyr Lys Thr Leu Glu Leu Glu Ile Ala
 290                 295                 300

Glu Ser Asp Val Glu Val Lys Lys Ala Glu Leu Glu Leu Val Lys Glu
305                 310                 315                 320

Glu Ala Lys Glu Ser Arg Asn Glu Glu Lys Ile Lys Gln Val Lys Ala
                 325                 330                 335

Lys Val Glu Ser Lys Lys Ala Glu Ala Thr Arg Leu Glu Asn Ile Lys
             340                 345                 350

Thr Asp Arg Lys Lys Ala Glu Glu Glu Ala Lys Arg Arg Ala Ala
         355                 360                 365

Glu Glu Asp Lys Val Lys Glu Lys Pro Ala Glu Gln Pro Gln Pro Ala
 370                 375                 380

Pro Ala Pro Gln Pro Glu Lys Pro Thr Glu Glu Pro Glu Asn Pro Ala
385                 390                 395                 400

Pro Ala Pro Ala Pro Lys Pro Glu Asn Pro Ala Glu Lys Pro Lys Ala
                 405                 410                 415

Glu Lys Pro Ala Asp Gln Gln Ala
             420
```

<210> SEQ ID NO 15
<211> LENGTH: 419
<212> TYPE: PRT
<213> ORGANISM: Streptococcus pneumoniae

<400> SEQUENCE: 15

| | | | | | | | | | | | | | | |
|---|---|---|---|---|---|---|---|---|---|---|---|---|---|---|
| Thr | Glu | Asn | Glu | Arg | Thr | Thr | Gln | Val | Pro | Thr | Ser | Ser | Asn | Arg | Gly |
| 1 | | | | 5 | | | | | 10 | | | | | 15 | |
| Lys | Pro | Glu | Arg | Arg | Lys | Ala | Ala | Glu | Gln | Phe | Asp | Glu | Tyr | Ile | Asn |
| | | | 20 | | | | | 25 | | | | | 30 | | |
| Lys | Met | Ile | Gln | Leu | Asp | Lys | Arg | Lys | His | Thr | Gln | Asn | Leu | Ala | Phe |
| | | 35 | | | | | 40 | | | | | 45 | | | |
| Asn | Ile | Gln | Leu | Ser | Arg | Ile | Lys | Thr | Glu | Tyr | Leu | Asn | Gly | Leu | Lys |
| | 50 | | | | | 55 | | | | | 60 | | | | |
| Glu | Lys | Ser | Glu | Ala | Glu | Leu | Pro | Ser | Lys | Ile | Lys | Ala | Glu | Leu | Asp |
| 65 | | | | | 70 | | | | | 75 | | | | | 80 |
| Ala | Ala | Phe | Lys | Gln | Phe | Lys | Lys | Asp | Thr | Leu | Pro | Thr | Glu | Pro | Glu |
| | | | | 85 | | | | | 90 | | | | | 95 | |
| Lys | Lys | Val | Ala | Glu | Ala | Glu | Lys | Lys | Val | Glu | Glu | Ala | Glu | Lys | Lys |
| | | | 100 | | | | | 105 | | | | | 110 | | |
| Val | Ala | Glu | Ala | Lys | Lys | Lys | Ala | Lys | Ala | Gln | Lys | Glu | Glu | Asp | His |
| | | 115 | | | | | 120 | | | | | 125 | | | |
| Arg | Asn | Tyr | Pro | Thr | Ile | Thr | Tyr | Lys | Thr | Leu | Asp | Leu | Glu | Ile | Ala |
| | 130 | | | | | 135 | | | | | 140 | | | | |
| Glu | Phe | Asp | Val | Lys | Val | Lys | Glu | Ala | Glu | Leu | Glu | Leu | Val | Lys | Lys |
| 145 | | | | | 150 | | | | | 155 | | | | | 160 |
| Glu | Ala | Asp | Glu | Ser | Arg | Asn | Glu | Gly | Thr | Ile | Asn | Gln | Ala | Lys | Ala |
| | | | | 165 | | | | | 170 | | | | | 175 | |
| Lys | Val | Glu | Ser | Glu | Lys | Ala | Glu | Ala | Thr | Arg | Leu | Lys | Lys | Ile | Lys |
| | | | 180 | | | | | 185 | | | | | 190 | | |
| Thr | Asp | Arg | Glu | Lys | Ala | Glu | Glu | Glu | Ala | Lys | Arg | Arg | Ala | Asp | |
| | | 195 | | | | | 200 | | | | | 205 | | | |
| Ala | Lys | Glu | Gln | Asp | Glu | Ser | Lys | Arg | Arg | Lys | Ser | Arg | Gly | Lys | Arg |
| | 210 | | | | | 215 | | | | | 220 | | | | |
| Gly | Ala | Leu | Gly | Glu | Gln | Ala | Thr | Pro | Asp | Lys | Lys | Glu | Asn | Asp | Ala |
| 225 | | | | | 230 | | | | | 235 | | | | | 240 |
| Lys | Ser | Ser | Asp | Ser | Ser | Val | Gly | Glu | Glu | Thr | Leu | Pro | Ser | Pro | Ser |
| | | | | 245 | | | | | 250 | | | | | 255 | |
| Leu | Lys | Pro | Gly | Lys | Lys | Val | Ala | Glu | Ala | Lys | Lys | Val | Glu | Glu | |
| | | | 260 | | | | | 265 | | | | | 270 | | |
| Ala | Asp | Lys | Lys | Ala | Lys | Ala | Gln | Lys | Glu | Glu | Asp | Arg | Arg | Asn | Tyr |
| | | 275 | | | | | 280 | | | | | 285 | | | |
| Pro | Thr | Asn | Thr | Tyr | Lys | Thr | Leu | Glu | Leu | Glu | Ile | Ala | Glu | Ser | Asp |
| | 290 | | | | | 295 | | | | | 300 | | | | |
| Val | Lys | Val | Lys | Glu | Ala | Glu | Leu | Glu | Leu | Val | Lys | Glu | Glu | Ala | Lys |
| 305 | | | | | 310 | | | | | 315 | | | | | 320 |
| Glu | Ser | Arg | Asn | Glu | Glu | Lys | Ile | Lys | Gln | Ala | Lys | Ala | Lys | Val | Glu |
| | | | | 325 | | | | | 330 | | | | | 335 | |
| Ser | Lys | Lys | Ala | Glu | Ala | Thr | Arg | Leu | Glu | Lys | Ile | Lys | Thr | Asp | Arg |
| | | | 340 | | | | | 345 | | | | | 350 | | |
| Lys | Lys | Ala | Glu | Glu | Glu | Ala | Lys | Arg | Lys | Ala | Ala | Glu | Glu | Asp | Lys |
| | | 355 | | | | | 360 | | | | | 365 | | | |
| Val | Lys | Glu | Lys | Pro | Ala | Glu | Gln | Pro | Gln | Pro | Ala | Pro | Ala | Pro | Gln |
| | 370 | | | | | 375 | | | | | 380 | | | | |

Pro Glu Lys Pro Ala Glu Pro Glu Asn Pro Val Pro Ala Pro Lys
385                 390                 395                 400

Pro Glu Asn Pro Ala Glu Gln Pro Lys Ala Glu Lys Pro Ala Asp Gln
            405                 410                 415

Gln Ala Glu

<210> SEQ ID NO 16
<211> LENGTH: 414
<212> TYPE: PRT
<213> ORGANISM: Streptococcus pneumoniae

<400> SEQUENCE: 16

Thr Glu Asn Glu Gly Ser Thr Gln Ala Ala Thr Ser Ser Asn Met Ala
1               5                   10                  15

Lys Thr Glu His Arg Lys Ala Ala Lys Gln Val Val Asp Glu Tyr Ile
            20                  25                  30

Glu Lys Met Leu Arg Glu Ile Gln Leu Asp Arg Arg Lys His Thr Gln
        35                  40                  45

Asn Val Ala Leu Asn Ile Lys Leu Ser Ala Ile Lys Thr Lys Tyr Leu
    50                  55                  60

Arg Glu Leu Asn Val Leu Glu Lys Ser Lys Asp Glu Leu Pro Ser
65                  70                  75                  80

Glu Ile Lys Ala Lys Leu Asp Ala Ala Phe Glu Lys Glu Lys Lys Asp
                85                  90                  95

Thr Leu Lys Pro Gly Glu Lys Val Ala Glu Ala Lys Lys Lys Val Glu
            100                 105                 110

Glu Ala Lys Lys Lys Ala Glu Asp Gln Lys Glu Glu Asp Arg Arg Asn
        115                 120                 125

Tyr Pro Thr Asn Thr Tyr Lys Thr Leu Glu Leu Glu Ile Ala Glu Phe
    130                 135                 140

Asp Val Lys Val Lys Glu Ala Glu Leu Glu Leu Val Lys Glu Glu Ala
145                 150                 155                 160

Lys Glu Ser Arg Asn Glu Gly Thr Ile Lys Gln Ala Lys Glu Lys Val
                165                 170                 175

Glu Ser Lys Lys Ala Glu Ala Thr Arg Leu Glu Asn Ile Lys Thr Asp
            180                 185                 190

Arg Lys Lys Ala Glu Glu Glu Ala Lys Arg Lys Ala Asp Ala Lys Leu
        195                 200                 205

Lys Glu Ala Asn Val Ala Thr Ser Asp Gln Gly Lys Pro Lys Gly Arg
    210                 215                 220

Ala Lys Arg Gly Val Pro Gly Glu Leu Ala Thr Pro Asp Lys Lys Glu
225                 230                 235                 240

Asn Asp Ala Lys Ser Ser Asp Ser Ser Val Gly Glu Glu Thr Leu Pro
                245                 250                 255

Ser Ser Ser Leu Lys Ser Gly Lys Lys Val Ala Glu Ala Glu Lys Lys
            260                 265                 270

Val Glu Glu Ala Glu Lys Lys Ala Lys Asp Gln Lys Glu Glu Asp Arg
        275                 280                 285

Arg Asn Tyr Pro Thr Asn Thr Tyr Lys Thr Leu Asp Leu Glu Ile Ala
    290                 295                 300

Glu Ser Asp Val Lys Val Lys Glu Ala Glu Leu Glu Leu Val Lys Glu
305                 310                 315                 320

Glu Ala Lys Glu Pro Arg Asp Glu Glu Lys Ile Lys Gln Ala Lys Ala
                325                 330                 335

```
Lys Val Glu Ser Lys Lys Ala Glu Ala Thr Arg Leu Glu Asn Ile Lys
            340                 345                 350

Thr Asp Arg Lys Lys Ala Glu Glu Ala Lys Arg Lys Ala Ala Glu
            355                 360                 365

Glu Asp Lys Val Lys Glu Lys Pro Ala Glu Gln Pro Gln Pro Ala Pro
            370                 375                 380

Ala Thr Gln Pro Glu Lys Pro Ala Pro Lys Pro Glu Lys Pro Ala Glu
385                 390                 395                 400

Gln Pro Lys Ala Glu Lys Thr Asp Asp Gln Gln Ala Glu Glu
                405                 410

<210> SEQ ID NO 17
<211> LENGTH: 412
<212> TYPE: PRT
<213> ORGANISM: Streptococcus pneumoniae

<400> SEQUENCE: 17

Glu Gly Val Arg Ser Glu Asn Asn Pro Thr Val Thr Ser Ser Gly Gln
1               5                   10                  15

Asp Ile Ser Lys Lys Tyr Ala Asp Glu Val Lys Ser His Leu Glu Lys
            20                  25                  30

Ile Leu Ser Glu Ile Gln Thr Asn Leu Asp Arg Ser Lys His Ile Lys
        35                  40                  45

Thr Val Asn Leu Ile Asn Lys Leu Gln Asp Ile Lys Arg Thr Tyr Leu
    50                  55                  60

Tyr Glu Leu Asn Val Leu Glu Asp Lys Ser Lys Ala Glu Leu Pro Ser
65                  70                  75                  80

Lys Ile Lys Ala Glu Leu Asp Ala Ala Phe Glu Gln Phe Lys Lys Asp
                85                  90                  95

Thr Leu Pro Thr Glu Pro Gly Lys Lys Val Ala Glu Ala Lys Lys Lys
            100                 105                 110

Val Glu Glu Ala Glu Lys Lys Ala Lys Ala Gln Lys Glu Glu Asp Tyr
        115                 120                 125

Arg Asn Tyr Pro Thr Ile Thr Tyr Lys Thr Leu Glu Leu Glu Ile Ala
    130                 135                 140

Glu Ser Asp Val Lys Val Lys Glu Ala Glu Leu Glu Leu Val Lys Lys
145                 150                 155                 160

Glu Ala Asp Glu Ser Arg Asn Glu Gly Thr Ile Asn Gln Ala Lys Ala
                165                 170                 175

Lys Val Glu Ser Glu Gln Ala Glu Ala Thr Arg Leu Lys Lys Ile Lys
            180                 185                 190

Thr Asp Arg Glu Lys Ala Glu Glu Ala Lys Arg Arg Ala Asp Ala
            195                 200                 205

Lys Glu Gln Asp Glu Ser Lys Arg Arg Lys Ser Arg Val Lys Arg Gly
        210                 215                 220

Asp Phe Gly Glu Pro Ala Thr Pro Asp Lys Lys Glu Asn Asp Ala Lys
225                 230                 235                 240

Ser Ser Asp Ser Ser Val Gly Glu Glu Thr Leu Pro Ser Pro Ser Leu
                245                 250                 255

Lys Pro Gly Lys Lys Val Ala Glu Ala Glu Lys Lys Val Glu Glu Ala
            260                 265                 270

Glu Lys Lys Ala Lys Asp Gln Lys Glu Glu Asp His Arg Asn Tyr Pro
        275                 280                 285

Thr Ile Thr Tyr Lys Thr Leu Glu Leu Glu Ile Ala Glu Ser Asp Val
    290                 295                 300
```

-continued

Glu Val Lys Lys Ala Glu Leu Glu Leu Val Lys Glu Ala Lys Gly
305                 310                 315                 320

Ser Arg Asn Glu Glu Lys Val Lys Gln Ala Lys Ala Glu Val Glu Ser
                325                 330                 335

Lys Lys Ala Glu Ala Thr Arg Leu Glu Lys Ile Lys Thr Asp Arg Lys
            340                 345                 350

Lys Ala Glu Glu Glu Ala Lys Arg Lys Ala Ala Glu Glu Asp Lys Val
            355                 360                 365

Lys Glu Lys Pro Ala Glu Gln Pro Gln Pro Ala Pro Ala Pro Gln Pro
        370                 375                 380

Glu Lys Pro Ala Pro Ala Pro Lys Pro Glu Asn Pro Ala Glu Gln Pro
385                 390                 395                 400

Lys Ala Glu Lys Pro Ala Asp Gln Gln Ala Glu Glu
                405                 410

<210> SEQ ID NO 18
<211> LENGTH: 406
<212> TYPE: PRT
<213> ORGANISM: Streptococcus pneumoniae

<400> SEQUENCE: 18

Thr Glu Asn Glu Gly Thr Thr Gln Ala Pro Thr Ser Ser Asn Arg Gly
  1               5                  10                  15

Asn Glu Ser Gln Ala Glu His Met Lys Ala Ala Lys Gln Val Asp Glu
             20                  25                  30

Tyr Ile Glu Lys Met Leu Gln Leu Asp Arg Arg Lys His Thr Gln Asn
         35                  40                  45

Val Gly Leu Leu Thr Lys Leu Gly Ala Ile Lys Thr Glu Tyr Leu Arg
     50                  55                  60

Gly Leu Ser Val Ser Lys Glu Lys Ser Thr Ala Glu Leu Pro Ser Glu
 65                  70                  75                  80

Ile Lys Glu Lys Leu Thr Ala Ala Phe Lys Gln Phe Lys Lys Asp Thr
                 85                  90                  95

Leu Lys Pro Glu Lys Lys Val Ala Glu Ala Glu Lys Lys Val Ala Glu
            100                 105                 110

Ala Lys Lys Lys Ala Glu Asp Gln Lys Glu Glu Asp Arg Arg Asn Tyr
        115                 120                 125

Pro Thr Ile Thr Tyr Lys Thr Leu Glu Leu Glu Ile Ala Glu Ser Asp
130                 135                 140

Val Glu Val Lys Lys Ala Glu Leu Glu Leu Val Lys Val Lys Ala Asn
145                 150                 155                 160

Glu Pro Arg Asp Glu Glu Lys Ile Lys Gln Ala Glu Ala Glu Val Glu
                165                 170                 175

Ser Lys Lys Ala Glu Ala Thr Arg Leu Lys Lys Ile Lys Thr Asp Arg
            180                 185                 190

Glu Lys Ala Glu Glu Ala Lys Arg Arg Val Asp Ala Lys Glu Gln
        195                 200                 205

Asp Glu Ser Ser Lys Arg Arg Lys Ser Arg Val Lys Arg Gly Asp Leu
210                 215                 220

Gly Glu Gln Ala Thr Pro Asp Lys Glu Asn Asp Ala Lys Ser Ser
225                 230                 235                 240

Asp Ser Ser Val Gly Glu Glu Thr Leu Pro Ser Pro Ser Leu Lys Pro
                245                 250                 255

Gly Lys Lys Val Ala Glu Ala Glu Lys Lys Val Glu Glu Ala Asp Lys

```
                    260                 265                 270
Lys Ala Lys Ala Gln Lys Glu Glu Asp Arg Arg Asn Tyr Pro Thr Asn
            275                 280                 285

Thr Tyr Lys Thr Leu Glu Leu Glu Ile Ala Glu Ser Asp Val Glu Val
        290                 295                 300

Lys Lys Ala Glu Leu Glu Leu Val Lys Glu Glu Ala Lys Glu Pro Arg
305                 310                 315                 320

Asn Glu Glu Lys Val Lys Gln Ala Lys Ala Glu Val Glu Ser Lys Lys
                325                 330                 335

Ala Glu Ala Thr Arg Leu Glu Lys Ile Lys Thr Asp Arg Lys Lys Ala
            340                 345                 350

Glu Glu Glu Ala Lys Arg Lys Ala Ala Glu Glu Asp Lys Val Lys Glu
        355                 360                 365

Lys Pro Ala Glu Gln Pro Lys Pro Ala Pro Ala Pro Gln Pro Glu Lys
370                 375                 380

Pro Ala Pro Lys Pro Glu Asn Pro Ala Glu Gln Pro Lys Ala Glu Lys
385                 390                 395                 400

Pro Ala Asp Gln Gln Ala
            405

<210> SEQ ID NO 19
<211> LENGTH: 114
<212> TYPE: PRT
<213> ORGANISM: Streptococcus pneumoniae

<400> SEQUENCE: 19

Lys Lys Val Ala Glu Ala Glu Lys Lys Val Glu Glu Ala Lys Lys Lys
1               5                   10                  15

Ala Glu Asp Gln Lys Glu Glu Asp Arg Arg Asn Tyr Pro Thr Asn Thr
            20                  25                  30

Tyr Lys Thr Leu Glu Leu Glu Ile Ala Glu Ser Asp Val Glu Val Lys
        35                  40                  45

Lys Ala Glu Leu Glu Leu Val Lys Glu Glu Ala Lys Glu Ser Arg Asn
    50                  55                  60

Glu Glu Lys Ile Lys Gln Ala Lys Ala Lys Val Glu Ser Lys Lys Ala
65                  70                  75                  80

Glu Ala Thr Arg Leu Glu Lys Ile Lys Thr Asp Arg Lys Lys Ala Glu
                85                  90                  95

Glu Glu Ala Lys Arg Lys Ala Ala Glu Glu Asp Lys Val Lys Glu Lys
            100                 105                 110

Pro Ala

<210> SEQ ID NO 20
<211> LENGTH: 1295
<212> TYPE: DNA
<213> ORGANISM: Artificial Sequence
<220> FEATURE:
<223> OTHER INFORMATION: Description of Artificial Sequence:cDNA derived
      from the genome of Streptococcus pneumoniae.

<400> SEQUENCE: 20
acagagaagg aggtaactac cccagtagcc acttcttcta ataaggcaaa taaaagtcag      60
acagaacata tgaaagctgc tgaacaagtc gatgaatata taaacaaaat gatccaatta    120
gataaaagaa aacatacccca aaatctcgcc ttaaacataa agttgagcgc aattaaaacg    180
aagtatttgc gtgaattaaa tgttttagaa gagaagtcga aaaagaaga gttgacgtca      240
```

-continued

```
aaaacaaaaa aagagataga cgcagctttt gagcagttta acaaagatac attgaaacca      300
ggagaaaagg ttgaagaagc tgagaagaag gttgaagaag ctgagaaaaa agccaaggat      360 caaaagaag  aagatcaccg taactaccca accattactt acaaaacgct tgaacttgaa      420
attgctgagt ccgatgtgga agttaaaaaa gcggagcttg aactagtaaa agaggaagct      480
aagggatctc gaaacgagga aaaaattaag aaagcaaaag cggaagttga gagtaaaaaa      540
gctgaggcta caaagttaga agaaatcaag acagaacgta aaaagcaga  agaagaagct      600 aaacgaaaag cagaagcaga agaagaagtt aaaaataaac taagaagcg  gacaaaacga      660 ggagcttttg gagagccagc aacacctgat aaaaagaaa  atgatgcgaa gtcttcagat      720
tctagcgtgg tgaagaaatc ttccaagccc atcctgaaat cagaaaaaaa agtagcagaa      780
gctgagaaga aggttgcaga agctgagaag aaggttgcag aagctgagaa aaaagccaag      840
gatcaaaaag aagaagatcg ccgtaactac ccaaccaata cttacaaaac gcttgaactt      900
gaaattgctg agtccgatgt gaaagttaaa gaagcggagc ttgaactagt aaaagaggaa      960
gctaaggaac ctcaaaacga ggaaaaaatt aagcaagcaa aagcgaaagt tgagagtaaa     1020
aaagctgagg ctacaaggtt agaaaaaatc aagacagatc gtaaaaaagc agaagaagct     1080
aaacgaaaag tagcagaaga agataaagtt aagaaaaaac cagctgaaca accacaacca     1140
gctcctgcac caaaaccagc gccggctcct caaccagaaa aaccagctga acaaccaaaa     1200
gcagaaaaac cagctgatca acaagctgaa gaagactatg ctcgtagatc agaagaagaa     1260 tataaccegc ttgacttaac agcaccggca aaagc                                1295
```

<210> SEQ ID NO 21
<211> LENGTH: 754
<212> TYPE: DNA
<213> ORGANISM: Artificial Sequence
<220> FEATURE:
<223> OTHER INFORMATION: Description of Artificial Sequence:cDNA derived
      from the genome of Streptococcus pneumoniae

<400> SEQUENCE: 21

```
acagagaacg agggaagtac ccaagcagcc acttcttcta atatggcaaa gacagaacat       60
aggaaagctg ctaaacaagt cgtcgatgaa tatatagaaa aaatgttggg gagattcaac      120
tagatagaag aaaacatacc caaaatgtcg ccttaaacat aaagttgagc gcaattaaaa      180
cgaagtattt gcgtgaatta aatgttttag aagagaagtc gaaagatgag ttgccgtcag      240
aaataaaagc aaagttagac gcagcttttg agaagtttaa aaaagataca ttgaaaccag      300
gagaaaaggt agcagaagct aagaagaagg ttgaagaagc taagaaaaaa gccgaggatc      360
aaaaagaaga agatcgtcgt aactacccaa ccaatactta caaaacgctt gaacttgaaa      420
ttgctgagtt cgatgtgaaa gttaaagaag cggagcttga actagtaaaa gaggaagcta      480
aagaatctcg aaacgagggc acaattaagc aagcaaaaga gaagttgag  agtaaaaaag      540 ctgaggctac aaggttagaa acatcaaga  cagatcgtaa aaaagcagaa gaagaagcta      600
aacgaaaagc agcagaagaa gataaagtta agaaaaaacc agctgaacaa ccacaaccag      660
cgccggctac tcaaccagaa aaaccagctc aaaaccagag aagccagct  gaacaaccaa      720 aagcagaaaa aacagatgat caacaagctg aaga                                  754
```

<210> SEQ ID NO 22
<211> LENGTH: 1239
<212> TYPE: DNA
<213> ORGANISM: Artificial Sequence
<220> FEATURE:

<223> OTHER INFORMATION: Description of Artificial Sequence:cDNA derived
      from the genome of Streptococcus pneumoniae.

<400> SEQUENCE: 22

| | | | | | | |
|---|---|---|---|---|---|---|
| acagagaagg | aggtaactac | ccaagtaccc | acttattcta | atatggcaaa | gacagaacat | 60 |
| aggaaagctg | ctaaacaagt | cgtcgatgaa | tatatagaaa | aaatgttgag | ggagattcaa | 120 |
| ttagatagaa | gaaaacatac | ccaaaatttc | gccttcaaca | tgaagttgag | cgcaattaaa | 180 |
| acggagtatt | tgtatggatt | aaaagagaag | tcggaagctg | agttgccgtc | agaagtaaaa | 240 |
| gcaaagttag | acgcagcttt | tgagcagttt | aaaaaagata | cattgaaact | aggagaaaag | 300 |
| gtagcagaag | ctgagaagaa | ggttgcagaa | gctgagaaaa | agccaaggc | tcaaaagaa | 360 |
| gaagatcgcc | gtaactaccc | aaccaatact | tacaaaacgc | ttgaacttga | aattgctgag | 420 |
| tccgatgtgg | aagttaaaaa | agcggagctt | gaactattga | agaggaagc | taaaactcga | 480 |
| aacgaggaca | caattaacca | agcaaaagcg | aagttgaga | gtaaaaagc | tgaggctaca | 540 |
| aagttagaag | aaatcaagac | agatcgtaaa | aagcagaag | aagaagctaa | acgaaaagca | 600 |
| gaagcagaag | aagataaagt | taagataaa | ctaagagagc | ggacaaaacg | agcagttcct | 660 |
| ggagagccag | caacacctga | taaaaagaa | aatgatgcga | agtcttcaga | ttctagcgta | 720 |
| ggtgaagaaa | ctcttccaag | cccatccctg | aaatcaggaa | aaaaggtagc | agaagctgag | 780 |
| aagaaggttg | cagaagctga | gaaaaagcc | aaggatcaaa | agaagaaga | tcgccgtaac | 840 |
| tacccaacca | atacttacaa | aacgcttgac | cttgaaattg | ctgagtccga | tgtgaaagtt | 900 |
| aaagaagcgg | agcttgaact | agtaaagag | gaagctaagg | gatctcgaaa | cgaggaaaaa | 960 |
| attaaccaag | caaaagcgga | agttgagagt | aaaaagctg | aggctacaag | gctagaaaaa | 1020 |
| atcaagacag | atcgtaaaaa | agcagaagaa | gaagctaaac | gaaaagcagc | agaagaagat | 1080 |
| aaagttaaag | aaaaaccagc | tgaacaacca | caaccagcgc | cggctcctca | accagaaaaa | 1140 |
| ccaactgaag | agcctgagaa | tccagctcca | gctccaaaac | cagagaagcc | agctgaacaa | 1200 |
| ccaaaagcag | aaaaaacaga | tgatcaacaa | gctgaagaa | | | 1239 |

<210> SEQ ID NO 23
<211> LENGTH: 1338
<212> TYPE: DNA
<213> ORGANISM: Artificial Sequence
<220> FEATURE:
<223> OTHER INFORMATION: Description of Artificial Sequence:cDNA derived
      from the genome of Streptococcus pneumoniae

<400> SEQUENCE: 23

| | | | | | | |
|---|---|---|---|---|---|---|
| acagagaacg | agggagctac | ccaagtaccc | acttcttcta | atagggcaaa | tgaaagtcag | 60 |
| gcagaacaag | gagaacaacc | taaaaaactc | gattcagaac | gagataaggc | aaggaaagag | 120 |
| gtcgaggaat | atgtaaaaaa | aatagtgggt | gagagctatg | caaatcaac | taaaaagcga | 180 |
| catacaatta | ctgtagctct | agttaacgag | ttgaacaaca | ttaagaacga | gtatttgaat | 240 |
| aaaatagttg | aatcaacctc | agaaagccaa | ctacagatac | tgatgatgga | gagtcgatca | 300 |
| aaagtagatg | aagctgtgtc | taagtttgaa | aaggactcat | cttcttcgtc | aagttcagac | 360 |
| tcttccacta | aaccggaagc | ttcagataca | gcgaagccaa | acaagccgac | agaaccagga | 420 |
| gaaaaggtag | cagaagctaa | gaagaaggtt | gaagaagttg | agaaaaaagc | caaggatcaa | 480 |
| aaagaagaag | atcgtcgtaa | ctacccaacc | aattacttac | aaacgcttga | acttgaaatt | 540 |
| gctgagtccg | atgtgaaagt | taaaaagcg | gagcttgaac | tagtaaaagt | gaaagctaac | 600 |
| gaacctcgag | acaagcaaaa | aattaagcaa | gcagaagcgg | aagttgagag | taaacaagct | 660 |

```
gaggctacaa ggttaaaaaa aatcaagaca gatcgtgaag aagcagaaga agaagctaaa      720
cgaagagcag atgctaaaga gcaaggtaaa ccaaaggggc ggccaaaacg aggagttcct      780
ggagagctag caacacctga taaaaaagaa aatgatgcga agtcttcaga ttctagcgta      840
ggtgaagaaa ctcttccaag cccatccctg aaaccagaaa aaaaggtagc agaagctgag      900
aagaaggttg aagaagctaa gaaaaaagcc gaggatcaaa agaagaaga tcgccgtaac       960 tacccaacca atacttacaa aacgcttgaa cttgaaattg ctgagtccga tgtggaagtt     1020
aaaaaagcgg agcttgaact agtaaaagag gaagctaagg aacctcgaaa cgaggaaaaa     1080
gttaagcaag caaaagcgga agttgagagt aaaaaagctg aggctacaag gttagaaaaa     1140
atcaagacag atcgtaaaaa agcagaagaa gaagctaaac gaaaagcagc agaagaagat     1200
aaagttaaag aaaaaccagc tgaacaacca caaccagcgc cggctccaaa aacagaaaaa     1260
ccagctccag ctccaaaacc agagaatcca gctgaacaac caaaagcaga aaaaccagct     1320
gatcaacaag ctgaagaa                                                    1338
```

<210> SEQ ID NO 24
<211> LENGTH: 1284
<212> TYPE: DNA
<213> ORGANISM: Artificial Sequence
<220> FEATURE:
<223> OTHER INFORMATION: Description of Artificial Sequence:cDNA derived
      from the genome of Streptococcus pneumoniae

<400> SEQUENCE: 24

```
gaagggggtta gaagtgggaa taactccacg gttacatcta gtgggcaaga tatatcgaag       60
aagtatgctg atgaagtcga gtcgcatcta caaagtatat tgaaggatgt caataaaaat      120
ttgaagaaag ttcaacatac ccaaaatgcc gacttcaaca aaaagttgag caaaattaaa      180
acgaagtatt tgtatgaatt aaatgtttta gaagagaagt cggaagctga gttgacgtca      240
aaaacaaaag aaacaaaaga agagttaacc gcagcttttg agcagtttaa aaaagataca      300
ttatcaacag aaccagaaaa aaggtagca gaagctaaga agaaggttga agaagctaag      360
aaaaaagccg aggatcaaaa agaaaaagat cgccgtaact acccaaccat tacttacaaa      420
acgcttgaac ttgaaattgc tgagtccgat gtggaagtta aaaaagcgga gcttgaacta      480
gtaaaagtga agctaacga acctcgagac gaggaaaaaa ttaagcaagc agaagcgaaa      540
gttgagagta acaagctga ggctacaagg ttaaaaaaaa tcaagacaga tcgtgaacaa      600
gctgaggcta caaggttaga aaacatcaag acagatcgtg aacaagcaga agaagaagct      660
aaagttaaag atgaaccaaa gaagcggaca aaacgaggag ttcttggaga gccagcaaca      720
cctgataaaa aagaaaatga tgcgaagtct tcagattcta gcgtaggtga agaaactctt      780
ccaagcccat ccctgaaacc agaaaaaaag gttgcagaag ctgagaagaa ggttgaagaa      840
gctaagaaaa aagccgagga tcaaaagaa gaagatcgtc gtaactaccc aaccaatact       900
tacaaaacgc ttgaacttga aattgctgag tccgatgtgg aagttaaaaa agcggagctt      960
gaactagtaa aagaggaagc taaggaacct cgaaacgagg aaaaagttaa gcaagcaaaa     1020
gcggaagttg agagtaaaca agctgaggct acaaggttag aaaacatcaa gacagatcgt     1080
aaaaaagcag aagaagaagc taaacgaaaa gcagcagaag aagataaagt taagaaaaaa     1140
ccagctgaac aaccacaacc agcgccggct cctcaaccag aaaaaccagc tccaaaacca     1200
gaaaaaccag ctccagctcc aaaaccagag aatccagctg aacaaccaaa agcagaaaaa     1260
ccagctgatc aacaagctga agaa                                            1284
```

<210> SEQ ID NO 25
<211> LENGTH: 658
<212> TYPE: DNA
<213> ORGANISM: Artificial Sequence
<220> FEATURE:
<223> OTHER INFORMATION: Description of Artificial Sequence:cDNA derived
      from the genome of Streptococcus pneumoniae

<400> SEQUENCE: 25

```
gaagggggtta gaagtgggaa taactccacg gttacatcta gtgggcaaga tatatcgaag      60
aagtatgctg atgaagtcga gtcgcatcta caaagtatat tgaaggatgt caataaaaat     120
ttgaaaaaag ttcaacatac ccaaaatgcc gacttcaaca aaaagttgag caaaattaaa     180
ccgaagtatt tgtatgaatt aaagtgttta gaagagaagt cggaagctga gttgacgtca     240
aaaccaaaga acaaaagaag agttaccgca gctttttgagc agtttaaaaa agatacatta    300
tcaacagaac cagaaaaaaa ggtagcagaa gctaagaaga aggttgaaga agctaagaaa     360
aaagccgagg atcaaaaaga aaagatcgc cgtaactacc caaccattac ttacaaaacg      420
cttgaacttg aaattgctga gtccgatgtg gaagttaaaa aagcggagct tgaactagta     480
aaagaggaag ctaaggaacc tcgaaacgag gaaaaagtta agcaagcaaa agcggaagtt     540
gagagtaaac aagctgaggc tacaaggtta gaaaaaatca gacagatcg taaaaaagca     600 gaagaagaag ctaaacgaaa agcagcagaa gaagataaag ttaaagaaaa accagctg      658
```

<210> SEQ ID NO 26
<211> LENGTH: 1338
<212> TYPE: DNA
<213> ORGANISM: Artificial Sequence
<220> FEATURE:
<223> OTHER INFORMATION: Description of Artificial Sequence:cDNA derived
      from the genome of Streptococcus pneumoniae

<400> SEQUENCE: 26

```
acagagaacg agggagctac ccaagtaccc acttcttcta ataggggcaaa tgaaagtcag     60 gcagaacaag gagaacaacc taaaaaactc gattcagaac gagataaggc aaggaaagag    120
gtcgaggaat atgtaaaaaa aatagtgggt gagagctatg caaatcaac taaaaagcga     180 catacaatta ctgtagctct agttaacgag ttgaacaaca ttaagaacga gtatttgaat    240
aaaatagttg aatcaacctc agaaagccaa ctacagatac tgatgatgga gagtcgatca    300
aaagtagatg aagctgtgtc taagtttgaa aaggactcat cttcttcgtc aagttcagac    360
tcttccacta aaccggaagc ttcagataca gcgaagccaa acaagccgac agaaccagga    420
gaaaaggtag cagaagctaa gaagaaggtt gaagaagctg agaaaaaagc caaggatcaa    480
aaagaagaag atcgtcgtaa ctacccaacc attacttaca aaacgcttga acttgaaatt    540
gctgagtccg atgtggaagt taaaaaagcg gagcttgaac tagtaaaagt gaaagctaac    600
gaacctcgag acgagcaaaa aattaagcaa gcagaagcgg aagttgagag taaacaagct    660
gaggctacaa ggttaaaaaa aatcaagaca gatcgtgaag aagcagaaga gaagctaaa    720 cgaagagcag atgctaaaga gcaaggtaaa ccaagggggc gggcaaaacg aggagttcct    780
ggagagctag caacacctga taaaaagaa atgatgcga agtcttcaga ttctagcgta     840
ggtgaagaaa ctcttccaag cccatccctg aaaccagaaa aaaggtagc agaagctgag    900 aagaaggttg aagaagctaa gaaaaaagcc gaggatcaaa aagaagaaga tcgccgtaac    960
tacccaacca atacttacaa aacgcttgaa cttgaaattg ctgagtccga tgtggaagtt   1020
```

-continued

```
aaaaaagcgg agcttgaact agtaaaagag gaagctaagg aacctcgaaa cgaggaaaaa    1080
gttaagcaag caaaagcgga agttgagagt aaaaaagctg aggctacaag gttagaaaaa    1140
atcaagacag atcgtaaaaa agcagaagaa gaagctaaac gaaaagcagc agaagaagat    1200
aaagttaaag aaaaaccagc tgaacaacca caaccagcgc cggctccaaa agcagaaaaa    1260
ccagctccag ctccaaaacc agagaatcca gctgaacaac caaaagcaga aaaccagct    1320 gatcaacaag ctgaagaa                                                   1338
```

<210> SEQ ID NO 27
<211> LENGTH: 1242
<212> TYPE: DNA
<213> ORGANISM: Artificial Sequence
<220> FEATURE:
<223> OTHER INFORMATION: Description of Artificial Sequence:cDNA derived
      from the genome of Streptococcus pneumoniae

<400> SEQUENCE: 27

```
acagaaaacg aaggaagtac ccaagcagcc acttcttcta atatggcaaa gacagaacat      60
aggaaagctg ctaaacaagt cgtcgatgaa tatatagaaa aatgttgag ggagattcaa      120 ctagatagaa gaaaacatac ccaaaatgtc gccttaaaca taaagttgag cgcaattaaa    180
acgaagtatt tgcgtgaatt aaatgtttta gaagagaagt cgaaagatga gttgccgtca    240
gaaataaaag caaagttaga cgcagctttt gagaagttta aaaagatac attgaaacca    300 ggagaaaagg tagcagaagc taagaagaag gttgaagaag ctaagaaaaa agccgaggat    360
caaaaagaag aagatcgtcg taactaccca accaatactt acaaaacgct tgaacttgaa    420
attgctgagt tcgatgtgaa agttaaagaa gcggagcttg aactagtaaa agaggaagct    480
aaagaatctc gaaacgaggg cacaattaag caagcaaaag agaaagttga gagtaaaaaa    540
gctgaggcta caaggttaga aaacatcaag acagatcgta aaaagcaga gaagaagct    600 aaacgaaaag cagatgctaa gttgaaggaa gctaatgtag cgacttcaga tcaaggtaaa    660 ccaaggggc gggcaaaacg aggagttcct ggagagctag caacacctga taaaaaagaa    720
aatgatgcga agtcttcaga ttctagcgta ggtgaagaaa ctcttccaag ctcatccctg    780
aaatcaggaa aaaaggtagc agaagctgag aagaaggttg aagaagctga gaaaaaagcc    840
aaggatcaaa aagaagaaga tcgccgtaac tacccaacca atacttacaa aacgcttgac    900
cttgaaattg ctgagtccga tgtgaaagtt aaagaagcgg agcttgaact agtaaaagag    960
gaagctaagg aacctcgaga cgaggaaaaa attaagcaag caaaagcgaa agttgagagt   1020
aaaaaagctg aggctacaag gttagaaaac atcaagacag atcgtaaaaa agcagaagaa   1080
gaagctaaac gaaaagcagc agaagaagat aaagttaaag aaaaaccagc tgaacaacca   1140
caaccagcgc cggctactca accagaaaaa ccagctccaa aaccagagaa gccagctgaa   1200
caaccaaaag cagaaaaaac agatgatcaa caagctgaag aa                       1242
```

<210> SEQ ID NO 28
<211> LENGTH: 1275
<212> TYPE: DNA
<213> ORGANISM: Artificial Sequence
<220> FEATURE:
<223> OTHER INFORMATION: Description of Artificial Sequence:cDNA derived
      from the genome of Streptococcus pneumoniae

<400> SEQUENCE: 28

```
acagagaagg aggtaactac ccaagtagcc acttcttcta ataggcaaa tgaaagtcag      60 gcaggacata ggaaagctgc tgaacaattc gatgaatata taaaaacaat gatccaatta    120
```

```
gatagaagaa acatacccca aaatttcgcc ttaaacataa agttgagcag aattaaaacg      180
gagtatttgc gtaaattaaa tgttttagaa gagaagtcga aagctgagtt gccgtcagaa      240
acaaaaaaag agatagacgc agcttttgag cagtttaaaa aagataccaa cagaaccaaa      300
aaaacggtag cagaagctga gaagaaggtt gaagaagcta agaaaaaagc caaggctcaa      360
aaagaagaag atcaccgtaa ctacccaacc aatacttaca aaacgcttga acttgaaatt      420
gctgagtccg atgtggaagt taaaaaagcg gagcttgaac tagtaaaaga ggaagctaag      480
gaatctcgag acgatgaaaa aattaagcaa gcagaagcga aagttgagag taaaaaagct      540
gaggctacaa ggttagaaaa catcaagaca gatcgtgaaa aagcagaaga agaagctaaa      600
cgaagagcag aagctaagtt gaaggaagct gttgaaaaga atgtagcgac ttcagagcaa      660
gataaaccaa aggggcggag aaaacgagga gttcctggag agcaagcaac acctgataaa      720
aaagaaaatg atgcgaagtc ttcagattct agcgtaggtg aagaagctct tccaagccca      780
tccctgaaac agaaaaaaaa ggttgcagaa gctgagaaga aggttgcaga agctgagaaa      840
aaagccaagg ctcaaaaaga agaagatcgc cgtaactacc caaccaatac ttacaaaacg      900
cttgaacttg aaattgctga gtccgatgtg aaagttaaag aagcggagct tgaactagta      960
aaagaggaag ctaaggaatc tcgaaacgag gaaaaagtta atcaagcaaa agcgaaagtt     1020
gagagtaaaa aagctgaggc tacaaggtta gaaaaaatca agacagatcg taaaaaagca     1080
gaagaagaag ctaaacgaaa agcagcagaa gaagataaag ttaagaaaaa accagctgaa     1140
caaccacaac cagcgccggc tcctcaacca gaaaaaccaa ctgaagagcc tgagaatcca     1200
gctcccgcac caaaaccaga gaagccagct gaacaaccaa aagcagaaaa aacagatgat     1260
caacaagctg aagaa                                                     1275
```

<210> SEQ ID NO 29
<211> LENGTH: 1278
<212> TYPE: DNA
<213> ORGANISM: Artificial Sequence
<220> FEATURE:
<223> OTHER INFORMATION: Description of Artificial Sequence: cDNA derived
      from the genome of Streptococcus pneumoniae

<400> SEQUENCE: 29

```
acagagaagg aggtaactac ccaagtagcc acttcttcta ataaggcaaa taaaagtcag       60
acagaacata tgaaagctgc taaacaagtc gatgaatata taaaaaaaaa gctccaatta      120
gatagaagaa acatacccca aaatgtcggc ttactcacaa agttgggcgt aattaaaacg      180
gagtatttgc atggattaag tgtttcaaaa agaagtcgg aagctgagtt gccgtcagaa       240
ataaaagcaa agttagacgc agcttttgag cagtttaaaa aagatacatt accaacagaa      300
ccaggaaaaa aggtagcaga agctgagaag aaggttgaag aagctaagaa aaaagccgag      360
gatcaaaaag aaaaagatct ccgtaactac ccaaccaata cttacaaaac gcttgaactt      420
gacattgctg agtccgatgt ggaagttaaa aaagcggagc ttgaactagt aaaagaggaa      480
gctaaggaat ctcgagacga gaaaaaaatt aatcaagcaa aagcgaaagt tgagaataaa      540
aaagctgagg ctacaaggtt aaaaaacatc aagacagatc gtgaaaaagc agaagaagct      600
aaacgaagag cagatgctaa gttgcaggaa gctaatgtag cgacttcaga gcaagataaa      660
tcaaagaggc gggcaaaacg agaagttctt ggagagctag caacacctga taaaaaagaa      720
aatgatgcga agtcttcaga ttctagcgta ggtgaagaaa ctcttacaag cccatccctg      780
aaaccagaaa aaaaggtagc agaagctgag aagaaggttg aagaagctaa gaaaaaagcc      840
```

```
gaggatcaaa aagaagaaga tcgtcgtaac tacccaacca atacttacaa aacgcttgaa      900
cttgaaattg ctgagtccga tgtggaagtt aaaaaagcgg agcttgaact agtaaaagag      960
gaagctaagg aatctcgaaa cgaggaaaaa attaagcaag taaaagcgaa agttgagagt     1020 aaaaagctg aggctacaag gctagaaaac atcaagacag atcgtaaaaa agcagaagaa     1080
gaagaagcta acgaagagc agcagaagaa gataaagtta agaaaaaacc agctgaacaa      1140
ccacaaccag cgccggctcc tcaaccagaa aaaccaactg aagagcctga gaatccagct     1200
ccagctccag ctccaaaacc agagaatcca gctgaaaaac caaaagcaga aaagccagct     1260
gatcaacaag ctgaagaa                                                    1278
```

<210> SEQ ID NO 30
<211> LENGTH: 1276
<212> TYPE: DNA
<213> ORGANISM: Artificial Sequence
<220> FEATURE:
<223> OTHER INFORMATION: Description of Artificial Sequence:cDNA derived
      from the genome of Streptococcus pneumoniae

<400> SEQUENCE: 30

```
acagagaagg aggtaactac ccaagtagcc acttcttcta ataaggcaaa taaaagtcag       60
acagaacata tgaaagctgc taaacaagtc gatgaatata taaaaaaaaa gctccaatta      120
gatagaagaa aacatacccca aaatgtcggc ttactcacaa agttgggcgt aattaaaacg     180
gagtatttgc atggattaag tgtttcaaaa aagaagtcgg aagctgagtt gccgtcagaa      240
ataaaagcaa agttagacgc agcttttgag cagtttaaaa aagatacatt accaacagaa      300
ccaggaaaaa aggtagcaga agctgagaag aaggttgaag aagctaagaa aaaagccgag      360
gatcaaaaag aaaagatct ccgtaactac ccaaccaata cttacaaaac gcttgaactt       420
gacattgctg agtccgatgt ggaagttaaa aaagcggagc ttgaactagt aaagaggaa       480 gctaaggaat ctcgagacga aaaaaatt aatcaagcaa agcgaaagt tgagaataaa         540 aaagctgagc tacaaggtt aaaaaacatc aagacagatc gtgaaaaagc agaagaagct      600
aaacgaagag cagatgctaa gttgcaggaa gctaatgtag cgacttcaga gcaagataaa     660
tcaaagaggc gggcaaaacg agaagttttt ggagagctag caacacctga taaaaagaa      720 aatgatgcga agtcttcaga ttctagcgta ggtgaagaaa ctcttacaag cccatccctg     780
aaaccagaaa aaaaggtagc agaagctgag aagaaggttg aagaagctaa gaaaaaagcc      840
gaggatcaaa aagaagaaga tcgtcgtaac tacccaacca atacttacaa aacgcttgaa     900
cttgaaattg ctgagtccga tgtggaagtt aaaaaagcgg agcttgaact agtaaaagag     960
gaagctaagg aatctcgaaa cgaggaaaaa attaagcaag taaaagcgaa agttgagagt    1020 aaaaagctg aggctacaag gctagaaaac atcaagacag atcgtaaaaa agcagaagaa    1080
gaagaagcta acgaagagc agcagaagaa gataaagtta agaaaaaacc agctgaacaa     1140
ccacaaccag cgccggctcc tcaaccagaa aaaccaactg aagagcctga gaatccagct    1200
ccagctccag ctccaaaacc agagaatcca gctgaaaaac caaaagcaga aaagccagct    1260
gatcaacaag ctgaag                                                    1276
```

<210> SEQ ID NO 31
<211> LENGTH: 1272
<212> TYPE: DNA
<213> ORGANISM: Artificial Sequence
<220> FEATURE:
<223> OTHER INFORMATION: Description of Artificial Sequence:cDNA derived -continued from the genome of Streptococcus pneumoniae

<400> SEQUENCE: 31

| | | | | | |
|---|---|---|---|---|---|
| acagagaagg | aggtaactac | ccaagtagcc | acttcttcta | atagggcaaa | taaaagtcag | 60 |
| acagaacata | tgaaagctgc | taaacaagtc | gatgaatata | taaaaaaaaa | gctccaatta | 120 |
| gatagaagaa | acatacccca | aaatgtcggc | ttactcacaa | agttgggcgt | aattaaaacg | 180 |
| gagtatttgc | atggattaag | tgtttcaaaa | agaagtcgg | aagctgagtt | gccgtcagaa | 240 |
| ataaaagcaa | agttagacgc | agcttttgag | cagtttaaaa | aagatacatt | accaacagaa | 300 |
| ccaggtaaaa | aggtagcaga | agctgagaag | aaggttgaag | aagctaagaa | aaaagccgag | 360 |
| gatcaaaaag | aaaagatct | ccgtaactac | ccaaccaata | cttacaaaac | gcttgaactt | 420 |
| gacattgctg | agtccgatgt | ggaagttaaa | aaagcggagc | ttgaactagt | aaaagaggaa | 480 |
| gctaaggaat | ctcgagacga | gaaaaaaatt | aatcaagcaa | aagcgaaagt | tgagaataaa | 540 |
| aaagctgagg | ctacaaggtt | aaaaaacatc | aagacagatc | gtgaaaaagc | agaagaagct | 600 |
| aaacgaagag | cagatgctaa | gttgcaggaa | gctaatgtag | cgacttcaga | gcaagataaa | 660 |
| tcaaagaggc | gggcaaaacg | agaagttctt | ggagagctag | caacacctga | taaaaaagaa | 720 |
| aatgatgcga | agtcttcaga | ttctagcgta | ggtgaagaaa | ctcttacaag | cccatccctg | 780 |
| aaaccagaaa | aaaaggtagc | agaagctgag | aagaaggttg | aagaagctaa | gaaaaaagcc | 840 |
| gaggatcaaa | aagaagaaga | tcgtcgtaac | tacccaacca | atacttacaa | aacgcttgaa | 900 |
| cttgaaattg | ctgagtccga | tgtggaagtt | aaaaaagcgg | agcttgaact | agtaaaagag | 960 |
| gaagctaagg | aatctcgaaa | cgaggaaaaa | attaagcaag | taaaagcgaa | agttgagagt | 1020 |
| aaaaaagctg | aggctacaag | gctagaaaac | atcaagacag | atcgtaaaaa | agcagaagaa | 1080 |
| gaagaagcta | aacgaagagc | agcagaagaa | gataaagtta | agaaaaaacc | agctgaacaa | 1140 |
| ccacaaccag | cgccggctcc | tcaaccagaa | aaaccaactg | aagagcctga | gaatccagct | 1200 |
| ccagctccag | ctccaaaacc | agagaatcca | gctgaaaaac | aaaagcaga | aaagccagct | 1260 |
| gatcaacaag | ct | | | | | 1272 |

<210> SEQ ID NO 32
<211> LENGTH: 1258
<212> TYPE: DNA
<213> ORGANISM: Artificial Sequence
<220> FEATURE:
<223> OTHER INFORMATION: Description of Artificial Sequence:cDNA derived
from the genome of Streptococcus pneumoniae

<400> SEQUENCE: 32

| | | | | | |
|---|---|---|---|---|---|
| acagagaacg | agagaactac | ccaagtaccc | acttcttcta | ataggggaaa | gccagaacgt | 60 |
| aggaaagctg | ctgaacaatt | cgatgaatat | ataaacaaaa | tgatccaatt | agataaaaga | 120 |
| aaacatacccc | aaaatttagc | cttcaacata | cagttgagca | gaattaaaac | ggagtatttg | 180 |
| aatggattaa | agagaagtc | ggaagctgag | ttgccgtcaa | aataaaagc | agagttagac | 240 |
| gcagcttta | agcagtttaa | aaaagataca | ttaccaacaa | accagaaaa | aaagtagca | 300 |
| gaagctgaga | agaaggttga | agaagctgag | aagaggtag | cagaagctaa | gaaaaaagcc | 360 |
| aaggctcaaa | aagaagaaga | tcaccgtaac | tacccaacca | ttacttacaa | aacgcttgac | 420 |
| cttgaaattg | ctgagttcga | tgtgaaagtt | aaagaagcgg | agcttgaact | agtaaaaaag | 480 |
| gaagctgacg | aatctcgaaa | cgagggcaca | attaaccaag | caaagcgaa | agttgagagt | 540 |
| gaaaaagctg | aggctacaag | gttaaaaaaa | atcaagacag | atcgtgaaaa | agcagaagaa | 600 |

| | |
|---|---|
| gaagaagcta aacgaagagc agatgctaaa gagcaagatg aatcaaagag gcgaaagagt | 660 |
| cggggaaaac gaggagctct tggagagcaa gcaacacctg ataaaaaga aaatgatgcg | 720 |
| aagtcttcag attctagcgt aggtgaagaa actcttccaa gcccatccct gaaaccagga | 780 |
| aaaaaggtag cagaagctga gaagaaggtt gaagaagctg ataaaaagc caaggctcaa | 840 |
| aaagaagaag atcgccgtaa ctacccaacc aatacttaca aaacgcttga acttgaaatt | 900 |
| gctgagtccg atgtgaaagt taagaagcg gagcttgaac tagtaaaaga ggaagctaag | 960 |
| gaatctcgaa acgaggaaaa aattaagcaa gcaaaagcga aagttgagag taaaaaagct | 1020 |
| gaggctacaa ggttagaaaa aatcaagaca gatcgtaaaa aagcagaaga agaagctaaa | 1080 |
| cgaaaagcag cagaagaaga taagttaaaa gaaaaaccag ctgaacaacc acaaccagcg | 1140 |
| ccggctcctc aaccagaaaa accagctgaa gagcctgaga atccagttcc agctccaaaa | 1200 |
| ccagagaatc cagctgaaca accaaaagca gaaaaaccag ctgatcaaca agctgaag | 1258 |

<210> SEQ ID NO 33
<211> LENGTH: 1242
<212> TYPE: DNA
<213> ORGANISM: Artificial Sequence
<220> FEATURE:
<223> OTHER INFORMATION: Description of Artificial Sequence:cDNA derived
      from the genome Streptococcus pneumoniae

<400> SEQUENCE: 33

| | |
|---|---|
| acagagaacg agggaagtac ccaagcagcc acttcttcta atatggcaaa gacagaacat | 60 |
| aggaaagctg ctaaacaagt cgtcgatgaa tatatagaaa aaatgttgag ggagattcaa | 120 |
| ctagatagaa gaaaacatac ccaaaatgtc gccttaaaca taagttgag cgcaattaaa | 180 |
| acgaagtatt tgcgtgaatt taatgtttta gaagagaagt cgaaggatga gttgccgtca | 240 |
| gaaataaaag caaagttaga cgcagctttt gagaagttta aaaagataca attgaaacca | 300 |
| ggagaaaagg tagcagaagc taagaagaag gttgaagaag ctaagaaaaa agccgaggat | 360 |
| caaaaagaag aagatcgtcg taactaccca accaatactt acaaaacgct tgaacttgaa | 420 |
| attgctgagt cgatgtgaa agttaaagaa gcggagcttg aactagtaaa agaggaagct | 480 |
| aaagaatctc gaaacgaggg cacaattaag caagcaaaag agaaagttga gagtaaaaaa | 540 |
| gctgaggcta caaggttaga aaacatcaag acagatcgta aaaagcaga agaagaagct | 600 |
| aaacgaaaag cagatgctaa gttgaaggaa gctaatgtag cgacttcaga tcaaggtaaa | 660 |
| ccaaggggc gggcaaaacg aggagttcct ggagagctag caacacctga taaaaagaa | 720 |
| aatgatgcga agtcttcaga ttctagcgta ggtgaagaaa ctcttccaag ctcatccctg | 780 |
| aaatcaggaa aaaggtagc agaagctgag aagaaggtta agaagctga gaaaaagcc | 840 |
| aaggatcaaa agaagaaga tcgccgtaac tacccaacca atacttacaa aacgcttgac | 900 |
| cttgaaattg ctgagtccga tgtgaaagtt aagaagcgg agcttgaact agtaaaagag | 960 |
| gaagctaagg aacctcgaga cgaggaaaaa attaagcaag caaaagcgaa agttgagagt | 1020 |
| aaaaaagctg aggctacaag gttagaaaac atcaagacag atcgtaaaaa agcagaagaa | 1080 |
| gaagctaaac gaaaagcagc agaagaagat aagttaaag aaaaaccagc tgaacaacca | 1140 |
| caaccagcgc cggctactca accagaaaaa ccagctccaa accagagaa gccagctgaa | 1200 |
| caaccaaaag cagaaaaaac agatgatcaa caagctgaag aa | 1242 |

<210> SEQ ID NO 34
<211> LENGTH: 1236
<212> TYPE: DNA

<213> ORGANISM: Artificial Sequence
<220> FEATURE:
<223> OTHER INFORMATION: Description of Artificial Sequence:cDNA derived
from the genome Streptococcus pneumoniae

<400> SEQUENCE: 34

```
gaagggctta gaagtgagaa taaccccacg gttacatcta gtgggcaaga tatatcgaag      60
aagtatgctg atgaagtcaa gtcacatcta gaaaaaatat tgagtgagat ccaaacaaat     120
ttagatagaa gtaaacatat caaaactgta aatctaatta acaaattgca agacattaag     180
agaacgtatt tgtatgaatt aaatgtttta gaagataagt cgaaagctga gttgccgtca     240
aaaataaaag cagagttaga cgcagctttt gagcagttta aaaagatac attaccaaca      300 gaaccaggaa aaaaggtagc agaagctaag aagaaggttg aagaagctga gaaaaaagcc     360
aaggctcaaa agaagaaga ttaccgtaac tacccaacca ttacttacaa aacgcttgaa      420
cttgaaattg ctgagtccga tgtgaaagtt aagaagcgg agcttgaact agtaaaaaag      480
gaagctgacg aatctcgaaa cgagggcaca attaaccaag caaaagcgaa agttgagagt     540
gaacaagctg aggctacaag gttaaaaaaa atcaagacga atcgtgaaaa agcagaagaa     600
gaagctaaac gaagagcaga tgctaaagag caagatgaat caagagggcg aaagagtcgg     660
gtaaaacgag gagattttgg agagccagca cacctgata aaaaagaaaa tgatgcgaag      720
tcttcagatt ctagcgtagg tgaagaaact cttccaagcc catccctgaa accaggaaaa     780
aaggtagcag aagctgagaa gaaggttgaa gaagctgaga aaaaagccaa ggatcaaaaa     840
gaagaagatc accgtaacta cccaaccatt acttacaaaa cgcttgaact tgaaattgct     900
gagtccgatg tggaagttaa aaagcggag cttgaactag taaagaggga gctaagggga     960
tctcgaaacg aggaaaaagt taagcaagca aaagcggaag ttgagagtaa aaagctgag     1020 gctacaaggt tagaaaaaat caagacagat cgtaaaaaag cagaagaaga agctaaacga    1080
aaagcagcag aagaagataa agttaaagaa aaaccagctg aacaaccaca accagcgccg    1140
gctcctcaac cagaaaaacc agctccagct ccaaaaccag agaatccagc tgaacaacca    1200
aaagcagaaa aaccagctga tcaacaagct gaagaa                             1236
```

<210> SEQ ID NO 35
<211> LENGTH: 1218
<212> TYPE: DNA
<213> ORGANISM: Artificial Sequence
<220> FEATURE:
<223> OTHER INFORMATION: Description of Artificial Sequence:cDNA derived
from the genome Streptococcus pneumoniae

<400> SEQUENCE: 35

```
acagagaacg agggaactac ccaagcaccc acttcttcta ataggggaaa tgaaagtcag      60
gcagaacata tgaagctgc taaacaagtc gatgaatata tagaaaaaat gctccaatta     120
gatagaagaa aacatacccca aatgtcggc ttactcacaa agttgggcgc aattaaaacg     180
gagtatttgc gtggattaag tgtttcaaaa gagaagtcga cagctgagtt gccgtcagaa     240
ataaaagaaa agttaaccgc agcttttaag cagtttaaaa aagatacatt gaaaccagaa     300
aaaaaggtag cagaagctga agaaggta gcagaagcta agaaaaaagc cgaggatcaa       360
aaagaagaag atcgtcgtaa ctacccaacc attacttaca aaacgcttga acttgaaatt     420
gctgagtccg atgtggaagt taaaaagcg gagcttgaac tagtaaaagt gaaagctaac     480
gaacctcgag acgaggaaaa aattaagcaa gcagaagcgg aagttgagag taaaaaagct    540
gaggctacaa ggttaaaaaa aatcaagaca gatcgtgaaa aagcagaaga agaagctaaa    600
```

```
cgaagagtag atgctaaaga gcaagatgaa tcatcaaaga ggcgaaagag tcgggtaaaa    660
cgaggagatc ttggagagca agcaacacct gataaaaaag aaaatgatgc gaagtcttca    720
gattctagcg taggtgaaga aactcttcca agcccatccc tgaaaccagg aaaaaaggta    780
gcagaagctg agaagaaggt tgaagaagct gataaaaaag ccaaggctca aaagaagaa     840 gatcgccgta actacccaac caatacttac aaaacgcttg aacttgaaat tgctgagtcc    900
gatgtggaag ttaaaaaagc ggagcttgaa ctagtaaaag aggaagctaa ggaacctcga    960
aacgaggaaa aagttaagca agcaaaagcg gaagttgaga gtaaaaaagc tgaggctaca    1020
aggttagaaa aaatcaagac agatcgtaaa aaagcagaag aagaagctaa acgaaaagca    1080
gcagaagaag ataaagttaa agaaaaacca gctgaacaac caaaaccagc gccggctcct    1140
caaccagaaa aaccagctcc aaaaccagag aatccagctg aacaaccaaa agcagaaaaa    1200
ccagctgatc aacaagct                                                 1218
```

<210> SEQ ID NO 36
<211> LENGTH: 102
<212> TYPE: PRT
<213> ORGANISM: Artificial Sequence
<220> FEATURE:
<223> OTHER INFORMATION: Description of Artificial Sequence:Amino acid
      sequence derived from cDNA consensus sequence from the genome of
      Streptococcus pneumoniae

<400> SEQUENCE: 36

```
Thr Glu Asn Glu Gly Thr Thr Gln Val Ala Thr Ser Ser Asn Arg Ala
 1               5                  10                  15

Asn Gln Thr Glu His Arg Lys Ala Ala Lys Gln Val Val Asp Glu Tyr
            20                  25                  30

Ile Lys Lys Met Leu Glu Gln Leu Asp Arg Arg Lys His Thr Gln Asn
        35                  40                  45

Val Ala Leu Asn Ile Lys Leu Ser Ala Ile Lys Thr Glu Tyr Leu Arg
    50                  55                  60

Glu Leu Asn Val Leu Glu Glu Lys Ser Lys Ala Glu Leu Pro Ser Glu
65                  70                  75                  80

Ile Lys Ala Lys Leu Asp Ala Ala Phe Glu Gln Phe Lys Lys Asp Thr
                85                  90                  95

Leu Lys Thr Glu Pro Gly
            100
```

<210> SEQ ID NO 37
<211> LENGTH: 55
<212> TYPE: PRT
<213> ORGANISM: Artificial Sequence
<220> FEATURE:
<223> OTHER INFORMATION: Description of Artificial Sequence:Amino acid
      sequence derived from cDNA consensus sequence from the genome of
      Streptococcus pneumoniae

<400> SEQUENCE: 37

```
Asp Ala Lys Leu Glu Ala Thr Ser Glu Gln Asp Lys Pro Lys Gly Arg
 1               5                  10                  15

Ala Lys Arg Gly Val Pro Gly Leu Ala Thr Pro Asp Lys Lys Glu
            20                  25                  30

Asn Asp Ala Lys Ser Ser Asp Ser Ser Val Gly Glu Glu Thr Leu Pro
        35                  40                  45

Ser Pro Ser Leu Lys Pro Glu
    50                  55
```

```
<210> SEQ ID NO 38
<211> LENGTH: 103
<212> TYPE: PRT
<213> ORGANISM: Artificial Sequence
<220> FEATURE:
<223> OTHER INFORMATION: Description of Artificial Sequence:Amino acid
      sequence derived from cDNA consensus sequence from the genome of
      Streptococcus pneumoniae

<400> SEQUENCE: 38

Lys Lys Val Ala Glu Ala Glu Lys Lys Val Glu Glu Ala Lys Lys Lys
  1               5                  10                  15

Ala Lys Asp Gln Lys Glu Glu Asp Arg Arg Asn Tyr Pro Thr Ile Thr
                 20                  25                  30

Tyr Lys Thr Leu Glu Leu Glu Ile Ala Glu Ser Asp Val Glu Val Lys
             35                  40                  45

Lys Ala Glu Leu Glu Leu Val Lys Glu Glu Ala Lys Glu Ser Arg Asp
         50                  55                  60

Glu Gly Lys Ile Lys Gln Ala Lys Ala Lys Val Glu Ser Lys Lys Ala
 65                  70                  75                  80

Glu Ala Thr Arg Leu Lys Lys Ile Lys Thr Asp Arg Glu Lys Ala Glu
                 85                  90                  95

Glu Glu Ala Lys Arg Arg Ala
                100
```

DERIVATIVES OF CHOLINE BINDING PROTEINS FOR VACCINES

This application claims the benefit of U.S. Prov. Appl'n Serial No.'s 60/085,743, filed May 15, 1998 and 60/080,878 filed Apr. 7, 1998.

This invention relates generally to the field of bacterial antigens and their use, for example, as immunogenic agents in humans and animals to stimulate an immune response. More specifically, it relates to the vaccination of mammalian species with a polypeptide comprising an alpha helix-forming polypeptide obtained from a choline binding polypeptide as a mechanism for stimulating production of antibodies that protect the vaccine recipient against infection by pathogenic bacterial species. Further, the invention relates to antibodies and antagonists against such polypeptides useful in diagnosis and passive immune therapy with respect to diagnosing and treating such pneumococcal infections.

In a particular aspect, the present invention relates to the prevention and treatment of pneumonococcal infections such as infections of the middle ear, nasopharynx, lung and bronchial areas, blood, CSF, and the like, that are caused by pneumonococcal bacteria. In this regard, certain types of *Streptococcus pneumoniae* are of particular interest.

*S. pneumoniae* is a gram positive bacteria which is a major causative agent in invasive infections in animals and humans, such as sepsis, meningitis, otitis media and lobar pneumonia (Tuomanen, et al. NEJM 322:1280–1284 (1995)). As part of the infective process, pneumococci readily bind to non-inflamed human epithelial cells of the upper and lower respiratory tract by binding to eukaryotic carbohydrates in a lectin-like manner (Cundell et al., Micro. Path. 17:361–374 (1994)). Conversion to invasive pneumococcal infections for bound bacteria may involve the local generation of inflammatory factors which may activate the epithelial cells to change the number and type of receptors on their surface (Cundell, et al., Nature, 377:435–438 (1995)). Apparently, one such receptor, platelet activating factor (PAF) is engaged by the pneumococcal bacteria and within a very short period of time (minutes) from the appearance of PAF, pneumococci exhibit strongly enhanced adherence and invasion of tissue. Certain soluble receptor analogs have been shown to prevent the progression of pneumococcal infections (Idanpaan-Heikkila et al., J. Inf. Dis., 176:704–712 (1997)).

A family of choline binding proteins (CBPs), which are non-covalently bound to phosphorylcholine, are present on the surface of pneumococci and have a non-covalent association with teichoic acid or lipoteichoic acid. An example of such family is choline binding protein A (CbpA), an approximately 75 kD weight type of CBP which includes a unique N-terminal domain, a proline rich region, and a C-terminal domain comprised of multiple 20 amino acid repeats responsible for binding to choline. A segment of the N-terminal portion of CbpA protein forms an alpha helix as part of its three-dimensional structure.

Accordingly, it is an object of the present invention to provide a polypeptide having broad protection against pneumococcal infections.

DEFINITIONS

In order to facilitate understanding of the description below and the examples which follow certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

"HPS portion" as used herein refers to an amino acid sequence as set forth in SEQ ID NO:2 for a choline binding protein ("CBP") of a pneumococcal bacteria that may be located amino terminal with respect to the proline rich portion of the overall amino acid sequence for such CBP.

The terms "identity", "% identity" or "percent identity" as utilized in this application refer to a calculation of differences between two contiguous sequences which have been aligned for "best fit" (to provide the largest number of aligned identical corresponding sequence elements, wherein elements are either nucleotides or amino acids) and all individual differences are considered as individual difference with respect to the identity. In this respect, all individual element gaps (caused by insertions and deletions with respect to an initial sequence ("reference sequence")) over the length of the reference sequence and individual substitutions of different elements (for individual elements of the reference sequence) are considered as individual differences in calculating the total number of differences between two sequences. Individual differences may be compared between two sequences where an initial sequences (reference sequence) has been varied to obtain a variant sequence (comparative sequence) or where a new sequence (comparative sequence) is simply aligned and compared to such a reference sequence. When two aligned sequences are compared all of the individual gaps in BOTH sequences that are caused by the "best fit" alignment over the length of the reference sequence are considered individual differences for the purposes of identity. If an alignment exists which satisfies the stated minimum identity, then a sequence has the stated minimum identity to the reference sequence. For example, the following is a hypothetical comparison of two sequences having 100 elements each that are aligned for best fit wherein one sequence is regarded as the "reference sequence" and the other as the comparative sequence. All of the individual alignment gaps in both sequences are counted over the length of the reference sequence and added to the number of individual element substitution changes (aligned elements that are different) of the comparative sequence for the total number of element differences. The total number of differences (for example 7 gaps and 3 substitutions) is divided by the total number of elements in the length of the reference sequence (100 elements) for the "percentage difference" (10/100). The resulting percentage difference (10%) is subtracted from 100% identity to provide a "% identity" of 90% identity. For the identity calculation all individual differences in both sequences are considered in the above manner over a discrete comparison length (the length of the reference sequence) of two best fit aligned sequences to determine identity. Thus, no algorithm is necessary for such an identity calculation.

"Isolated" in the context of the present invention with respect to polypeptides and/or polynucleotides means that the material is removed from its original environment (e.g., the natural environment if it is naturally occurring). For example, a naturally-occurring polynucleotide or polypeptide present in a living organism is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment. The polypeptides and polynucleotides of the present invention are preferably provided in an isolated form, and preferably are purified to homogeneity.

SUMMARY OF THE INVENTION

In one aspect the present invention relates to a vaccine for treating or preventing pneumococcal bacterial infections which utilizes as an immunogen at least one polypeptide truncate of a pneumococcal surface-binding protein, analog, or variant having a highly conserved immunogenic alpha-helical portion (corresponding generally to a "consensus" amino acid sequence as set forth in SEQ ID NO:1) with respect to different types of pneumococcal bacteria, which polypeptide does not include a choline-binding portion. Preferably, the C-terminal choline-binding portion is absent from such polypeptides. More preferred are such polypeptides wherein the HPS amino acid sequence is also absent. Even further preferred are polypeptides wherein the highly conserved immunogenic alpha-helical portion corresponding generally to a "consensus" amino acid sequence as set forth in SEQ ID NO:1 also corresponds generally to the amino acid sequence as set forth in SEQ ID NO:19 (amino acids 1 to 103 of SEQ ID NO:19 are identical to amino acids 1 to 103 of SEQ ID NO:1). Also preferred as vaccines are recombinantly-produced, isolated polypeptides that are missing both an HPS portion and the choline-binding portion.

More preferred as vaccines are one or more polypeptide truncates of pneumococcal surface-binding proteins, analogs or variants including a single highly conserved alpha-helix immunogenic portion with respect to different types of pneumococci, which polypeptides do not include a C-terminal choline-binding portion. Further preferred are isolated recombinantly produced polypeptides having such structure. Also preferred are such polypeptides that do not include either a C-terminal choline-binding portion or a HPS portion.

The present invention further provides a vaccine comprising a polypeptide including an immunogenic portion that is capable of forming an alpha helix, which polypeptide includes a sequence that has at least 85% identity and preferably at least 87% identity to the amino acid sequence of SEQ ID NO:1, wherein the isolated polypeptide does not include a C-terminal choline-binding portion. Further preferred are such polypeptides that comprise a polypeptide sequence that has at least 85% identity and preferably at least 87% identity to an amino acid sequence according SEQ ID NO:19. Preferably, the sequence of the isolated polypeptide includes neither an HPS portion (SEQ ID NO:2) nor a C-terminal choline-binding portion. Further preferred are isolated recombinantly produced polypeptides having such structure. In particular, such polypeptides corresponding to alpha helical structures of different types of *S. pneumoniae* bacteria are contemplated. Particularly preferred are the serotypes 1–5, 6A, 6B, 7F, 8, 9N, 9V, 10A, 11A, 12F, 14, 15B, 17F, 18C, 19F, 19A, 20, 22F, 23F and 33F of such *S. pneumoniae* bacteria. Examples of such serotypes of bacteria are readily available from standard ATCC catalogs.

In an additional aspect, the present invention further provides a vaccine against *S. pneumoniae* comprising a synthetic or recombinant polypeptide comprising a plurality of alpha-helical portions, each derived from different naturally occurring *S. pneumoniae* choline-binding polypeptides wherein such alpha-helical portions have at least 85% identity to the amino acid sequence of SEQ ID NO:1, and wherein the isolated polypeptide does not include a choline-binding portion. Further preferred are those wherein the amino acid sequence for the alpha-helix areas is at least 85% identical to the amino acid sequence of SEQ ID NO:19. Preferably, such synthetic polypeptide includes neither a HPS portion nor a choline-binding portion. Analogs and variants of such chain structure polypeptides wherein such alpha helical portions may be synthetic variant amino acid sequences (or may be a mixture of naturally occurring and variant sequences) are also contemplated and embraced by the present invention. In a preferred aspect, chain vaccines polypeptides having at least ten different alpha helical structures corresponding to *S. pneumoniae* serotypes 1–5, 6A, 6B, 7F, 8, 9N, 9V, 10A, 11A, 12F, 14, 15B, 17F, 18C, 19F, 19A, 20, 22F, 23F and 33F are provided. Further preferred are polypeptides including at least fifteen of such alpha-helical structures, more preferred are polypeptides including at least 20 such alpha-helical structures and more preferred are polypeptides including at least one alpha-helical structure corresponding to each of the *S. pneumoniae* serotypes 1–5, 6A, 6B, 7F, 8, 9N, 9V, 10A, 11A, 12F, 14, 15B, 17F, 18C, 19F, 19A, 20, 22F, 23F and 33F. Another preferred polypeptide comprises each of the alpha helical structures from the amino acid sequences of SEQ ID NOS:3–18 which correspond to SEQ ID NO:1.

In another aspect, the invention relates to passive immunity vaccines formulated from antibodies against a polypeptide including a highly conserved immunogenic portion with respect to different types of pneumococcal bacteria which portion is capable of forming an alpha-helix having the hereinbefore described identity to the amino acid sequence of SEQ ID NO:1, which polypeptide does not include a C-terminal choline-binding portion, wherein said antibodies will bind to at least one *S. pneumoniae* species. Preferably, if such polypeptide is a truncate of a native pneumococcal surface-binding protein both its HPS portion (where applicable) and its choline-binding portion are absent from such polypeptide. Such passive immunity vaccines can be utilized to prevent and/or treat pneumococcal infections in immunocompromised patients, patients having an immature immune system (such as young children) or patients who already have an ongoing infection. In this manner, according to a further aspect of the invention, a vaccine can be produced from a synthetic or recombinant polypeptide wherein the polypeptide includes the conserved alpha helical portions of two or more different choline binding polypeptides of *S. pneumoniae*.

This invention also relates generally to the use of an isolated polypeptide having a highly conserved immunogenic portion with respect to different types of pneumococcal bacteria which portion is capable of forming an alpha-helix (corresponding generally to SEQ ID NO:1 or to SEQ ID NO:19) wherein the isolated polypeptide does not include a choline-binding portion, to raise antibodies in non-human mammalian species useful, for example, as diagnostic reagents and vaccines.

In yet another aspect, the present invention relates to the production of a polypeptide including a highly conserved immunogenic portion with respect to different types of pneumococcal bacteria which portion is capable of forming an alpha-helix whose sequence corresponds generally to the amino acid sequence of SEQ ID NO:1 or SEQ ID NO:19, wherein the isolated polypeptide does not include a choline-binding portion. Preferably, such recombinant production is of a truncated native pneumococcal surface-binding polypeptide wherein both the HPS portion (where applicable) and the choline-binding portion are absent.

In still another aspect, the present invention provides an isolated choline-binding polypeptide, wherein the non-choline binding region of such polypeptide has at least 90% identity to the corresponding amino acid sequence portion of a naturally occurring pneumococcal surface-binding protein which is a member selected from the group consisting of SEQ ID NOS:3–18. The invention relates to fragments of such polypeptides which include at least the conserved alpha-helical portion corresponding generally to SEQ ID NO:1, and which has at least 85% identity thereto, wherein the isolated polypeptide preferably is free of a choline binding region.

In another aspect the present invention provides an isolated polypeptide comprising an amino acid sequence which has at least 90% identity to one of the amino acid sequences selected from the group consisting of SEQ ID NO:3–18. Preferably, such isolated polypeptide comprises an amino acid sequence which has at least 95% identity, and more preferably 97% identity, to one of the amino acid sequences selected from the group consisting of SEQ ID NO:3–18. The invention further relates to fragments of such polypeptides.

In a yet further aspect, the present invention provides a *S. pneumoniae* CBP polypeptide encoded by a polynucleotide that will hybridize under highly stringent conditions to the complement of a polynucleotide encoding a polypeptide having an amino acid sequence selected from the group consisting of SEQ ID NOS:1 and 3–8. Particularly preferred are polypeptides comprising an amino acid sequence segment that is at least 90% identical to the amino acid sequence of SEQ ID NO:1. Further preferred are such polypeptides comprising a contiguous amino acid sequence that has at least 95% identity with respect to the amino acid sequence of SEQ ID NO:1. And, even more preferred are polypeptides comprising an amino acid sequence that has at least 97% identity with respect to the amino acid sequence of SEQ ID NO:1.

In another aspect the present invention provides polynucleotides which encode the hereinabove described polypeptides of the invention. The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The polynucleotides which encode polypeptides including the amino acid sequences of at least one of SEQ ID NOS:3–18 (or polypeptides that have at least 90% identity to the amino acid sequences of such polypeptides) may be one of the coding sequences shown in SEQ ID NOS:20–35 or may be of a different coding sequence which coding sequence, as a result of the redundancy or degeneracy of the genetic code, encodes the same polypeptides as the DNA of SEQ ID NOS:20–35.

The polynucleotides which encode the polypeptides of SEQ ID NOS:3–18 may include: only the coding sequence for the polypeptide; the coding sequence for the polypeptide (and optionally additional coding sequence) and non-coding sequence, such as introns or non-coding sequence 5' and/or 3' of the coding sequence for the polypeptide. The polypeptides encoded may comprise just a single alpha-helical portion or multiple alpha-helical portion and may independently or collectively include N-terminal sequences 5' of such alpha helical areas and/or sequences corresponding to the "X" structures or proline rich areas (as set forth in FIG. 1, for example).

The invention further relates to a polynucleotide comprising a polynucleotide sequence that has at least 95% identity and preferably at least 97% identity to a polynucleotide encoding one of the polypeptides comprising SEQ ID NO:3–18. The invention further relates to fragments of such polynucleotides which include at least the portion of the polynucleotide encoding the polypeptide sequence corresponding to SEQ ID NO:1.

Thus, the term "polynucleotide encoding a polypeptide" encompasses a polynucleotide which includes only coding sequence for the polypeptide as well as a polynucleotide which includes additional coding and/or non-coding sequence. In particular, the polypeptides may include any or all of the types of structures set forth schematically in FIG. 1.

The present invention further relates to variants of the hereinabove described polynucleotides which encode for fragments, analogs and derivatives of the polypeptides including the amino acid sequences of SEQ ID NOS:3–18. The variants of the polynucleotides may be a naturally occurring allelic variant of the polynucleotides or a non-naturally occurring variant of the polynucleotides. Complements to such coding polynucleotides may be utilized to isolate polynucleotides encoding the same or similar polypeptides. In particular, such procedures are useful to obtain alpha helical coding segments from different serotypes of *S. pneumoniae*, which is especially useful in the production of "chain" polypeptide vaccines containing multiple alpha helical segments.

Thus, the present invention includes polynucleotides encoding polypeptides including the same polypeptides as shown in the Sequence Listing as SEQ ID NOS:3–18 as well as variants of such polynucleotides which variants encode for a fragment, derivative or analog of the polypeptides of SEQ ID NOS:3–18. Such nucleotide variants include deletion variants, substitution variants and addition or insertion variants.

As hereinabove indicated, the polynucleotides may have a coding sequence which is a naturally occurring allelic variant of the coding sequence shown in the Sequence Listing as SEQ ID NOS:20–35. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptides of the present invention. The marker sequence may be, for example, a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides (hybridization target sequences) which hybridize to the complements of the hereinabove-described sequences if there is at least 70% and preferably 80% identity between the target sequence and the complement of the sequence to which the target sequence hybridizes, preferably at least 85% identity. More preferred are such sequences having at least 90% identity, preferably at least 95% and more preferably at least 97% identity between the target sequence and the sequence of complement of the polynucleotide to which it hybridizes. The invention further relates to the complements to both the target sequence and to the polynucleotide sequence that encodes an amino acid sequence selected from the group consisting of SEQ ID NOS:3 to 18. The present invention particularly relates to polynucleotides which hybridize under stringent conditions to the complements of the hereinabove-described polynucleotides as well as to those complements. As herein used, the term "stringent conditions" means hybridization will occur with the complement of a polynucleotide and a corresponding sequence only if there is at least 95% and preferably at least 97% identity between the target sequence and the sequence of complement of the polynucleotide to which it hybridizes. The polynucleotides which hybridize to the complements of the hereinabove described polynucleotides in a preferred embodiment encode polypeptides which retain an immunogenic portion that will cross-react with an antibody to at least one of the polypeptides having a sequence according to SEQ ID NOS:3–18, or to a polypeptide that includes an amino acid sequence which has at least 85% identity to that of SEQ ID NO:1.

In a still further aspect, the present invention provides for the production of such polypeptides and vaccines as set forth above having a histidine label (or other suitable label) such that the full-length proteins, truncates, analogs or variant discussed above can be isolated due to their label.

In another aspect the present invention relates to a method of prophylaxis and/or treatment of diseases that are mediated by pneumococcal bacteria that have surface-binding CBP proteins. In particular, the invention relates to a method for the prophylaxis and/or treatment of infectious diseases that are mediated by S. pneumoniae that have a CBP surface-binding protein that forms an alpha helix (comprising a sequence that has at least an 85% identity to the amino acid sequence of SEQ ID NO:1). In a still further preferred aspect, the invention relates to a method for the prophylaxis and/or treatment of such infections in humans.

In still another aspect the present invention relates to a method of using one or more antibodies (monoclonal, polyclonal or sera) to the polypeptides of the invention as described above for the prophylaxis and/or treatment of diseases that are mediated by pneumococcal bacteria that have CBP surface-binding proteins. In particular, the invention relates to a method for the prophylaxis and/or treatment of infectious diseases that are mediated by S. pneumoniae CBP proteins which include an alpha helical portion having the hereinbefore described identity to the consensus sequence of SEQ ID NO:1. In a still further preferred aspect, the invention relates to a method for the prophylaxis and/or treatment of otitis media, nasopharyngeal, bronchial infections, and the like in humans by utilizing antibodies to the alpha-helix containing immunogenic polypeptides of the invention as described above.

BRIEF DESCRIPTION OF DRAWINGS

FIG. 12 shows the sequence pair distances for the amino acid sequences as described for FIG. 11 and set forth therein. A Clustal method with identity residue weight table is used. The percent similarity for such a comparison is reported for the amino acid sequences set forth in FIG. 11.

DETAILED DESCRIPTION OF THE INVENTION

Figure 1:
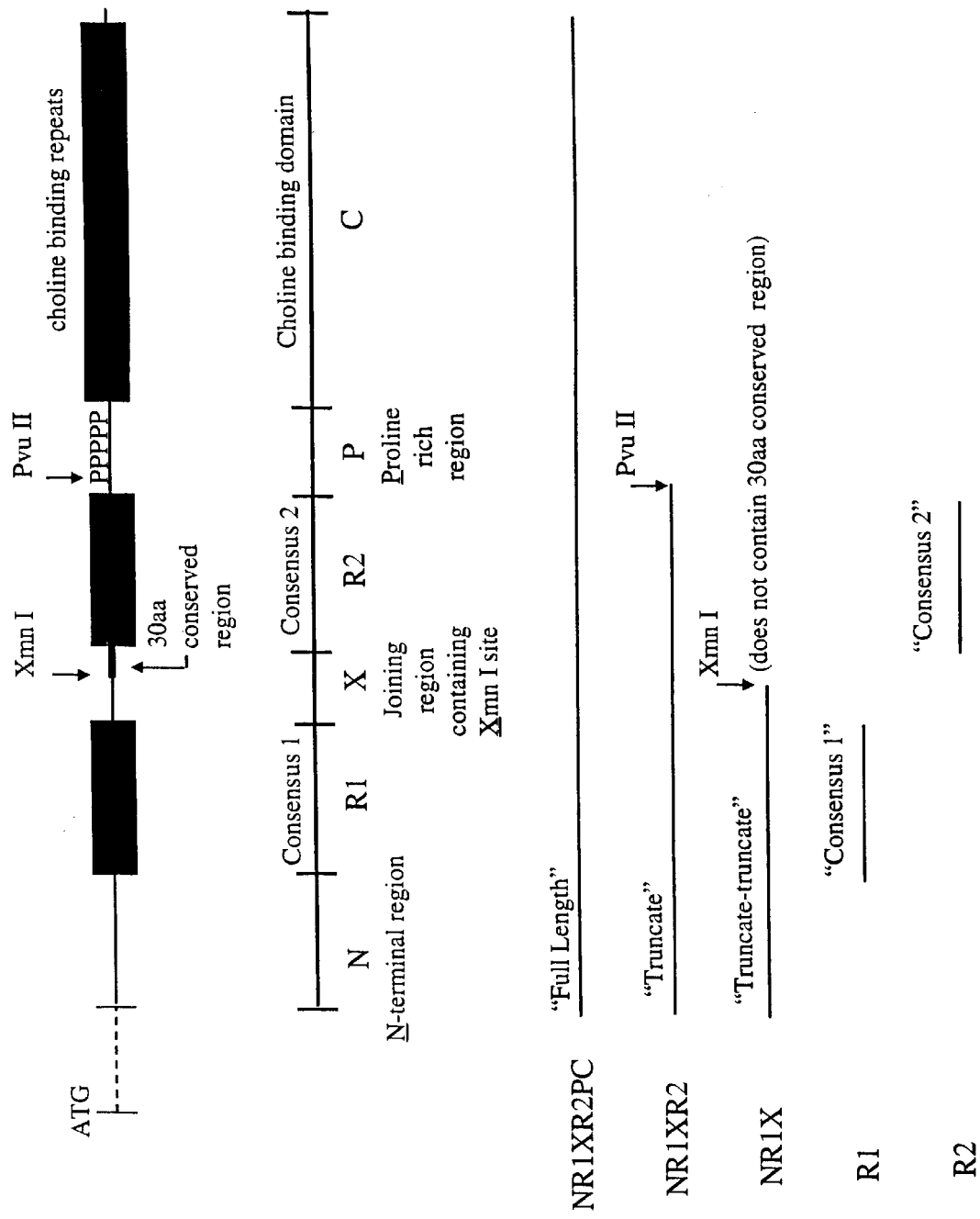
FIG. 1 is a diagram of a pneumococcal CBP protein which shows from the N-terminal to the C-terminal, respectively, (a) a N-terminal sequence, (b) one of a potential alpha-helical forming area conserved segment (R1) that may not be present in some CBP polypeptides, (c) an optional small bridging sequence of amino acids that may bridge two conserved alpha-helical segments (X), (d) a second of a potential alpha-helical forming area consensus sequence (R2) related to the first consensus sequence (which corresponds to SEQ ID NO:1), (e) a proline rich area sequence, (f) a choline binding repeats area, and (e) a C-terminal tail sequence. Where relevant, an optional HPS sequence may naturally occur 5' of the proline rich sequence and 3' of the R1, X, and/or R2 areas.

In accordance with an aspect of the present invention there is provided a vaccine to produce a protective response against *S. pneumoniae* infections which employs a polypeptide which comprises a member selected from the group consisting of:

(a) an amino acid sequence which produces an alpha helical structure and which is at least 85% identical to the amino acid sequence of SEQ ID NO:1 and which is free of a choline binding region, and (b) an isolated truncate of a naturally occurring *S. pneumoniae* polypeptide that comprises an alpha helical portion that has at least 85% identity to the amino acid sequence of SEQ ID NO:1 and is free of a choline binding region, (c) an isolated truncate of a naturally occurring *S. pneumoniae* polypeptide that comprises an alpha helical portion that has at least 90% identity to the amino acid sequence of SEQ ID NO:19 and is free of a choline binding region. In a preferred aspect, such isolated truncate polypeptide is a member selected from the group consisting of SEQ ID NOS:3–18 and said isolated polypeptide is free of a choline binding region and, if relevant, a HPS region; or a fragment thereof which includes at least the alpha helical segment which corresponds to the consensus sequence of SEQ ID NO:1. Particularly preferred are vaccines which utilize such truncate polypeptides that include at least such alpha helical area or utilize a recombinant immunogen polypeptide comprising at least two of such alpha-helical segments. Such polypeptide may be a recombinant polypeptide containing multiple alpha-helical areas from one or more trucates. Further preferred are recombinant immunogen polypeptides comprising at least two alpha-helical areas corresponding to the alpha helical areas of two or more truncates from different types of pneumococcal bacteria. Such polypeptide may be a recombinant polypeptide containing multiple alpha-helical areas from one or more different types of pneumococcal bacteria.

In accordance with the present invention, there is provided an isolated polypeptide comprising a truncated surface-binding polypeptide derived from *S. pneumoniae*, said isolated polypeptide containing an alpha-helical area whose amino acid sequence corresponds generally to the amino acid sequence of SEQ ID NO:1, but free of a choline binding area. Preferably, said isolated polypeptide also omits any naturally occurring repeats of the alpha-helical forming area and omits any HPS amino acid sequence that may be present.

It is an object of the present invention to utilize as immunogenic composition for a vaccine (or to produce antibodies for use as a diagnostic or as a passive vaccine) comprising an immunogenic polypeptide comprising a pneumococcal surface-binding polypeptide with an alpha helical portion from which a choline binding region has been omitted. In one embodiment, such truncated proteins (naturally or recombinantly produced, as well as functional analogs) from *S. pneumoniae* bacteria are contemplated. Even more particularly, *S. pneumoniae* polypeptides having a single alpha helical portion that omit any HPS areas that occur and choline binding areas of the native protein are contemplated.

A particularly preferred embodiment of such an immunogenic composition is for use as a vaccine (or as an immunogen for producing antibodies useful for diagnostics or vaccines) wherein the active component of the immunogenic composition is an isolated polypeptide comprising at least one member selected from the group consisting of:

(a) an amino acid sequence which is selected from SEQ ID NOS:3–19, (b) a polypeptide which has at least 90% identity to (a), preferably at least 95% identity to (a), and even more preferred at least 97% identity to (a), or (c) a fragment of (a) or (b) wherein such fragment includes at least one alpha helical portion that corresponds to the consensus sequence which is SEQ ID NO:1 and said fragment does not comprise a choline binding region. Preferably, such vaccines utilize a polypeptide that contains neither a choline binding region nor an HPS region that occurs as part of the amino acid sequences in the native proteins.

In another preferred embodiment, there is provided a vaccine which includes at least one isolated polypeptide which includes an amino acid sequence which has at least 85% identity (preferably 87% identity and more preferably at least 90% identity) to SEQ ID NO:1, which isolated polypeptide is free of a choline binding portion and, where applicable, is also preferably free of an HPS portion. The preferred polypeptide may also include one or more of the N-terminal sequences that are located 5' of the alpha helical areas in the polypeptides having an amino acid sequence selected from the group consisting of SEQ ID NOS:3–18, or the like. The polypeptide truncate may also include one or more of the proline regions (region "P" in FIG. 1) and/or the spanning region (region "X" in FIG. 1).

In another aspect of the invention, such an immunogenic composition may be utilized to produce antibodies to diagnose pneumococcal infections, or to produce vaccines for prophylaxis and/or treatment of such pneumococcal infections as well as booster vaccines to maintain a high titer of antibodies against the immunogen(s) of the immunogenic composition.

While other antigens have been contemplated to produce antibodies for diagnosis and for the prophylaxis and/or treatment of pneumococcal infections, there is a need for improved or more efficient vaccines. Such vaccines should have an improved or enhanced effect in preventing bacterial infections mediated pneumococci having surface-binding polypeptides. Further, to avoid unnecessary expense and provide broad protection against a range of pneumococcal serotypes there is a need for polypeptides that comprise an immunogenic amino acid sequence corresponding to a portion of pneumococcal surface-binding polypeptides that is a highly conserved portion among various types of pneumococci. Preferably, such polypeptides avoid the inclusion of amino acid sequences corresponding to other portions of the native polypeptides, such as the choline binding region and/or the HPS region.

There is a need for improved antigenic compositions comprising highly conserved portions of polypeptides that bind to the surface of pneumococcal bacteria for stimulating high-titer specific antisera to provide protection against infection by pathogenic pneumococcal bacteria and also for use as diagnostic reagents.

In such respect, truncated polypeptides, functional variant analogs, and recombinantly produced truncated polypeptides of the invention are useful as immunogens for preparing vaccine compositions that stimulate the production of antibodies that can confer immunity against pathogenic species of bacteria. Further, preparation of vaccines containing purified proteins as antigenic ingredients are well known in the art.

Generally, vaccines are prepared as injectables, in the form of aqueous solutions or suspensions. Vaccines in an oil base are also well known such as for inhaling. Solid forms which are dissolved or suspended prior to use may also be formulated. Pharmaceutical carriers are generally added that are compatible with the active ingredients and acceptable for pharmaceutical use. Examples of such carriers include, but are not limited to, water, saline solutions, dextrose, or glycerol. Combinations of carriers may also be used.

Vaccine compositions may further incorporate additional substances to stabilize pH, or to function as adjuvants, wetting agents. or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art.

The amount of vaccine sufficient to confer immunity to pathogenic bacteria is determined by methods well known to those skilled in the art. This quantity will be determined based upon the characteristics of the vaccine recipient and the level of immunity required. Typically, the amount of vaccine to be administered will be determined based upon the judgment of a skilled physician. Where vaccines are administered by subcutaneous or intramuscular injection, a range of 50 to 500 µg purified protein may be given.

The term "patient in need thereof" refers to a human that is infected with, or likely, to be infected with, pathogenic pneumococcal bacteria that produce CbpA, or the like, preferably *S. pneumoniae* bacteria (however a mouse model can be utilized to simulate such a patient in some circumstances).

In addition to use as vaccines, the polypeptides of the present invention can be used as immunogens to stimulate the production of antibodies for use in passive immunotherapy, for use as diagnostic reagents, and for use as reagents in other processes such as affinity chromatography.

The polynucleotides encoding the immunogenic polypeptides described above may also have the coding sequence fused in frame to a marker sequence which allows for purification of the polypeptides of the present invention. The marker sequence may be, for example, a hexa-histidine tag supplied by-a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The identification of multiple coil structures of alpha helical amino acid segments in the S. pneumoniae polypeptides according to the invention may be determined by the location of proline rich areas with respect to one another. Further the "X" area optionally located between two or more alpha-helical structures can play a part in the formation of a coil within a coil structure. Standard three-dimensional protein modeling may be utilized for determining the relative shape of such structures. An example of a computer program, the Paircoil Scoring Form Program ("PairCoil program"), useful for such three-dimensional protein modelling is described by Berger et al. in the Proc. Natl. Acad. of Sci. (USA), 92:8259–8263 (August 1995). The PairCoil program is described as a computer program that utilizes a mathematical algorithm to predict locations of coiled-coil regions in amino acid sequences. A further example of such a computer program is described by Wolf et al., Protein Science 6:1179–1189 (June 1997) which is called the Multicoil Scoring Form Program ("Multicoil program"). The MultiCoil program is based on the PairCoil algorithm and is useful for locating dimeric and trimeric coiled coils In a preferred aspect, the invention provides for recombinant production of such polypeptides in a host bacterial cell other than a S. pneumoniae species host to avoid the inclusion of native surface-binding polypeptides that have a choline binding region. A preferred host is a species of such bacteria that can be cultured under conditions such that the polypeptide of the invention is secreted from the cell.

The present invention also relates to vectors which include polynucleotides encoding one or more of the polypeptides of the invention that include the highly conserved alpha-helical amino acid sequence in the absence of an area encoding a choline binding amino acid sequence, host cells which are genetically engineered with vectors of the invention and the production of such immunogenic polypeptides by recombinant techniques in an isolated and substantially immunogenically pure form.

Host cells are genetically engineered (transduced or transformed or transfected) with the vectors comprising a polynucleotide encoding a polypeptide comprising the highly conserved alpha-helical region but not having a choline binding region, or the like of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the polynucleotides which encode such polypeptides. The culture conditions, such as temperature, pH and the like, are those previously used with the host cell selected for expression, and will be apparent to the ordinarily skilled artisan.

Vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the proteins.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen, Inc.), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, PBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232–8 and pCM7. Particular named bacterial promoters include lacI, lacZ, T3, T7, gpt, lambda $P_R$, $P_L$ and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, a french press, mechanical disruption, or use of cell lysing agents, such methods are well know to those skilled in the art. However, preferred are host cells which secrete the polypeptide of the invention and permit recovery of the polypeptide from the culture media.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and/or purified from recombinant cell cultures by well-known protein recovery and purification methods. Such methodology may include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. In this respect, chaperones may be used in such a refolding procedure. Finally, high performance liquid chromatography (HPLC) can be employed for final purification steps.

The polypeptides that are useful as immunogens in the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Particularly preferred immunogens are truncated pneumococcal polypeptides that comprise a single highly conserved alpha helical area, but do not comprise a choline binding region or a HPS region. Therefore, antibodies against such polypeptides should bind to other pneumococcal bacterial species (in addition to the S. pneumoniae species from which such polypeptides were derived) and vaccines against such *S. pneumoniae* should give protection against other pneumococcal bacterial infections.

Procedures for the isolation of the individually expressed alpha-helical containing polypeptides may be isolated by recombinant expression/isolation methods that are well-known in the art. Typical examples for such isolation may utilize an antibody to a conserved area of the protein or to a His tag or cleavable leader or tail that is expressing as part of the protein structure.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

In order to facilitate understanding of the above description and the examples which follow below, as well as the Figures included herewith, Table 1 below sets forth the bacterial source for the polypeptides of SEQ ID NOS:3–18 and the polynucleotides encoding them (SEQ ID NOS:20–35, respectively). The name and/or type of bacteria is specified and a credit or source is named. The sequences from such types of bacteria are for illustrative purposes only since by utilizing probes and/or primers as described herein other sequences of similar type may be readily obtained by utilizing only routine skill in the art.

TABLE 1

| SEQ ID NO. | Type Of Pneumococcus | Source Credit or ATCC No. |
|---|---|---|
| 3 | 1 | ATCC 33400 |
| 4 | 2 | SPATCC 11733 |
| 5 | 2 | ATCC2 (catalog #6302) |
| 6 | 4 | ATCC4 (catalog #6304) |
| 7 | 6B | ATCC 6B (catalog #6326) |
| 8 | 18C | SPATCC 18C (ATCC catalog #10356) |

TABLE 1-continued

| SEQ ID NO. | Type Of Pneumococcus | Source Credit or ATCC No. |
|---|---|---|
| 9 | 4 | Norway type 4; Nat'l. Inst. of Public Health, Norway Ingeborg Aagerge |
| 10 | noncapsulated | R6X; Rockefeller Univ., Rob Masure (from D39, type 2) |
| 11 | 6B | SPB 105; Boston Univ., Steve Pelton |
| 12 | 23F | SPB 328; Boston Univ., Steve Pelton |
| 13 | 14 | SPB 331; Boston Univ., Steve Pelton |
| 14 | 23F | SPB 365; Boston Univ., Steve Pelton |
| 15 | 9V | SPR 332; Rockefeller Univ., Rob Masure |
| 16 | 6B | SPSJ 2p; St. Jude Children's Research Hospital, Pat Flynn (clinical isolate passaged 1x in mice for virulence) |
| 17 | 14 | SPSJ 9; St. Jude Children's Research Hospital, Pat Flynn (clinical isolate - nares, pneumonia) |
| 18 | 19A | SPSJ 12; St. Jude Children's Research Hospital, Pat Flynn (clinical isolate) |

The present invention will be further described with reference to the following examples; however, it is to be understood that the present invention is not limited to such examples. All parts or amounts, unless otherwise specified, are by weight.

EXAMPLE 1

Generation of CbpA Truncate Protein Vectors

A. Vector for Full Length CbpA (NR1 XR2PC)

A virulent serotype 4 *S. pneumoniae* strain, Norway 4 (obtained from I. Aaberge, National Instute of Public Health, Oslo, Norway) was used as a source of genomic DNA template for amplifying the polynucleotide encoding full-length CbPA. Full length CbpA was amplified with PCR primers SJ533 and SJ537 described below.

The degenerate forward primer SJ533 was designed based on the CbpA N-terminal sequence XENEG provided by H. R. Masure (St. Jude Childern's Research Hospital, Memphis, Tenn.). The SJ533 primer=5' GGC GGA TCC ATG GA(A,G) AA(C,T) GA(A,G) GG 3'. It incorporates both BamHI and NcoI restriction sites and an ATG start codon.

The 3' reverse primer SJ537=5' GCC GTC GAC TTA GTT TAC CCA TTC ACC ATT GGC 3'.

This primer incorporates a SalI restriction site for cloning purposes, and the natural stop codon from CbpA, and is based on type 4 and R6X sequence generated in-house.

PCR product generated from genomic DNA template with SJ533 and SJ537 was digested with BamHI and SalI, and cloned into the pQE30 expression vector (Qiagen, Inc.) digested with BamHI, XbaI, and SmaI. The type R6X template resulted in full-length vector PMI581 and the type 4 template DNA resulted in full-length vector PMI580.

B. Vector for CbpA Truncate Protein (NR1XR2)

The naturally occurring PvuII site in the end on the second amino repeat (nucleic acid 1228 of Type 4 sequence) was exploited to create a truncated version of CbpA, containing only the amino terminus of the gene. To create the truncate clone, the full-length clone PMI580 (Type 4) or PMI581 (R6X) was digested with PvuII and XbaI, and the amino terminus along with a portion of the expression vector was isolated by size on an agarose gel. pQE30 was digested with XbaI and SmaI, and the band corresponding to the other half of the vector was also size selected on an agarose gel. The two halves were ligated and clones identified by restriction digest, then expressed. In this instance, the stop codon utilized is in the expression vector, so the protein expressed is larger than the predicted size due to additional amino acids at the 5' and 3' end of the cloning site.

C. Vector for CbpA Truncate Protein (NR1X)

A similar strategy was used to express only the first amino repeat of CbpA. Here the naturally occurring XmnI site between the two amino repeats (nucleic acid 856 of Type 4 sequence) was utilized. CbpA full-length clone PMI580 was digested with XmnI and AatII. Expression vector pQE30 was digested with AatII and SmaI. Once again, the two sized fragments were ligated, and clones were screened by restriction digest and expressed.

EXAMPLE 2

Expression of CbpA Truncate Protein from Expression Vectors

All proteins are expressed from the vectors described in Examples 1A–1C in the Qia expressionist System (Qiagen) using the *E. coli* expression vector pQE30, and the amino terminus His6 tagged proteins are detected by western analysis using both anti-Histidine antibodies and gene specific antibodies.

The expressed CBP truncates were purified as follows. A single colony was selected from plated bacteria containing the recombinant plasmid and grown overnight at 37° in 6.0 ml LB buffer with 50 ug/ml Kanamycin and 100 ug/ml Ampicillin. This 6.0 ml culture was added to 1L LB with antibiotics at above concentrations. The culture was shaken at 37° C. until $A_{600}=\sim 0.400$. 1M IPTG was added to the 1L culture to give a final concentration of 1 mM. The culture was then shaken at 37° C. for 3–4 h. The 1L culture was spun 15 min. in 250 ml conical tubes at 4000 rpm in a model J-6B centrifuge. The supernatant was discarded and the pellet stored at −20° C. until use.

The 1L pellet was resuspended in 25 ml 50 mM $NaH_2PO_4$, 10 mM Tris, 6M GuCl, 300 mM NaCl, pH 8.0 (Buffer A). This mixture was then rotated at room temperature for 30 minutes. The mixture was then subjected to sonication (VibraCell Sonicator, Sonics and Materials, Inc., Danbury, Conn.) using the microtip, two times, for 30 sec., at 50% Duty Cycle and with the output setting at 7. The mixture was spun 5 min. at 10K in a JA20 rotor and the supernatant removed and discarded. The supernatant was loaded on a 10 ml Talon (Clonetech, Palo Alto, Calif.) resin column attached to a GradiFrac System (Pharmacia Biotech, Upsala, Sweden). The column was equilibrated with 100 ml Buffer A and washed with 200 ml of this buffer. A volume based pH gradient using 100% 50 mM $NaH_2PO_4$, 8M Urea, 20 mM MES, pH 6.0 (Buffer B) as the final target buffer was run over a total volume of 100 ml. Protein eluted at ~30% Buffer B. Eluted peaks were collected and pooled.

For refolding, dialysis was carried out with a 2L volume of PBS at room temperature for approximately 3 hr. using dialysis tubing with a molecular weight cutoff of 14,000. The sample was then dialyzed overnight in 2L of PBS at 4° C. Additional buffer exchange was accomplished during the concentration of the protein using Centriprep-30 spin columns by adding PBS to the spun retentate and respinning. The protein concentration was determined using the BCA protein assay and the purity visualized using a Coomassie stained 4–20% SDS-PAGE gel.

EXAMPLE 3

Passive Protection with Anti-CbpA Truncate NR1XR2 Antisera

A. Generation of Rabbit Immune Serum

Rabbit immune serum against CbpA truncate was generated at Covance (Denver, Pa.). Following collection of preimmune serum, a New Zealand white rabbit (#ME101) was immunized with 250 µg CbpA truncate NR1XR2 (containing both alpha helix I and alpha helix II amino acid N-terminal repeats that are prepared from 483:58) in Complete Freund's Adjuvant. The rabbit was given a boost of 125 µg CbpA truncate in Incomplete Freund's Adjuvant on day 21 and bled on days 31 and 52.

B. Passive Protection in Mice

C3H/HeJ mice (5 mice/group) were passively immunized intraperitoneally with 100 µl of a 1:2 dilution of rabbit sera in sterile PBS (preimmune or day 31 immune sera). One hour after administration of serum, mice were challenged with 1600 cfu virulent serotype 6B *S. pneumoniae*, strain SP317 (obtained from H. R. Masure). Mice were monitored for 14 days for survival.

Figure 2:
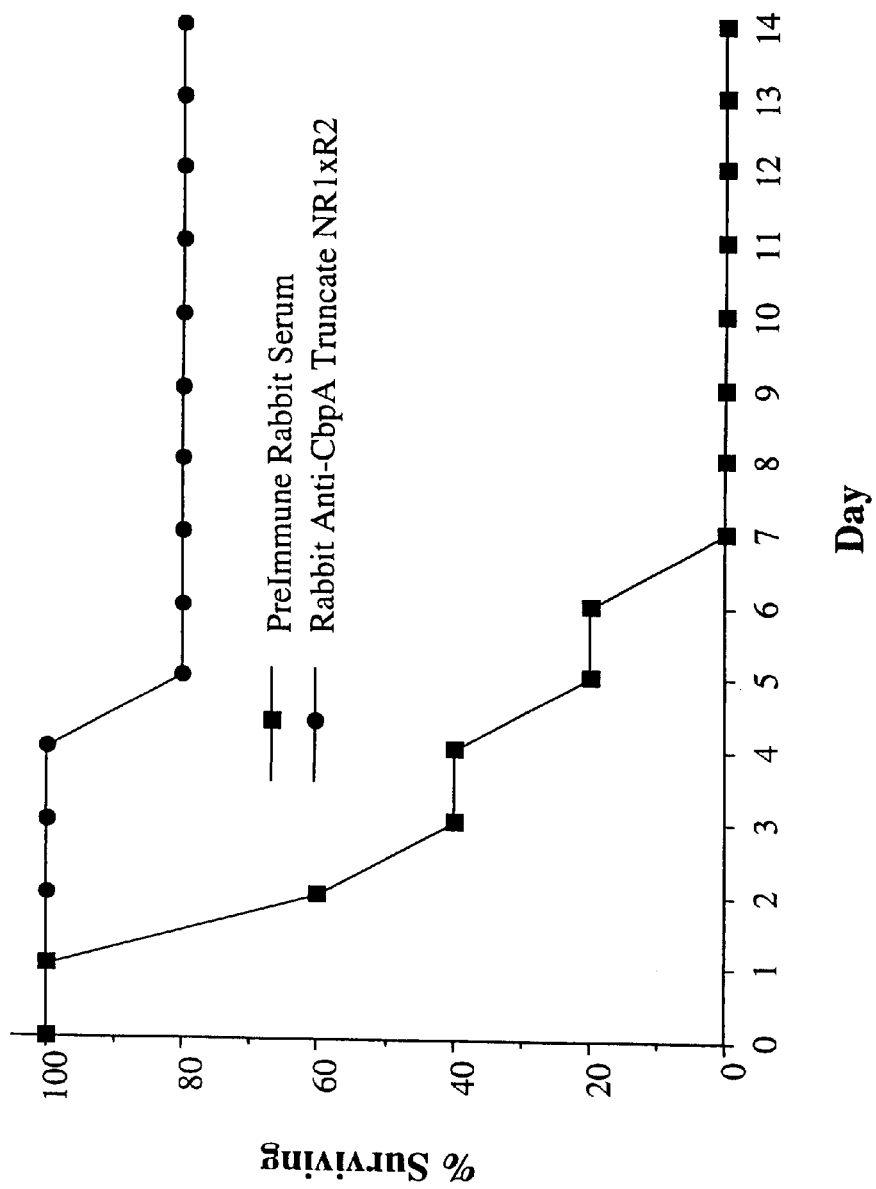
FIG. 2 reports the results for passive immunity protection against 1600 cfu virulent serotype 6B S. pneumoniae SP317 (in mice) that was provided by day 31 rabbit antisera to a pneumococcal CBP truncate polypeptide, NR1XR2 (truncate missing both the proline and the choline binding areas, but including two conserved alpha-helical areas R1 and R2). Eighty percent of the mice immunized with the truncate antisera prior to challenge survived the 14 day observation period. By contrast, all mice immunized with a control sera (pre-immune rabbit sera) were dead by day 7.

Eighty percent of the mice immunized with rabbit immune serum raised against CbpA truncate NR1XR2 protein survived the challenge for 14 days (FIG. 2). All mice immunized with preimmune rabbit serum were dead by day 7.

C. Passive Protection in Mice (Higher Challenge Dose)

C3H/HeJ mice (10 mice/group) were passively immunized intraperitoneally with 100 µl of a 1:2 dilution of rabbit sera in sterile PBS (preimmune or day 52 immune sera). One hour after administration of serum, mice were challenged with 3450 cfu virulent serotype 6B *S. pneumoniae*, strain SP317. Mice were monitored for 10 days for survival.

Figure 3:
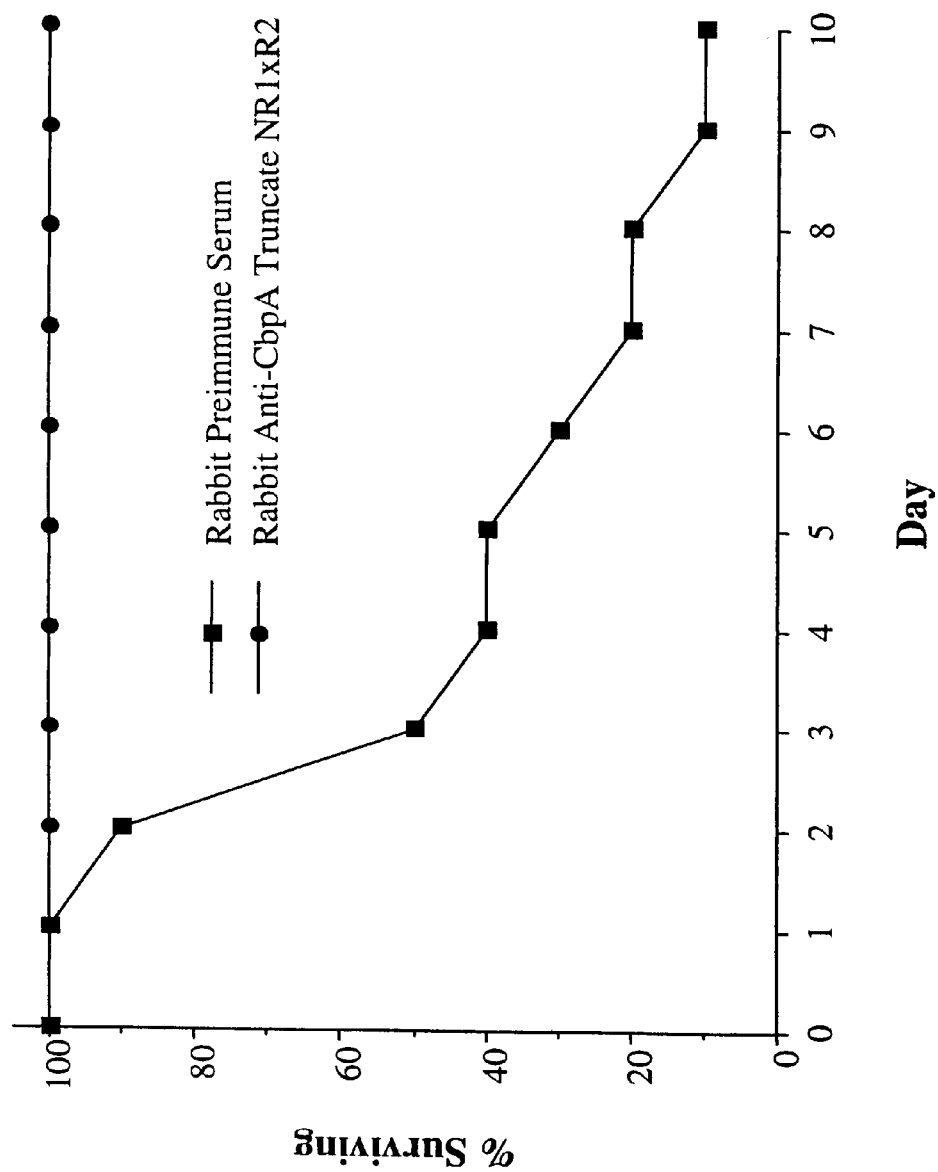
FIG. 3 reports the results for passive immunity protection against 3450 cfu virulent serotype 6B S. pneumoniae SP317 (in mice) that was provided by day 52 rabbit antisera to a pneumococcal CBP truncate polypeptide, NR1XR2 (truncate missing both the proline and the choline binding areas, but including two conserved alpha-helical areas R1 and R2). One hundred percent of the mice immunized with the truncate antisera prior to challenge survived the 10 day observation period. By contrast, ninety percent of the mice immunized with a control sera (pre-immune rabbit sera) were dead at day 10.

One hundred percent of the mice immunized with rabbit immune serum raised against CbpA truncate NR1XR2 protein survived the challenge for ten days (FIG. 3). Ninety percent of the mice immunized with preimmune rabbit serum were dead at day 10.

D. Passive Protection in Mice (Against High Virulence)

C3H/HeJ mice (10 mice/group) were passively immunized intraperitoneally with 100 µl of a 1:2 dilution of rabbit sera in sterile PBS (preimmune or day 52 immune sera). One hour after administration of serum, mice were challenged with 580 cfu virulent serotype 6B *S. pneumoniae*, strain SPSJ2 (provided by P. Flynn, St. Jude Children's Research Hospital, Memphis, Tenn.). Mice were monitored for 10 days for survival.

Figure 4:
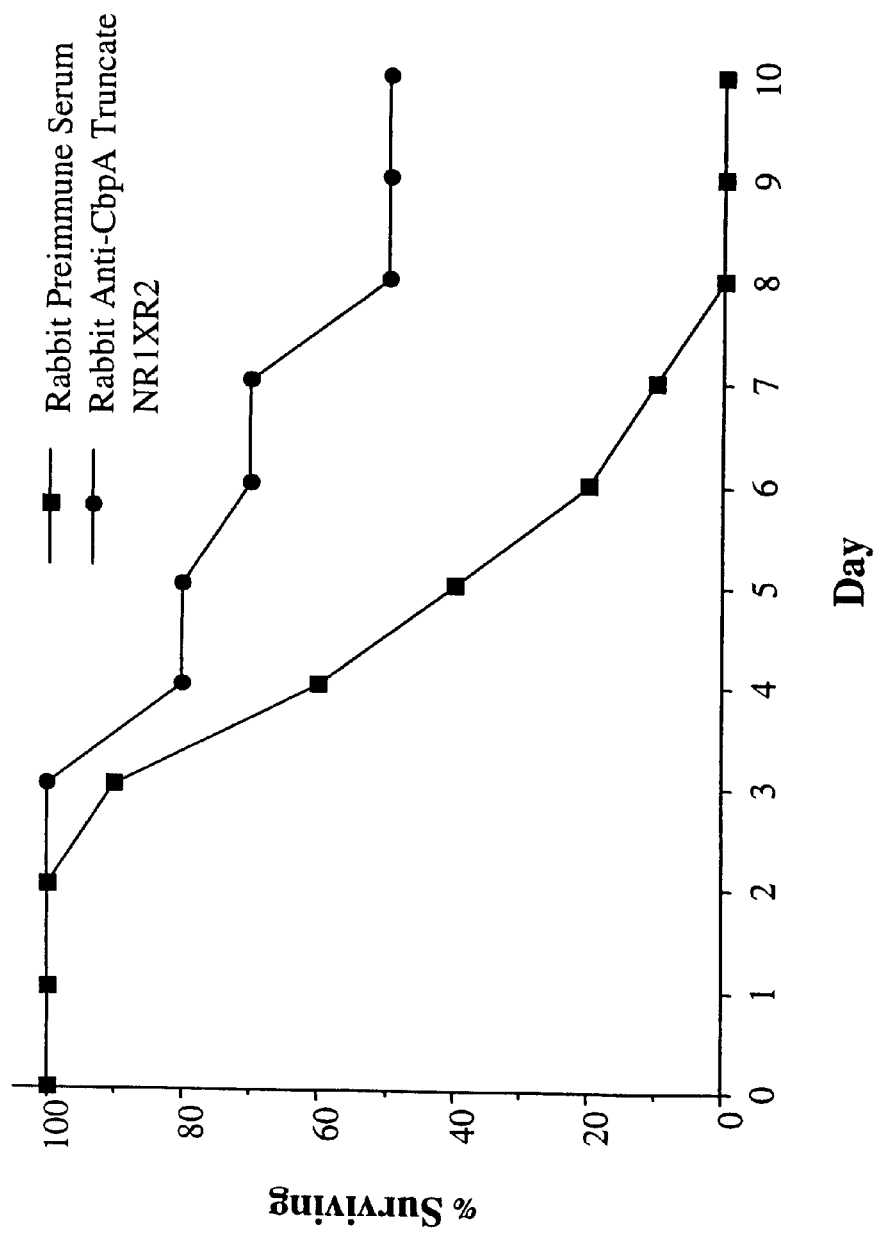
FIG. 4 reports the results for passive immunity protection against 580 cfu virulent serotype 6B S. pneumoniae SPSJ2 (in mice) that was provided by day 31 rabbit antisera to a pneumococcal CBP truncate polypeptide, NR1XR2 (truncate missing both the proline and the choline binding areas, but including two conserved alpha-helical areas R1 and R2). Fifty percent of the mice immunized with the truncate antisera prior to challenge survived the 10 day observation period. By contrast, all mice immunized with a control sera (pre-immune rabbit sera) were dead by day 8.

Fifty percent of the mice immunized with rabbit immune serum raised against CbpA truncate NR1XR2 protein survived the challenge for 10 days (FIG. 4). All of the mice immunized with preimmune rabbit serum were dead at day 8.

These data demonstrate that antibodies specific for CbpA are protective against systemic pneumococcal infection. The data further indicate that the choline-binding region is not necessary for protection, as antibody specific for truncated protein NR1XR2, lacking the choline-binding repeats, was sufficient for protection. In addition, serum directed against recombinant CbpA protein based on a serotype 4 sequence, was still protective against challenge with two different strains of serotype 6B.

EXAMPLE 4

Active Protection with Anti-CbpA Truncates NR1X and NR1XR2

A. Active Protection with NR1X Truncate Vaccination

C3H/HeJ mice (10/group) were immunized intraperitoneally with CbpA truncate protein NR1X (15 μg in 50 μl PBS, plus 50 μl Complete Freund's Adjuvant). A group of 10 sham immunized mice received PBS and adjuvant. A second immunization was administered four weeks later, 15 μg protein i.p. with Incomplete Freund's Adjuvant (sham group received PBS plus IFA). Blood was drawn (retro-orbital bleed) at weeks 3, 6, and 9 for analysis of immune response. The ELISA end point anti-CbpA truncate titer of pooled sera from the 10 CbpA immunized mice at 9 weeks was 4,096,000. No antibody was detected in sera from sham immunized mice. Mice were challenged at week 10 with 560 CFU serotype 6B S. pneumoniae strain SPSJ2. Mice were monitored for 14 days for survival.

Figure 5:
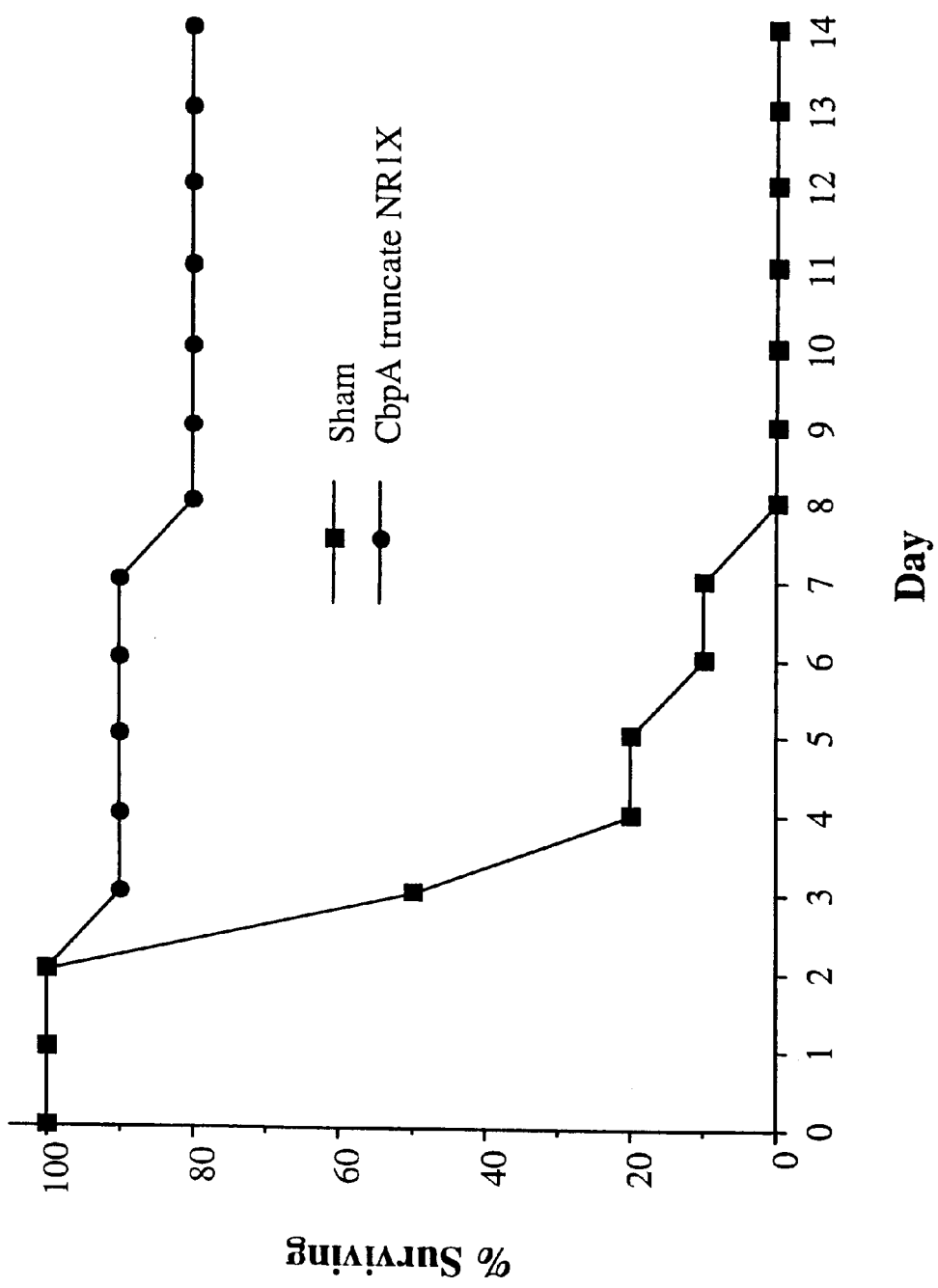
FIG. 5 reports the results for active immunity protection against 560 cfu virulent serotype 6B *S. pneumoniae* SPSJ2 (in mice) that was provided by immunization with a pneumococcal CBP truncate polypeptide, NR1X (truncate missing the second conserved alpha-helical area R2, as well as both the proline and the choline binding areas). Eighty percent of the mice actively immunized with the NR1X CBP truncate prior to challenge survived the 14 day observation period. By contrast, all mice immunized with a control (sham mice) of PBS and adjuvant were dead by day 8.

Eighty percent of the mice immunized with CbpA truncate protein NR1X survived the challenge for 14 Days (results shown in FIG. 5). All sham immunized mice were dead by day 8.

B. Active Protection with NR1XR2 Truncate Vaccination

C3H/HeJ mice (10/group) were immunized intraperitoneally with CbpA truncate protein NR1XR2 (15 μg in 50 μl PBS, plus 50 μl Complete Freund's Adjuvant). A group of 10 control immunized mice received pneumococcal recombinant protein SP90 and adjuvant. A second immunization was administered four weeks later, 15 μg protein i.p. with Incomplete Freund's Adjuvant. Blood was drawn (retro-orbital bleed) at weeks 3, 6, and 9 for analysis of immune response. The ELISA end point anti-CbpA truncate titer of pooled sera from the 10 CbpA immunized mice at 9 weeks was 4,096,000. Mice were challenged at week 10 with 680 CFU serotype 6B S. pneumoniae strain SPSJ2. Mice were monitored for 14 days for survival.

Figure 6:
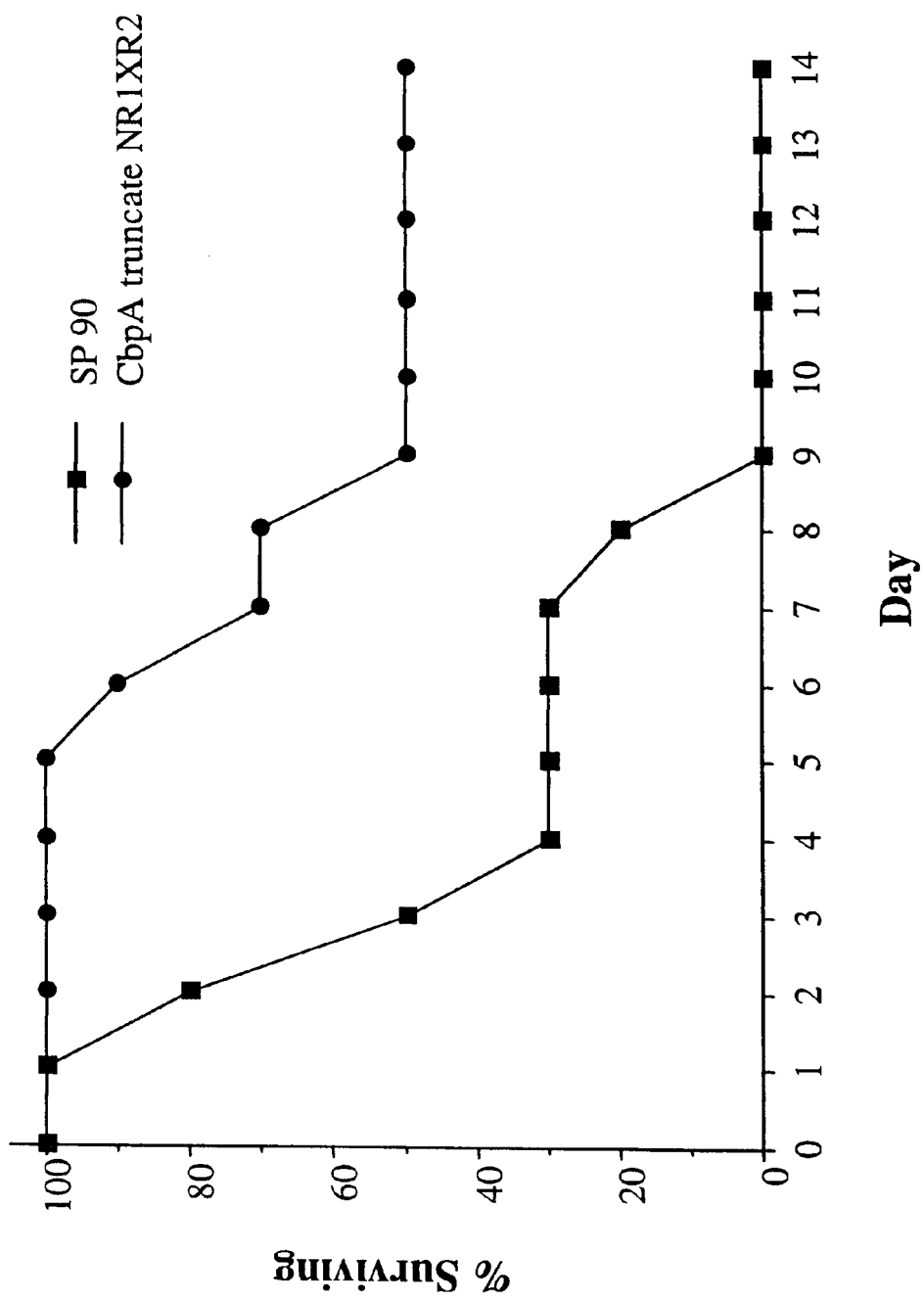
FIG. 6 reports the results for active immunity protection against 680 cfu virulent serotype 6B *S. pneumoniae* SPSJ2 (in mice) that was provided by immunization with a pneumococcal CBP truncate polypeptide, NR1XR2 (truncate missing both the proline and the choline binding areas, but including two conserved alpha-helical areas R1 and R2). Fifty percent of the mice actively immunized with the NR1XR2 CBP truncate prior to challenge survived the 14 day observation period. By contrast, all mice immunized with a control (SP90) protein and adjuvant were dead by day 9.
Figure 7:
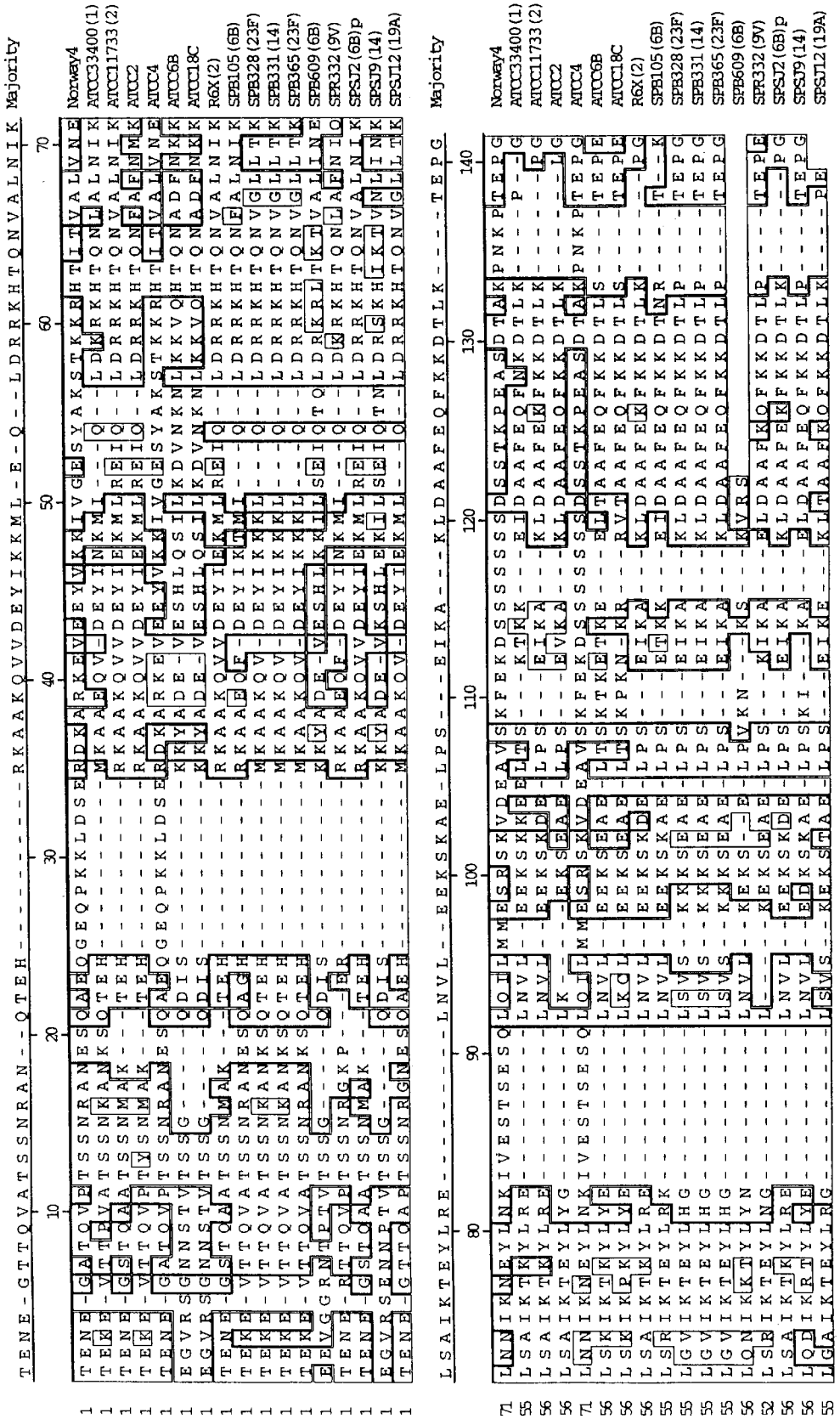
FIG. 7 is an alignment report of the amino terminus of CBP polypeptides from various types of *S. pneumoniae* and a consensus sequence is reported at the top of each row (sets of lines) of the comparison. The consensus sequence for the comparison is listed as the "Majority" sequence (SEQ ID NO:36). One letter codes are utilized to represent the sequences which are aligned for a "best fit" comparison wherein dashes in a sequence indicate spacing gaps of the contiguous sequence. Residues that differ from the consensus sequence appear in small boxes.
Figure 8:
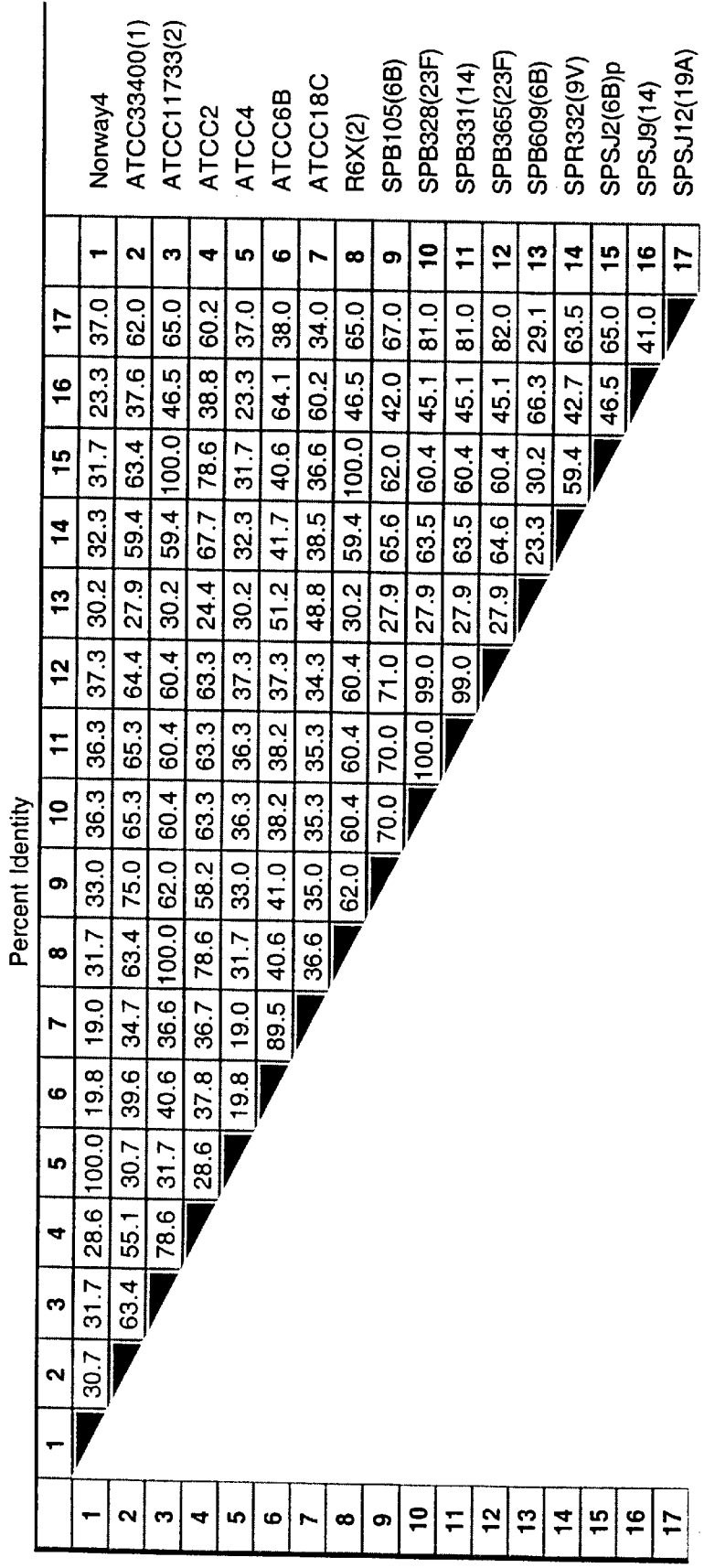
FIG. 8 shows the sequence pair distances for the amino acid sequences as described for FIG. 7 and set forth therein. A Clustal method with identity residue weight table is used. The percent similarity for such a comparison is reported for the amino acid sequences set forth in FIG. 7.
Figure 9:
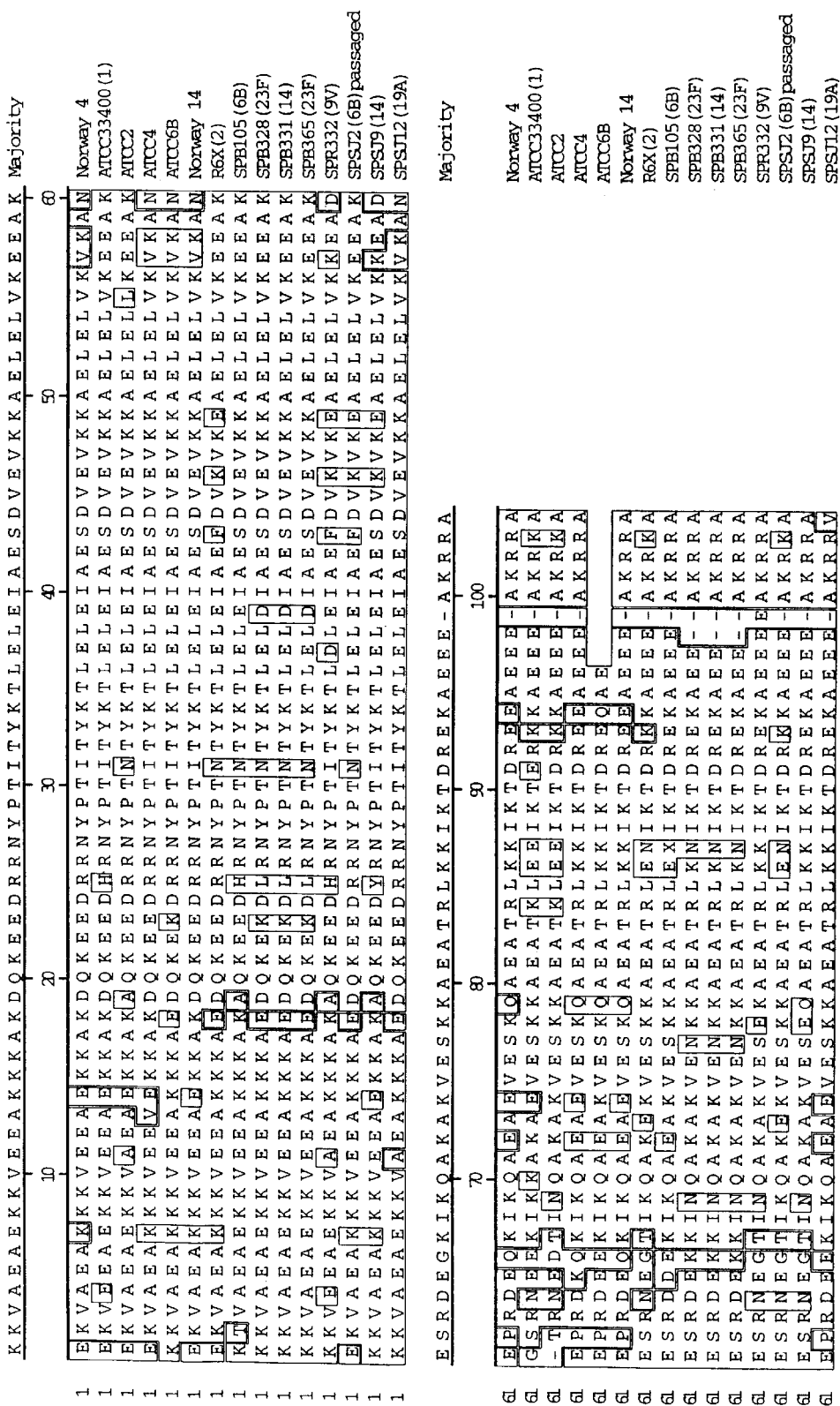
FIG. 9 is an alignment report for a first helical region in the amino acid sequences of CBP polypeptides from various types of *S. pneumoniae* and a consensus sequence is reported at the top of each row (sets of lines) of the comparison. The consensus sequence for the comparison is listed as the "Majority" sequence (SEQ ID NO:38). One letter codes are utilized to represent the sequences which are aligned for a "best fit" comparison wherein dashes in a sequence indicate spacing gaps of the contiguous sequence. Residues that differ from the consensus sequence appear in small boxes.
Figure 10:
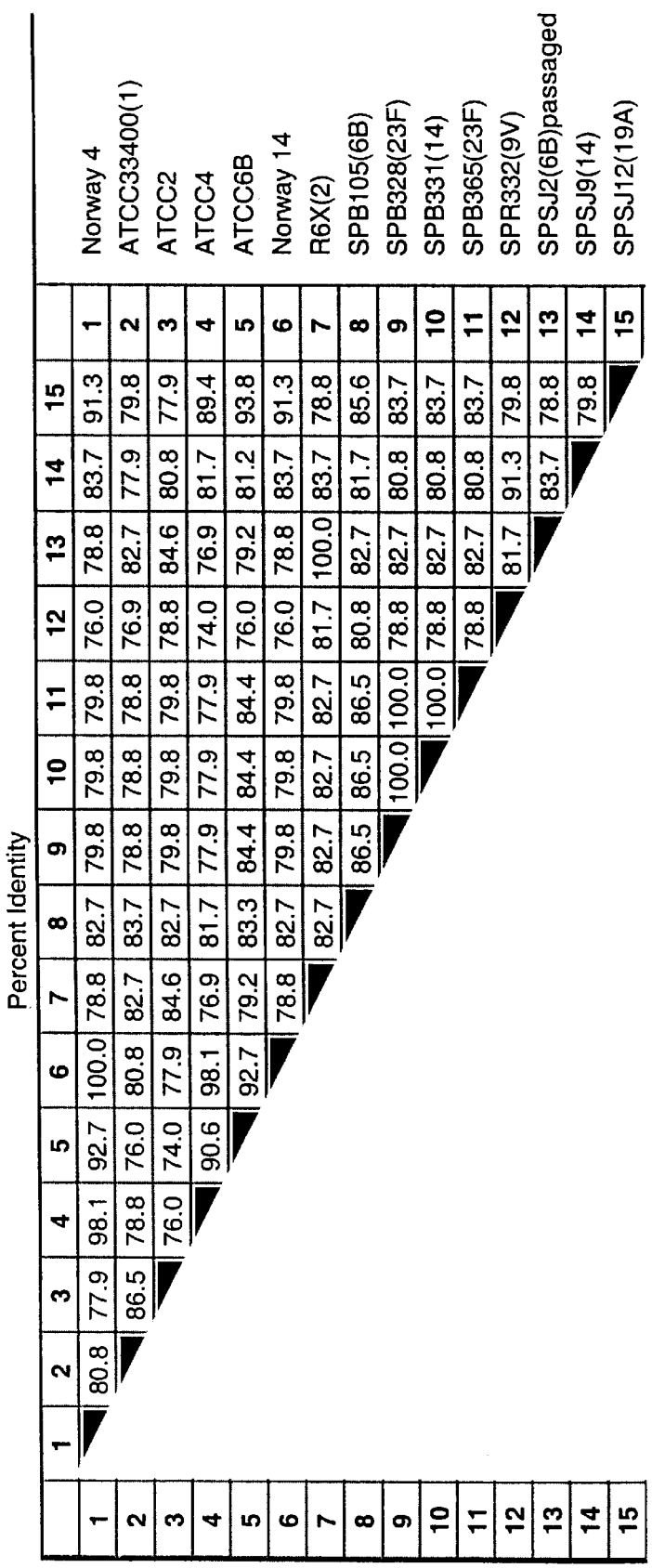
FIG. 10 shows the sequence pair distances for the amino acid sequences as described for FIG. 9 and set forth therein. A Clustal method with identity residue weight table is used. The percent similarity for such a comparison is reported for the amino acid sequences set forth in FIG. 9.
Figure 11:
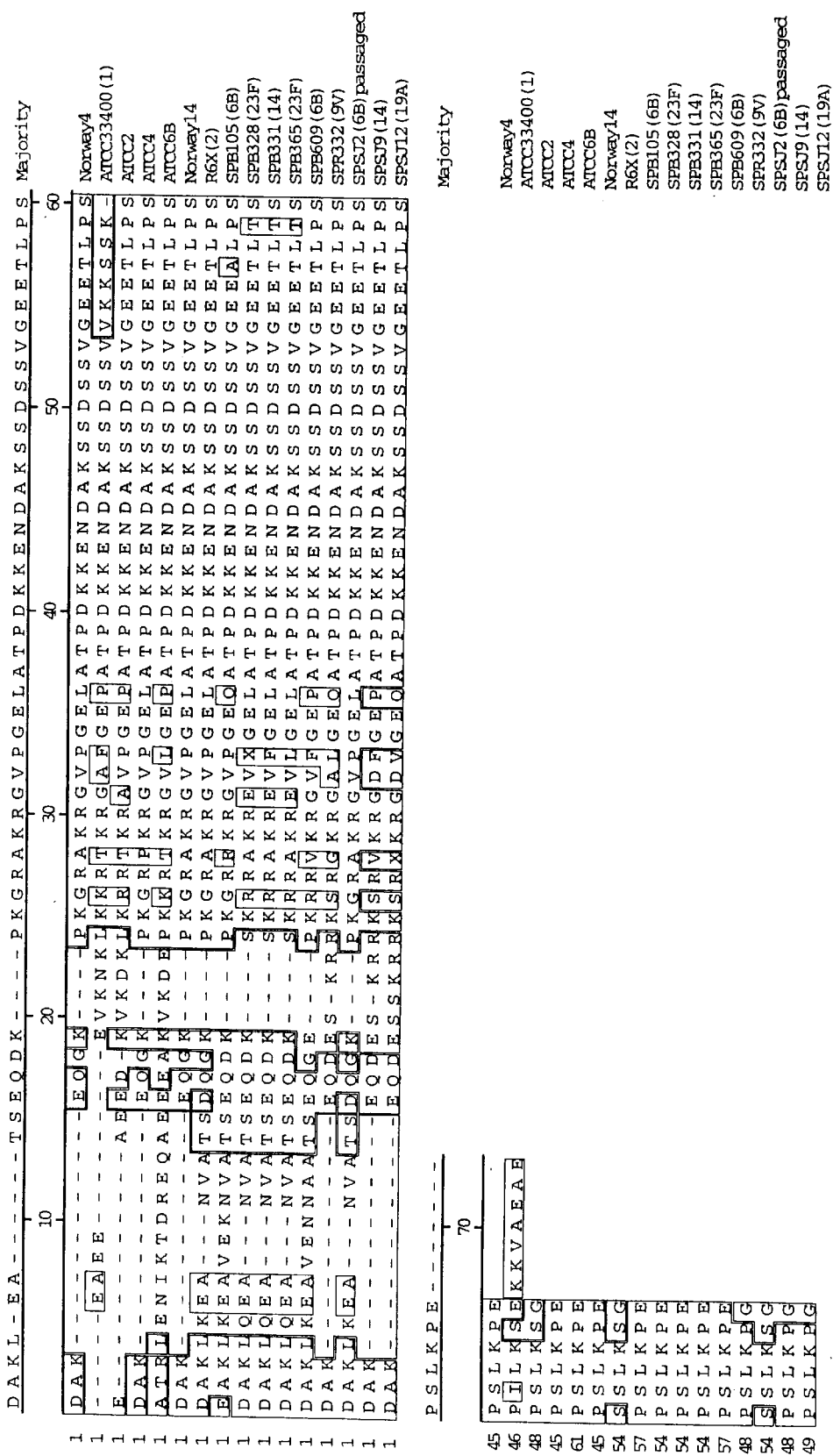
FIG. 11 is an alignment report for the region X in the amino acid sequences of CBP polypeptides from various types of *S. pneumoniae* and a consensus sequence is reported at the top of each row (sets of lines) of the comparison. The consensus sequence for the comparison is listed as the "Majority" sequence (SEQ ID NO:37). One letter codes are utilized to represent the sequences which are aligned for a "best fit" comparison wherein dashes in a sequence indicate spacing gaps of the contiguous sequence. Residues that differ from the consensus sequence appear in small boxes.
Figure 13:
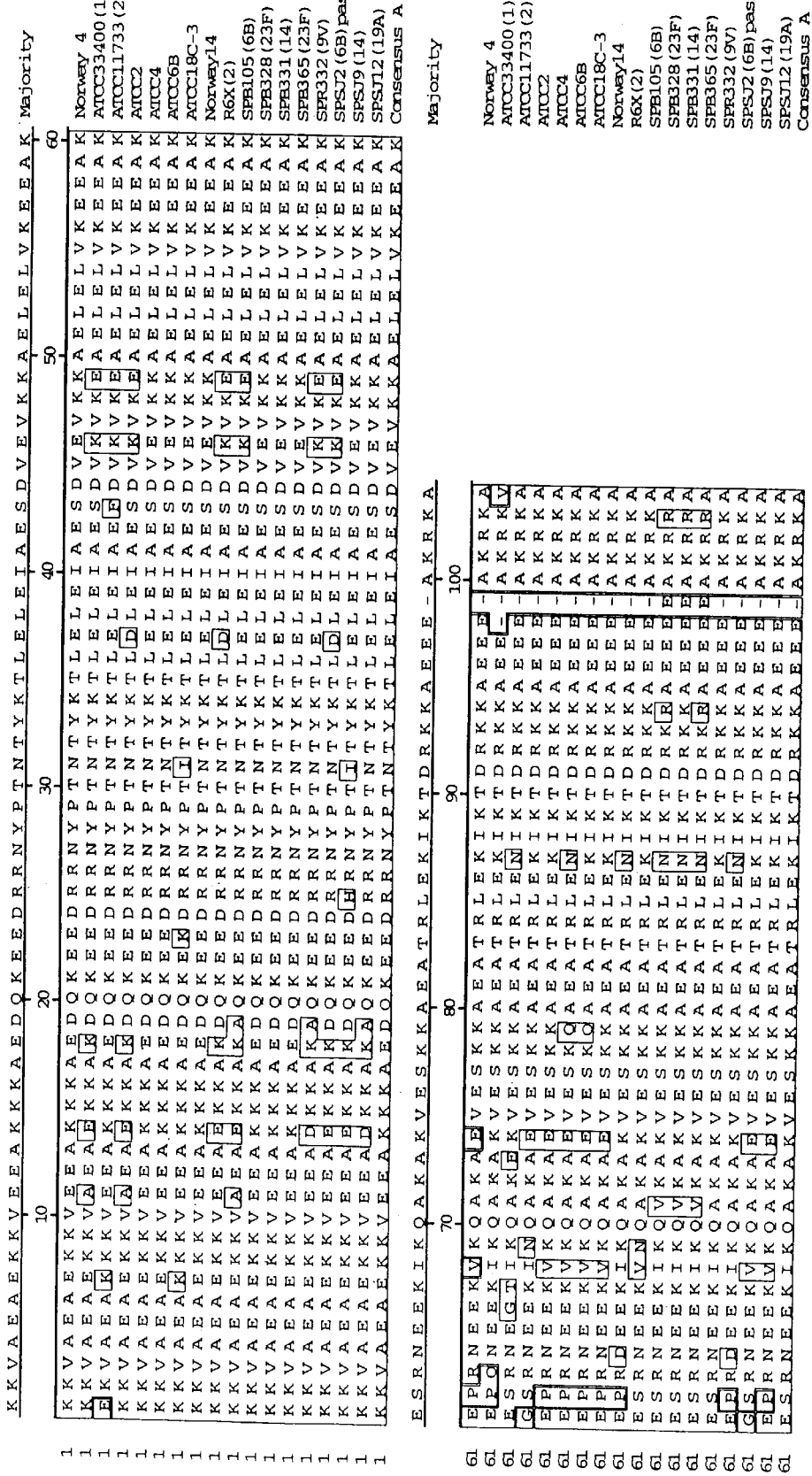
FIG. 13 is an alignment report for the second helical region A in the amino acid sequences of CBP polypeptides from various types of *S. pneumoniae* and a consensus sequence is reported at the top of each row (sets of lines) of the comparison. The consensus sequence for the comparison is listed as the "Majority" sequence (SEQ ID NO:1). One letter codes are utilized to represent the sequences which are aligned for a "best fit" comparison wherein dashes in a sequence indicate spacing gaps of the contiguous sequence. Residues that differ from the consensus sequence appear in small boxes.
Figure 14:
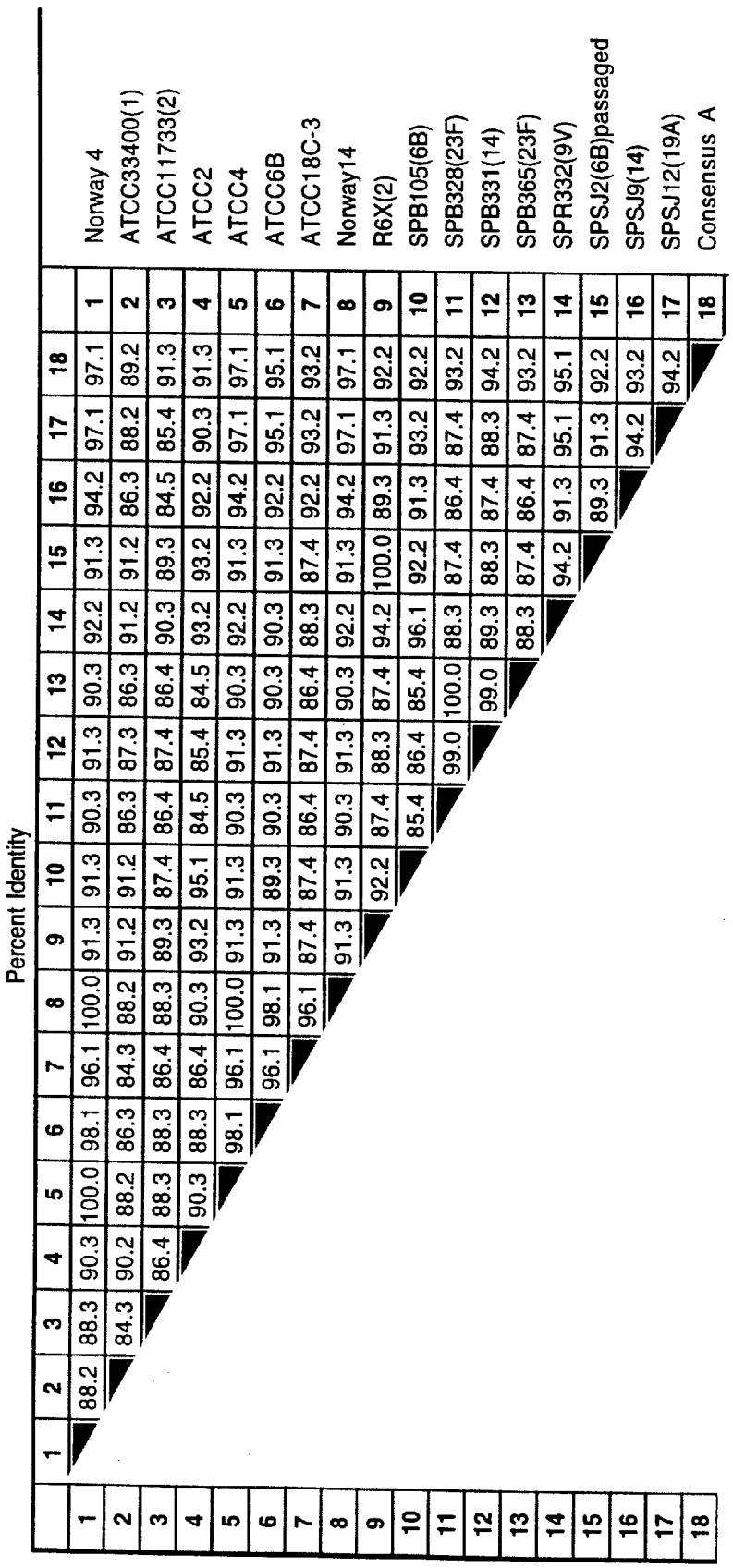
FIG. 14 shows the sequence pair distances for the amino acid sequences as described for FIG. 13 and set forth therein. A Clustal method with identity residue weight table is used. The percent similarity for such a comparison is reported for the amino acid sequences set forth in FIG. 13.
Figure 15:
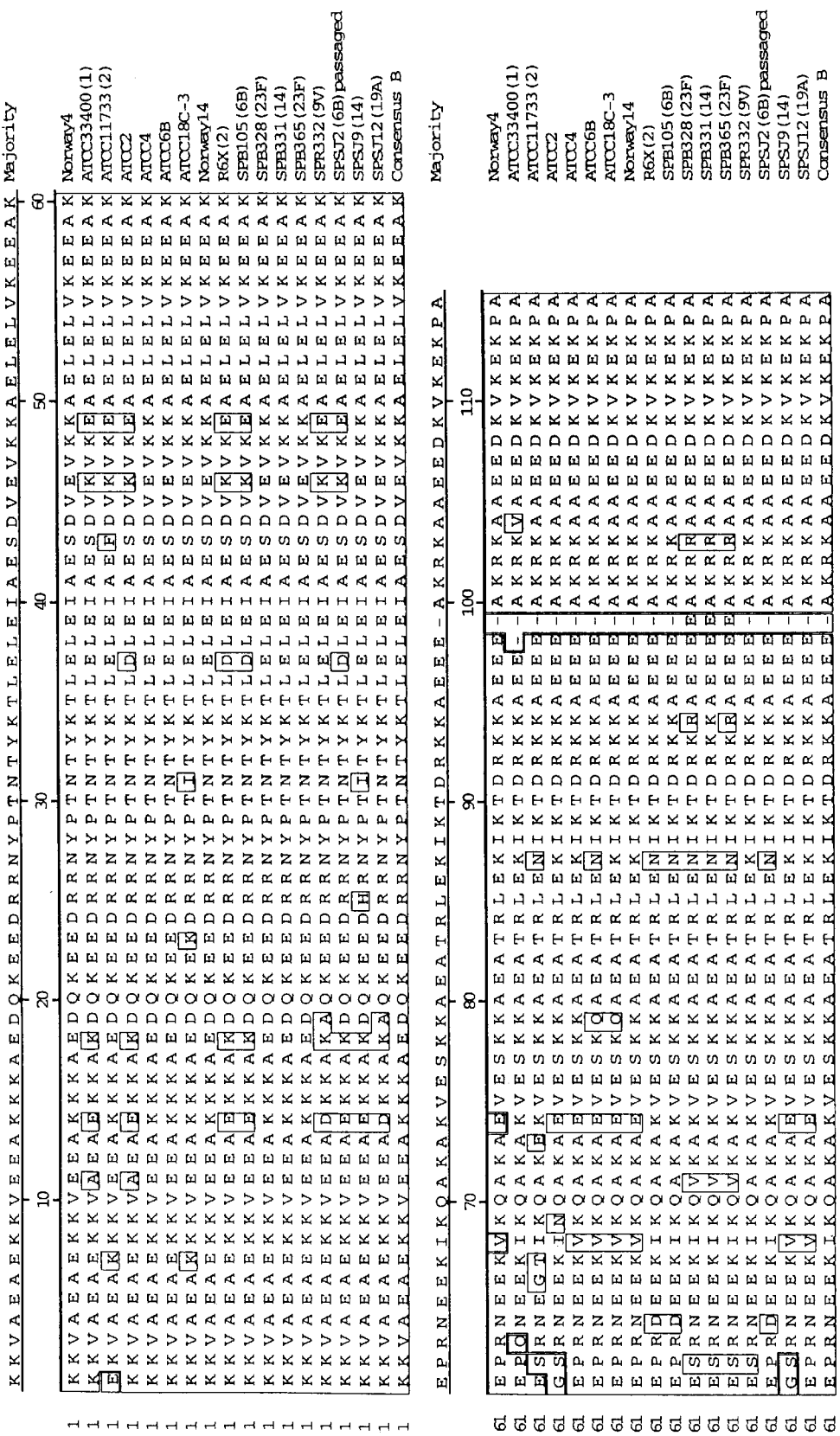
FIG. 15 is an alignment report for the second helical region B in the amino acid sequences of CBP polypeptides from various types of *S. pneumoniae* and a consensus sequence is reported at the top of each row (sets of lines) of the comparison. The consensus sequence for the comparison is listed as the "Majority" sequence (SEQ ID NO:19). One letter codes are utilized to represent the sequences which are aligned for a "best fit" comparison wherein dashes in a sequence indicate spacing gaps of the contiguous sequence. Residues that differ from the consensus sequence appear in small boxes.
Figure 16:
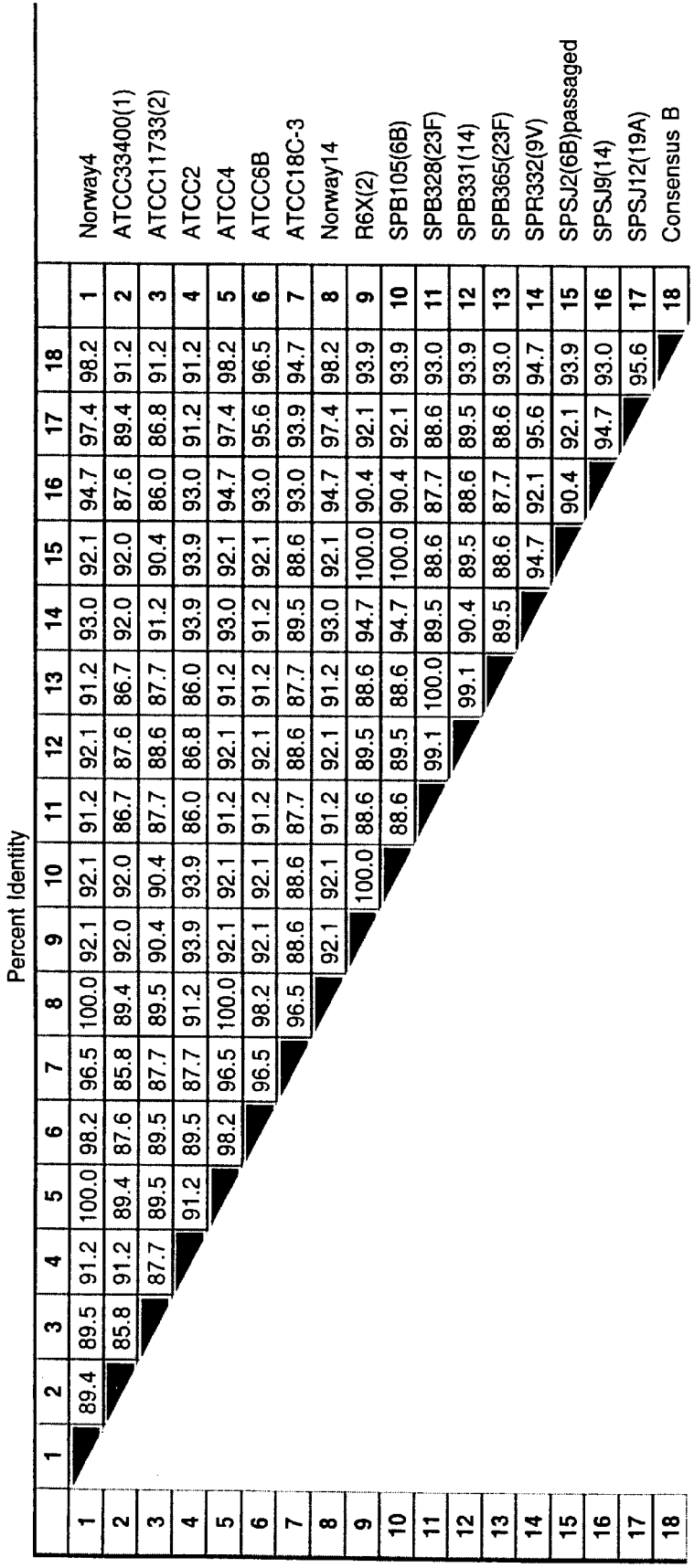
FIG. 16 shows the sequence pair distances for the amino acid sequences as described for FIG. 15 and set forth therein. A Clustal method with identity residue weight table is used. The percent similarity for such a comparison is reported for the amino acid sequences set forth in FIG. 15.

Fifty percent of the mice immunized with CbpA truncate protein NR1XR2 survived the challenge for 14 days (results shown in FIG. 6). All control immunized mice were dead by day 9.

These data demonstrate that immunization with recombinant CbpA truncate proteins elicit production of specific antibodies capable of protecting against systemic pneumococcal infection and death. The data further indicate that the choline-binding region is not necessary for protection, as the immunogens were truncated proteins NR1X and NR1XR2. Additionally, the results suggest that a single amino terminal repeat may be sufficient to elicit a protective response. Cross protection is demonstrated as the recombinant pneumococcal protein was generated based on serotype 4 DNA sequence and protection was observed following challenge with a serotype 6B isolate.

Numerous modifications and variations of the present invention are possible in light of the above teachings and, therefore, within the scope of the appended claims, the invention may be practiced otherwise than as particularly described.

What is claimed is:

1. A vaccine for treating or protecting against pneumococcal infection comprising a polypeptide in a pharmaceutically acceptable carrier wherein said polypeptide comprises an alpha helical portion at least 90% identical to the sequence of SEQ ID NO: 1 and wherein said polypeptide does not comprise a choline binding portion and does not comprise an HPS portion, the polypeptide content of said vaccine being in an amount effective for treating or protecting against pneumococcal infection.

2. The vaccine of claim 1 wherein said alpha helical portion is at least about 95% identical to the sequence of SEQ ID NO: 1.

3. The vaccine of claim 1 wherein said alpha helical portion is at least about 97% identical to the sequence of SEQ ID NO: 1.

4. The vaccine of claim 1 wherein said alpha helical portion is identical to the sequence of SEQ ID NO: 1.

5. The vaccine of claim 1 wherein said alpha helical portion is also at least 90% identical to the alpha helical portion of a pneumococcal surface binding protein found in a pneumococcal bacterium.

6. The vaccine of claim 5 wherein said alpha helical portion is also at least 95% identical to the alpha helical portion of said pneumococcal surface binding protein.

7. The vaccine of claim 5 wherein said alpha helical portion is also at least 97% identical to the alpha helical portion of said pneumococcal surface binding protein.

8. The vaccine of claim 5 wherein said alpha helical portion is also identical to the alpha helical portion of said pneumococcal surface binding protein.

9. The vaccine of claim 1 wherein said vaccine when administered to a a mammal elicits an antibody that protects against pneumococcal infection in said mammal.

10. The vaccine of claim 9 wherein said mammal is a human being.

11. The vaccine according to claim 1, wherein said vaccine is for preventing or treating otitis media, sepsis, memingitis, or 10 bar pneumonia infections.

12. The vaccine according to claim 11, wherein said vaccine is for otitis media infections caused by S. pneumoniae.

13. The vaccine of claim 1 wherein said vaccine further comprises an adjuvant.

* * * * *

UNITED STATES PATENT AND TRADEMARK OFFICE
CERTIFICATE OF CORRECTION

PATENT NO.    : 6,503,511 B1
DATED         : January 7, 2003
INVENTOR(S)   : Theresa M. Wizemann It is certified that error appears in the above-identified patent and that said Letters Patent is hereby corrected as shown below:

<u>Column 11,</u>
Line 3, delete "trucates" and insert therefor -- truncates --

<u>Column 18,</u>
Line 38, delete "NR1 XR2PC" and insert therefor -- NR1XR2PC --
Line 46, delete "Childern's" and insert therefor -- Children's --

<u>Column 82,</u>
Line 47, delete "memingitis" and insert therefor -- meningitis --
Line 47, delete "10bar" and insert therefor -- lobar --

Signed and Sealed this

Eighth Day of April, 2003

JAMES E. ROGAN
*Director of the United States Patent and Trademark Office*